United States Patent
Edge et al.

(10) Patent No.: US 10,143,711 B2
(45) Date of Patent: Dec. 4, 2018

(54) PATHWAYS TO GENERATE HAIR CELLS

(75) Inventors: Albert Edge, Brookline, MA (US);
Fuxin Shi, Winchester, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 13/130,607

(22) PCT Filed: Nov. 24, 2009

(86) PCT No.: PCT/US2009/065747
§ 371 (c)(1),
(2), (4) Date: Aug. 26, 2011

(87) PCT Pub. No.: WO2010/060088
PCT Pub. Date: May 27, 2010

(65) Prior Publication Data
US 2011/0305674 A1      Dec. 15, 2011

Related U.S. Application Data

(60) Provisional application No. 61/117,515, filed on Nov. 24, 2008.

(51) Int. Cl.
| | | |
|---|---|---|
| A61K 31/16 | (2006.01) | |
| A61K 35/30 | (2015.01) | |
| A61K 45/06 | (2006.01) | |
| A61K 38/17 | (2006.01) | |

(52) U.S. Cl.
CPC .............. *A61K 35/30* (2013.01); *A61K 31/16* (2013.01); *A61K 38/1709* (2013.01); *A61K 45/06* (2013.01)

(58) Field of Classification Search
CPC ....... A61K 9/0046; A61K 38/005; C12N 9/00
See application file for complete search history.

(56) References Cited

U.S. PATENT DOCUMENTS

| | | |
|---|---|---|
| D309,535 S | 7/1990 | Wilson |
| D360,535 S | 7/1995 | Sjoberg |
| D447,031 S | 8/2001 | Oh |
| 6,417,185 B1 | 7/2002 | Goff et al. |
| 6,489,344 B1 | 12/2002 | Nuss et al. |
| 6,608,063 B2 | 8/2003 | Nuss et al. |
| 6,756,511 B2 | 6/2004 | Castro Pineiro et al. |

(Continued)

FOREIGN PATENT DOCUMENTS

| | | |
|---|---|---|
| JP | 2006-117536 | 5/2006 |
| JP | 2006/520386 | 9/2006 |

(Continued)

OTHER PUBLICATIONS

Lu et al., Develop. Neurobiol. 68: 1059-1075.*

(Continued)

*Primary Examiner* — Erin M. Bowers
(74) *Attorney, Agent, or Firm* — Fish & Richardson P.C.

(57) ABSTRACT

This disclosure relates to methods and compositions for modulating (e.g., increasing) Atoh1 activity (e.g., biological activity) and/or expression (e.g., transcription and/or translation) in vivo and/or in vitro, e.g., in a biological cell and/or in a subject. The methods and compositions described herein can be used in the treatment of diseases and/or disorders that would benefit from increased Atoh1 expression in a biological cell.

13 Claims, 22 Drawing Sheets

Specification includes a Sequence Listing.

(56) References Cited

U.S. PATENT DOCUMENTS

| | | | |
|---|---|---|---|
| 6,890,956 | B2 | 5/2005 | Churcher et al. |
| 6,984,626 | B2 | 1/2006 | Nadin et al. |
| 7,049,296 | B2 | 5/2006 | Castro Pineiro et al. |
| 7,101,895 | B2 | 9/2006 | Churcher et al. |
| 7,138,400 | B2 | 11/2006 | Collins et al. |
| 7,144,910 | B2 | 12/2006 | Madin et al. |
| 7,183,303 | B2 | 2/2007 | Castro Pineiro et al. |
| D646,625 | S | 10/2011 | Youn |
| 8,188,069 | B2 | 5/2012 | Miller et al. |
| 8,617,810 | B2 | 12/2013 | Heller et al. |
| 8,673,634 | B2 | 3/2014 | Li et al. |
| 2004/0029862 | A1 | 2/2004 | Belanger et al. |
| 2004/0049038 | A1 | 3/2004 | Collins et al. |
| 2004/0186147 | A1 | 9/2004 | Hannam et al. |
| 2005/0019801 | A1 | 1/2005 | Rubin et al. |
| 2005/0119293 | A1 | 6/2005 | Collins et al. |
| 2005/0143369 | A1 | 6/2005 | Castro Pineiro et al. |
| 2005/0182109 | A1 | 8/2005 | Collins et al. |
| 2005/0182111 | A1 | 8/2005 | Pineiro et al. |
| 2005/0215602 | A1 | 9/2005 | Campbell et al. |
| 2005/0287127 | A1* | 12/2005 | Li ............... A61K 35/55 424/93.21 |
| 2008/0267929 | A1 | 10/2008 | Li et al. |
| 2009/0098093 | A1 | 4/2009 | Edge |
| 2009/0124568 | A1 | 5/2009 | Heller et al. |
| 2009/0297533 | A1 | 12/2009 | Lichter et al. |
| 2009/0306225 | A1 | 12/2009 | Lichter et al. |
| 2011/0020232 | A1 | 1/2011 | Eberhart et al. |
| 2011/0033480 | A1 | 2/2011 | Sarkar et al. |
| 2013/0210145 | A1 | 8/2013 | Edge |

FOREIGN PATENT DOCUMENTS

| | | |
|---|---|---|
| JP | 2007/503816 | 3/2007 |
| JP | 2007/526248 | 9/2007 |
| JP | 2012-509899 | 4/2012 |
| WO | WO 1998/028268 | 7/1998 |
| WO | WO 00/53632 | 9/2000 |
| WO | WO 00/59939 | * 10/2000 |
| WO | WO 2001/070677 | 9/2001 |
| WO | WO 2002/049038 | 6/2002 |
| WO | WO 2003/093251 | 11/2003 |
| WO | WO 2003/093252 | 11/2003 |
| WO | WO 2003/093253 | 11/2003 |
| WO | WO 2003/093264 | 11/2003 |
| WO | WO 2004/039370 | 5/2004 |
| WO | WO 2004/039800 | 5/2004 |
| WO | WO 2005/014553 | 2/2005 |
| WO | WO 2005/030731 | 4/2005 |
| WO | WO 06/026570 | 3/2006 |
| WO | WO 07/075911 | 7/2007 |
| WO | WO 2007/075911 | * 7/2007 |
| WO | WO 08/076556 | 11/2007 |
| WO | WO 08/076556 | 6/2008 |
| WO | WO 2009/087130 | 7/2009 |
| WO | WO 10/060088 | 5/2010 |
| WO | WO 2010/060088 | 5/2010 |

OTHER PUBLICATIONS

Lu et al., Develop. Neurobiol. 68: 1059-1075 (2008).*
Yamamoto et al., J. Mol. Med. 84: 37-45 (2006).*
Huawei et al., "Generation of hair cells by stepwise differentiation of embryonic stem cells," Proc. Natl. Acad. Sci. U.S.A., 23:13495-13500 (2003).
Extended European Search Report issued in EP 0982830, dated Dec. 7, 2012.
International Preliminary Report on Patentability for PCT/US2009/065747, dated May 24, 2011.
Declaration of Non-Establishment of International Search Report for PCT/US2009/065747, dated Apr. 8, 2010.
Written Opinion of the International Searching Authority for PCT/US2009/065747, dated Apr. 8, 2010.

Aletsee et al., "The disintegrin Kistrin inhibits neurite extension from spiral ganglion explants cultured on laminin," Audiol. Neurootol., 6:57-65 (2001).
Artavanis-Tsakonas et al., "Notch Signaling," Sci., 268: 225-232 (1995).
Bartolami et al., "Appearance and Distribution of the 275 kD Hair-Cell Antigen During Development of the Avian Inner Ear," J. Comp. Neurol., 314:777-788 (1991).
Brors et al., "EphA4 Provides Repulsive Signals to Developing Cochlear Ganglion Neurites Mediated through Ephrin-B2 and —B3," J. Comp. Neurol., 462:90-100 (2003).
Bryant et al., "Sensory organ development in the inner ear: Molecular and cellular mechanisms," British Medical Bulletin, 63:39-57 (2002).
Burton et al., "The role of Pax2 in mouse inner ear development," Dev. Biol., 272:161-175 (2004).
Cau et al., "Mash1 activates a cascade of bHLH regulators in olfactory neuron progenitors," Develop., 124:1611-1621 (1997).
Charron et al., "The Morphogen Sonic Hedgehog is an Axonal Chemoattractant that Collaborates with Netrin-1 in Midline Axon Guidance," Cell., 113:11-23 (2003).
Chen et al., "The role of Math1 in inner ear development: Uncoupling the establishment of the sensory primordium from hair cell fate determination," Develop., 129:2495-2505 (2002).
Colter et al., "Rapid expansion of recycling stem cells in cultures of plastic-adherent cells from human bone marrow," Proc. Natl. Acad. Sci. U.S.A , 97:3213-3218 (2000).
Corrales et al., "Engraftment and Differentiation of Embryonic Stem Cell-Derived Neural Progenitor Cells in the Cochlear Nerve Trunk: Growth of Processes into the Organ of Corti," J. Neurobiol., 66:1489-500 (2006).
Cosgrove et al., Am. J. Pathol., 157:1649-59 (2000).
Dezawa et al., "Specific induction of neuronal cells from bone marrow stromal cells and application for autologous transplantation," J. Clin. Invest., 113:1701-1710 (2004).
Doyonnas et al., "Hematopoietic contribution to skeletal muscle regeneration by myelomoncytic precursors," Proc. Natl. Acad. Sci. U.S.A, 101:13507-13512 (2004).
Edge et al., "Current Applications of Cellular Xenografts," Trans. Proc., 32:1169-1171 (2000).
Extended European Search Report issued in corresponding European Patent Application No. 07871464.9, dated Nov. 17, 2010.
Fred Gage, Nature, 392:18-24 (1998).
Fritzsch et al., "Atoh1 Null Mice Show Directed Afferent Fiber Growth to Undifferentiated Ear Sensory Epithelia Followed by Incomplete Fiber Retention," Dev. Dyn., 233:570-583 (2005).
Fritzsch et al., "Lack of Neurotrophin 3 Causes Losses of Both Classes of Spiral Ganglion Neurons in the Cochlea in a Region-Specific Fashion," J. Neurosci., 17:6213-6225 (1997).
Gillespie et al., "LIF is more potent than BDNF in promoting neurite outgrowth of mammalian auditory neurons in vitro," Neuro. Rep., 12:275-279 (2001).
Gowan et al., "Crossinhibitory Activities of Ngn1 and Math1 Allow Specification of Distinct Dorsal Interneurons," Neuron., 31:219-232 (2001).
Hawkins et al., "The developmental genetics of auditory hair cells," Hum. Mol. Genet., 13:R289-296 (2004).
Heller et al., "Parvalbumin 3 is an Abundant $Ca^{2+}$Buffer in Hair Cells," J. Assoc. Res. Otolaryngol., 3:488-498 (2002).
Helms et al., "Autoregulation and multiple enhancers control Math1 expression in the developing nervous system," Develop., 127:1185-1196 (2000).
Helms et al., "Overexpression of MATH1 Disrupts the Coordination of Neural Differentiation in Cerebellum Development," Mol. Cell. Neurosci., 17:671-682 (2001).
Hermann et al., "Efficient generation of neural stem cell-like cells from adult human bone marrow stromal cells," J. Cell. Sci., 117:4411-4422 (2004).
Herzog et al., "Plasticity of marrow-derived stem cells," Blood, 102:3483-3493 (2003).
Hess et al., "Bone marrow-derived stem cells initiate pancreatic regeneration," Nat. Biotechnol., 21:763-770 (2003).

(56) References Cited

OTHER PUBLICATIONS

Hu et al., "Survival and neural differentiation of adult neural stem cells transplanted into the mature inner ear," Exper. Cell. Res., 302:40-47 (2005).
Hu et al., Stem Cell and Development, 15:449-459 (2006).
International Preliminary Report on Patentability issued in corresponding International Application No. PCT/US2007/084654, dated May 28, 2009.
International Search Report issued in corresponding International Application No. PCT/US2007/84654, dated Oct. 3, 2008.
Ito et al., "Neurotrophins Facilitate Neuronal Differentiation of Cultured Neural Stem Cells Via Induction of mRNA Expression of Basic Helix-Loop-Helix Transcription Factors Mash1 and Math1," J. Neurosci. Res., 71:648-658 (2003).
Ivanov et al., "Genes required for *Drosophila* nervous system development identified by RNA interference," Proc. Nat. Acad. Sci., 101:16216-16221 (2004).
Izumikawa et al., "Auditory hair cell replacement and hearing improvement by Atoh1 gene therapy in deaf mammals," Natl. Med., 11(3):271-276 (Mar. 2005).
Jeon et al., "Bone marrow mesenchymal stem cells are progenitors in vitro for inner ear hair cells," Molecular and Cellular Neurosciences, 34:59-68 (2007).
Jiang et al., "Neuroectodermal differentiation from mouse multipotent adult progenitor cells," Proc. Natl. Acad. Sci .U.S.A, 100:11854-11860 (2003).
Jiang et al., "Pluripotency of mesenchymal stem cells derived from adult marrow," Nature, 418:41-49 (2002).
Kicic et al., "Differentiation of Marrow Stromal Cells into Photoreceptors in the Rat Eye," J. Neurosci., 23:7742-7749 (2003).
Kiernan et al., "Sox2 is required for sensory organ development in the mammalian inner ear," Nature, 434:1031-1035 (2005).
Kim et al., "Dopamine neurons derived from embryonic stem cells function in an animal model of Parkinson's disease," Nature, 418:50-6 (2002).
Kim et al., "NeuroD-null mice are deaf due to a severe loss of the inner ear sensory neurons during development," Develop., 128:417-426 (2001).
Kondo et al., "Sonic Hedgehog and retinoic acid synergistically promote sensory fate specification from bone marrow-derived pluripotent stem cells," Proc. Natl. Acad. Sci. U.S.A., 102(13):4789-4794 (Mar. 2005).
Lanford et al., "Notch signalling pathway mediates hair cell development in mammalian cochlea," Nature Genetics, 21:289-292 (1999).
Lang et al., "Contribution of Bone Marrow Hematopoietic Stem Cells to Adult Mouse Inner Ear: Mesenchymal Cells and Fibrocytes," J .Comp. Neurol., 496:187-201 (2006).
Lee et al., "Efficient generation of midbrain and hindbrain neurons from mouse embryonic stem cells," Nat. Biotech., 18:675-9, (2000).
Leon et al.,. "Insulin-Like Growth Factor-I Regulates Cell Proliferation in the Developing Inner Ear, Activating Glycosyl-Phosphatidylinositol Hydrolysis and Fos Expression," Endocrinol., 136:3494-3503 (1995).
Li et al., "Correlation of Pax-2 Expression with Cell Proliferation in the Developing Chicken Inner Ear," J. Neurobiol., 60:61-70 (2004).
Li et al., "Generation of hair cells by stepwise differentiation of embryonic stem cells," Proc. Natl. Acad. Sci U.S.A., 100:13495-13500 (2003).
Li et al., "Pluripotent stem cells from the adult mouse inner ear," Nat. Med., 9:1293-1299 (2003).
Li et al., "Specification of motoneurons from human embryonic stem cells," Nat. Biotechnol., 23:215-21 (2005).
Li et al., "Stem cells as therapy for hearing loss," Trends Mol. Med., 10:309-315 (2004).
Lumpkin et al., "Math1-driven GFP expression in the developing nervous system of transgenic mice," Gene. Expr. Patterns, 3:389-395 (2003).
Ma et al., "Neurogenin 1 Null Mutant Ears Develop Fewer, Morphologically Normal Hair Cells in Smaller Sensory Epithelia Devoid of Innervation," Assoc. Res. Otolarnyngol., 1:129-143 (2000).

Mangi et al., "Mesenchymal stem cells modified with Akt prevent remodeling and restore performance of infarcted hearts," Nat. Med., 9:1195-201 (2003).
Matei et al., "Smaller Inner Ear Sensory Epithelia in Neurog1 Null Mice Are Related to Earlier Hair Cell Cycle Exit," Dev. Dyn., 234:633-50 (2005).
Matsui et al., Drug Discov. Today, 10:1307-12 (2005).
Mezey et al., "Transplanted bone marrow generates new neurons in human brains," Proc. Natl. Acad. Sci. U.S.A., 100:1364-1369 (2003).
Murry et al., "Haematopoietic stem cells do not transdifferentiate into cardiac myocytes in myocardial infarcts," Nature., 428:664-668 (2004).
Naito Yasushi et al., "Transplantation of bone marrow stromal cells into the cochlea of chinchillas," NeuroReport, Lippincott Williams & Wilkins, 15:1-4 (2004).
Office Action issued in JP2009-537328 dated Feb. 12, 2013 (7 pages).
Oshima et al., "Differential Distribution of Stem Cells in the Auditory and Vestibular Organs of the Inner Ear," J. Assoc. Res .Otolaryngol., 8:18-31 (2007).
Pagani et al., "Autologous Skeletal Myoblasts Transplanted to Ischemia-Damaged Myocardium in Humans," J. Am. Coll. Cardiol., 41:879-888 (2003).
Patzel et al., "Design of siRNAs producing unstructured guide-RNAs results in improved RNA interference efficiency," Nature Biotechnol., 23:1440-1444 (2005).
Pauley et al., "Expression and Function of FGF10 in Mammalian Inner Ear Development," Dev. Dyn., 227:203-215 (2003).
Pedersen, "Cells for Medicine," Scientif. Am., 280:68-73 (1999).
Petit et al., Annu Rev Genomics Hum Genet., 2:271-97 (2001).
Pirvola et al., "Neurotrophic Factors during Inner Ear Development," Curr. Top. Dev. Biol., 57:207-223 (2003).
Pittenger et al., "Multilineage Potential of Adult Human Mesenchymal Stem Cells," Sci., 284:143-147 (1999).
Plum et al., Dev Biol., 231:334-47 (2001).
Presente et al., "Notch is required for long-term memory in *Drosophila*," Proc. Nat. Acad. Sci., 101:1764-1768 (2004).
Purow et al., "Expression of Notch-1 and Its Ligands, Delta-Like-1 and Jagged-1, Is Critical for Glioma Cell Survival and Proliferation," Cancer Res., 65:2353-2363 (2005).
Rask-Andersen et al., "Regeneration of human auditory nerve. In vitro/in video demonstration of neural progenitor cells in adult human and guinea pig spiral ganglion," Hear. Res., 203:180-191 (2005).
Sakamoto et al., Acta Otolarynol Suppl., 551:48-52 (2004).
Samstein et al., Journal of American Society of Nephrology, 12:182-193 (2001).
Sarrazin et al., "Proneural gene requirement for hair cell differentiation in the zebrafish lateral line," Dev. Biol., 295:534-545 (2006).
Satoh and Fekete, "Clonal analysis of the relationships between mechanosensory cells and the neurons that innervate them in the chicken ear," Develop., 132:1687-1697 (2005).
Stallwood et al., "Small Interfering RNA-Mediated Knockdown of Notch Ligands in Primary CD4+ T Cells and Dendritic Cells Enhances Cytokine Production," J. Immunol., 177:885-895 (2006).
Supplementary European Search Report issued in EP09828380 dated Nov. 30, 2012 (8 pages).
Wagers et al., "Little Evidence for Developmental Plasticity of Adult Hematopoietic Stem Cells," Science, 297:2256-2259 (2002).
Wang et al., "Cell fusion is the principal source of bone-marrow-derived hepatocytes," Nature, 422:897-901 (2003).
Warner et al., "Expression of ZIC Genes in the Development of the Chick Inner Ear and Nervous System," Dev. Dyn., 226:702-712 (2003).
Weimann et al., "Contribution of transplanted bone marrow cells to Purkinje neurons in human adult brains," Proc. Natl. Acad. Sci. U.S.A., 100:2088-2093 (2003).
White et al., "Mammalian cochlear supporting cells can divide and trans-differentiate into hair cells," Nature, 441:984-987 (2006).
Woods et al., "Math1 regulates development of the sensory epithelium in the mammalian cochlea," Nat. Neurosci., 7:1310-1318 (2004).

(56) References Cited

OTHER PUBLICATIONS

Written Opinion of the International Searching Authority issued in corresponding International Application No. PCT/US2007/84654, dated Oct. 3, 2008.
Yamamoto et al., "Inhibition of Notch/RBP-J signaling induces hair cell formation in neonate mouse cochleas," J. Mol. Med., 84(1):37-45 (Jan. 2006).
Zheng et al., "Induction of Cell Proliferation by Fibroblast and Insulin-Like Growth Factors in Pure Rat Inner Ear Epithelial Cell Cultures," J. Neurosci., 17:216-226 (1997).
Zheng et al., "Overexpression of Math 1 induces robust production of extra hair cells in postnatal rat inner ears," Natl. Neurosci., 3(6):580-600 (Jun. 2000).
Bouchard et al., "Pax2 and homeodomain proteins cooperatively regulate a 435 bp enhancer of the mouse Pax5 gene at the midbrain-hindbrain boundary," Develop., 127:1017-28 (2000).
Office Action issued in EP09828380.7 dated Mar. 26, 2014 (6 pages).
Office Action issued in CA2,669,693 dated Apr. 4, 2014 (4 pages).
Office Action issued in EP07871464.9 dated May 6, 2014 (5 pages).
U.S. Appl. No. 14/208,284, filed Mar. 13, 2014, Li et al.
Office Action issued in Japanese Application No. 2011-537715 dated Feb. 4, 2014 (translation) 4 pages.
Examination Report issued in Australian Patent Application No. 2007334260 dated Aug. 23, 2012 (5 pages).
Response to Restriction Requirement issued in U.S. Appl. No. 13/759,441 dated Dec. 22, 2014 filed Mar. 19, 2015 (4 pages).
Office Action issued in AU2009316264 dated Jan. 16, 2015 (5 pages).
Office Action issued in JP2011-537715 dated Jan. 20, 2015 with English translation (7 pages).
Restriction Requirement issued in U.S. Appl. No. 13/759,441 dated Dec. 22, 2014 (4 pages).
Geling et al., "A γ-secretase inhibitor blocks Notch signaling in vivo and causes a severe neurogenic phenotype in zebrafish," EMBO report, 2002, 688-694.
Zine et al., "Notch signaling regulates the pattern of auditory hair cell differentiation in mammals," Development., 2000, 127:3373-3383.
Bramhall et al., "Lgr5-Positive Supporting Cells Generate New Hair Cells in the Postnatal Cochlea," Stem Cell Reports, 2:1-12, Mar. 11, 2014.
Corwin and Cotanche, "Regeneration of Sensory Hair Cells After Acoustic Trauma," Science., 240:1772-1774, Jun. 24, 1988.
Groves, "The Challenge of Hair Cell Regeneration," Exp Biol Med (Maywood), 235(4):434-446, Apr. 2010.
Hume et al., "Expression of LHX3 and SOX2 during mouse inner ear development," Gene Expression Patterns 7:798-807, 2007.
Lin et al., "Inhibition of Notch Activity Promotes Nonmitotic Regeneration of Hair Cells in the Adult Mouse Utricles," Journal of Neuroscience., 31 (43):15329-15339, Oct. 26, 2011.
Rubel et al., "Mammalian Vestibular Hair Cell Regeneration," Science., 267(5198): 701-707, Feb. 3, 1995.
Ryals and Rubel, "Hair Cell Regeneration After Acoustic Trauma in Adult Coturnix Quail," Science, 240:1774-1776, Jun. 24, 1988.
Office Action issued in JP2015-178811, dated Mar. 7, 2017 with English translation (5 pages).
Adam et al., "Cell fate choices and the expression of Notch, Delta and Serrate homologues in the chick inner ear: parallels with *Drosophila* sense-organ development," Development, 125(23):4645-54 (Dec. 1998).
Basi et al., "Amyloid precursor protein selective gamma-secretase inhibitors for treatment Amyloid precursor protein selective gamma-secretase of Alzheimer's disease," Alzheimer's Research & Therapy, 2:36 (2010) pp. 1-21.
Batts et al., "Notch signaling and Hes labeling in the normal and drug-damaged organ of Corti," Hear Res., 249:15-22 (Mar. 2009).
Bramhall, "Lgr5-Positive Supporting Cells Generate New Hair Cells in the Postnatal Cochlea," Stem Cell Reports, Mar. 2014, 2:1-12.

Caiazzo et al., "Direct generation of functional dopaminergic neurons from mouse and human fibroblasts," Nature, 476:224-7 (Jul. 2011).
Corwin et al., "Regeneration of Sensory Hair Cells After Acoustic Trauma," Science, Jun. 1988, 240:1772-1774.
Daudet and Lewis, "Two contrasting roles for Notch activity in chick inner ear development: specification of pro sensory patches and lateral inhibition of hair-cell differentiation," Development, 132:541-51 (Feb. 2005).
Daudet et al., "Notch regulation of progenitor cell behavior in quiescent and regenerating auditory epithelium of mature birds," Dev Biol., 326(1):86-100 (Feb. 1, 2009).
Doetzlhofer et al., "Hey2 regulation by FGF provides a Notch-independent mechanism for maintaining pillar cell fate in the organ of Corti," Dev Cell, 16:58-69 (Jan. 2009).
Dong et al., "Calpain inhibitor MDL28170 modulates Aβ formation by inhibiting the formation of intermediate $A\beta_{46}$ and protecting Aβ from degradation," The FASEB Journal, Dec. 2005, 21 pages.
Eatock and Rusch, "Developmental changes in the physiology of hair cells," Cell & Developmental Biology, 1997, 8:265-275.
European Search Report in Application No. 13836099, dated Mar. 8, 2016, 9 Pages.
Goycoolea and Lundman, "Round window membrane. Structure function and permeability: a review," Microsc Res Tech., 36:201-11 (Feb. 1, 1997).
Haapasalo and Kovacs; "The Many Substrates of Presenilin/γ-Secretase" Journal Alzheimers Disease. 2011: 25(1): 3-28.
Hadland et al., "γ-secretase inhibitors repress thymocyte development," Proc Natl. Acad Sci USA, 98:7487-91 (Jun. 19, 2001).
Hartman et al., "Hes5 expression in the postnatal and adult mouse inner ear and the drug-damaged cochlea," J Assoc Res Otolaryngol., 10:321-40 (Sep. 2009).
Hosoya et al., "An efficient screening method using inner-ear derived spheres for selection of compounds that induce hair cell differentiation," Neurosci Res., 61S: S57 Abstract, 2 pages (2008).
Hume et al., "Expression of LHX3 and SOX2 during mouse inner ear development," Gene Expression Patterns, 2007, 7:798-807.
Huynh et al., "The novel gamma secretase inhibitor RO4929097 reduces the tumor initiating potential of melanoma," PLoS One, 6(9):e25264, (2011) 10 pages.
Hyde et al., "Studies to investigate the in vivo therapeutic window of the γ-secretase inhibitor $N^2$-[(2S)-2-(3,5-difluorophenyl)-2-hydroxyethanoyl]1-$N^1$-[(7S)-5-methyl-6-oxo-6,7-dihydro-5H-dibenzo[b,d]azepin-7-yl]-$_L$-alaninamide (LY411,575) in the CRND8 mouse," J Pharmacol Exp Ther., 319:1133-43 (Dec. 2006).
International Preliminary Report on Patentability in International Application No. PCT/US2013/058446, dated Mar. 10, 2015, 11 pages.
International Search Report and Written Opinion in International Application No. PCT/US2013/058446, dated Dec. 26, 2013, 8 pages.
Izumikawa et al., "Auditory hair cell replacement and hearing improvement by Atoh1 gene therapy in deaf mammals," Nat Med., 11(3)271-6 (Mar. 2005).
Jeon et al., "Notch signaling alters sensory or neuronal cell fate specification of inner ear stem cells," J. Neurosci., 31:8351-8 (Jun. 8, 2011).
Kaneko et al., "Musashi1: an evolutionally conserved marker for CNS progenitor cells including neural stem cells," Dev Neurosci., 22:139-53 (2000).
Kelley, "Regulation of cell fate in the sensory epithelia of the inner ear," Nat Rev Neurosci., 7:837-49 (Nov. 2006).
Lin et al., "Inhibition of notch activity promotes non-mitotic regeneration of hair cells in the adult mouse utricles," J Neurosci., 31(43):15329-15339 (Oct. 26, 2011).
Luistro et al., "Preclinical Profile of a Potent γ-Secretase Inhibitor Targeting Notch Signaling with in vivo Efficacy and Pharmacodynamic Properties," Cancer Res, Oct. 2009, 69(19):7672-7690.
Lumpkin et al., "Math1-driven GFP expression in the developing nervous system of transgenic mice," Gene Expr Patterns, 3:389-95 (Aug. 2003).

(56) References Cited

OTHER PUBLICATIONS

Masuda et al., "Dual antitumor mechanisms of notch signaling inhibitor in a T-cell acute lymphoblastic leukemia xenograft model," Cancer Sci., 100(12):2444-2450 (Dec. 2009).
Mikulec et al., "Permeability of the round window membrane is influenced by the composition of applied drug solutions and by common surgical procedures," Otol Neurotol., 29:1020-6 (Oct. 2008).
Mitani et al., "Differential Effects between γ-Secretase Inhibitors and Modulators on Cognitive Function in Amyloid Precursor Protein-Transgenic and Nontransgenic Mice," J. Neuroscience, Feb. 2012.
Mizutari et al., "Notch Inhibition induces cochlear hair cell regeneration and recovery of hearing after acoustic trauma," Neuron, Jan. 2013, 77(1): 58-69.
Oesterle et al., "Sox2 and JAGGED1 expression in normal and drug-damaged adult mouse inner ear," J Assoc Res Otolaryngol., 9:65-89 (Mar. 2008).
Response to U.S. Final Office Action in U.S. Appl. No. 13/130,607, dated Jan. 15, 2016.
Rubel et al., "Mammalian Vestibular Hair Cell Regeneration," Science, Feb. 1995, 267(5198) :701-707.
Ryals and Rubel, "Hair Cell Regeneration After Acoustic Trauma in Adult Coturnix Quail," Science, Jun. 1988, 240:1774-1776.
Ryusuke et al., "Pharmacological inhibition of Notch signaling in the mature guinea pig cochlea" Neuroreport, Lippincott Williams and Wilkins, UK, Dec. 2007, 18(18): 1911-1914.
Sakaguchi et al., "Spatiotemporal patterns of Musashi1 expression during inner ear development," Neuroreport, 15:997-1001 (Apr. 29, 2004).
Salt and Plontke, "Principles of local drug delivery to the inner ear," Audiol Neurootol., 14:350-60 (2009).
Samon et al., "Preclinical analysis of the γ-secretase inhibitor PF-03084014 in combination with glucocorticoids in T-cell acute lymphoblastic leukemia," Mol Cancer Ther., 11(7):1565-1575 (Jul. 2012).
Vierbuchen et al., "Direct conversion of fibroblasts to functional neurons by defined factors," Nature, 463:1035-41 (Feb. 25, 2010).
Wang et al., "Dynamics of noise-induced cellular injury and repair in the mouse cochlea," J Assoc Res Otolaiyngol., 3:248-68 (Sep. 2002).
Wolfe, "γ-secretase Inhibition and Modulation for Alzheimer's Disease," Curr Alzheimer Res., 5(2):158-164 (Apr. 2008) (Author Manuscript).
Wong et al., "Chronic treatment with the gamma-secretase inhibitor L Y -411,575 inhibits beta-amyloid peptide production and alters lymphopoiesis and intestinal cell differentiation," J Biol Chem., 279:12876-82 (Mar. 26, 2004).
Zine et al., "Hest and Hes5 activities are required for the normal development of the hair cells in the mammalian inner ear," J Neurosci., 21:4712-20 (Jul. 1, 2001).
Barker, "Wnt Signaling: vol. 1: Pathway Methods and Mammalian Models," in Methods in Molecular Biology, Nov. 2008, 5-15.
Becvarovski et al., "Round Window Gentamicin Absorption: An in Vivo Human Model," Laryngoscope, Sep. 2002, 112: 1610-1613.
Beurel et al., "Glycogen synthase kinase-3 (GSIG): Regulation, actions, and diseases," Pharmacology & Therapeutics, 2015, 148:114-131.
Clevers, "Wnt/P-Catenin Signaling in Development and Disease," Cell, Nov. 2006, 127: 469-480.
Dabdoub et al., "Abstract # 443: Wnt/B-Catenin Signaling in the Developing Mammalian Cochlea," ARO 31st Annual Midwinter Meeting, Phoenix, Arizona, Feb. 16-21, 2008, 3 pages.
Dabdoub et al., "Abstract # 8: Wnt Signaling in the Developing Mammalian Cochlea," ARO 30th Annual Midwinter Meeting, Denver, Colorado, Feb. 10-15, 2007, 2 pages.
Edge and Chen, "Hair cell regeneration," Curr. Opin. Neurobiol, 2008, 18: 377-382.

Lu et al., "Abstract #: 774: The Influence of Glycogen Synthase Kinase 3 on Cell Proliferation in the Murine Vestibular Sensory Epithelium," ARO 31st Annual Midwinter Meeting, Phoenix, Arizona, Feb. 16-21, 2008, 3 pages.
Moon et al., "Wnt and B-Catenin Signaling: Diseases and Therapies," Nature Reviews, Sep. 2004, 5: 689-699.
Nadol, Jr. et al., "Degenerative Changes in the Organ of Corti and Lateral Cochlear Wall in Experimental Endolymphatic Hydrops and Human Meniere's Disease," Acta Otolaryngol, 1995, Suppl 519: 47-59.
Okubo and Hogan, "Hyperactiye Wnt signaling changes the developmental potential of embryonic lung endoderm," Journal of Biology, 2004, 3: 11.
Price, "CKI, there's more than one: casein kinase I family members in Wnt and Hedgehog signaling," Genes & Development, Feb. 15, 2006; 20(4): 399-410.
Rena et al., "D4476, a cell-permeant inhibitor of CKl, suppresses the site-specific phosphorylation and nuclear exclusion of FOXO1a," EMBO reports, Jan. 2004, 5(1): 60-65.
Shi et al., "Abstract #: 732: Interaction of B-Catenin with an Atohl 3' Enhancer Upregulates Atohl Expression and Increases Differentiation of Progenitors to Hair Cells," ARO 32nd Annual Midwinter Meeting, Baltimore, Maryland, Feb. 14-19, 2009, 3 pages.
Stahle et al., "Long-term Progression of Meniere's Disease," Acta Otolalyngol, 1991, Suppl. 485: 78-83.
Stambolic et al., "Lithium inhibits glycogen synthase kinase-3 activity and mimics Wingless signaling in intact cells," Current Biology, 1996, 6: 1664-1668.
Stevens et al., "Forced activation of Wnt signaling alters morphogenesis and sensory organ identity in the chicken inner ear," Dev. Biol, 2003, 261: 149-164.
Swan et al., "Inner ear drug delivery for auditory applications," Advanced Drug Delivery Reviews, 2008, 60: 1583-1599.
Lanzoni et al., "MDL 28170 Attenuates Gentamicin Ototoxicity," Audiological Medicine, 2005, 3:82-89.
Office Action in Japanese Application No. 2015-178811, dated Jun. 5, 2018, 12 pages (with English translation).
Office Action in Japanese Application No. 2015-531223, dated Jun. 19, 2018, 7 pages (with English translation).
Burns et al, "MYC Gene Delivery to Adult Mouse Utricles Stimulates Proliferation of Postmitotic Supporting Cells in Vitro," PLOS One, Oct. 2012, 7: 248704.
Crowder and Freeman, "Glycogen Synthase Kinase-3b Activity Is Critical for Neuronal Death Caused by Inhibiting Phosphatidylinositol 3-Kinase or Akt but Not for Death Caused by Nerve Growth Factor Withdrawal," The Journal of Biological Chemistry, Nov. 2000, 275: 34266-34271.
Forge et al., "Hair Cell Recovery in the Vestibular Sensory Epithelia of Mature Guinea Pigs," The Journal of Comparative Neurology, 1998, 397: 69-88.
Golub et al., "Hair Cell Replacement in Adult Mouse Utricles after Targeted Ablation of Hair Cells with Diphtheria Toxin," The Journal of Neuroscience, Oct. 2012, 32: 15093-15105.
Hosoya et al., "Method for efficient screening of substances inducing differentiation into inner ear hair cells with the use of spheres derived from inner ear cells," Otol Jpn, 2008, 18(4): 275 (with English translation).
Office Action in Japanese Application No. 2015-178811, dated Oct. 17, 2017, 6 pages (with English translation).
Office Action in Japanese Application No. 2015-531223, dated Jul. 11, 201, 8 pages (with English translation).
Shakoori et al., "Deregulated GSK3b activity in colorectal cancer: Its association with tumor cell survival and proliferation," Biochem and Biophys Research Comm, 2005, 334: 1365-1373.
Zaragosi et al., "Effects of GSK3 inhibitors on in vitro expansion and differentiation of human adipose-derived stem cells into adipocytes," BMC Cell Biology, 2008, 9: 11.

* cited by examiner

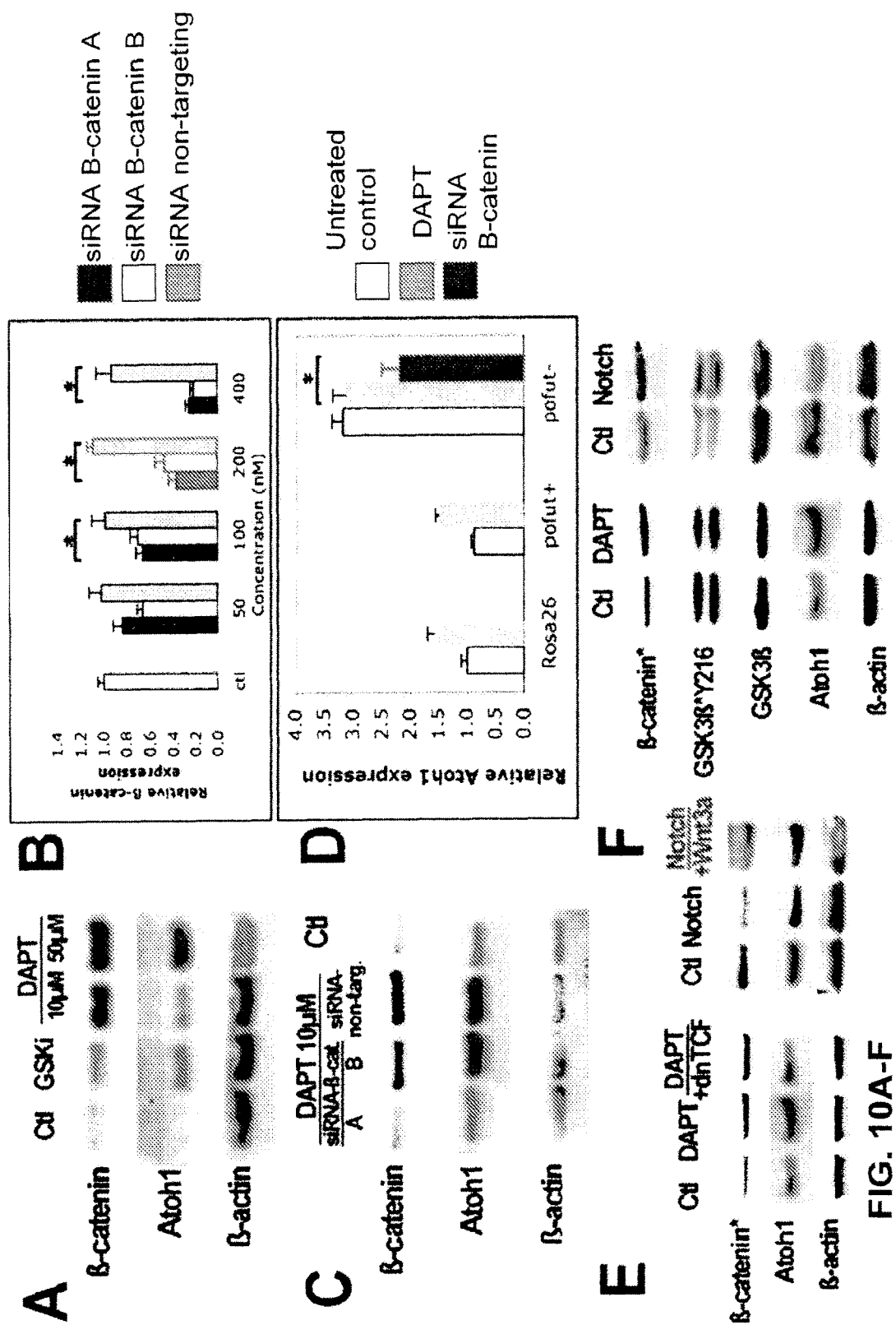
FIG. 10A-F

SEQUENCE LISTING

<160> NUMBER OF SEQ ID NOS: 41

<210> SEQ ID NO 1
<211> LENGTH: 6
<212> TYPE: DNA
<213> ORGANISM: Artificial Sequence
<220> FEATURE:
<223> OTHER INFORMATION: synthetically generated oligonucleotides
<220> FEATURE:
<221> NAME/KEY: misc_feature
<222> LOCATION: 3, 4
<223> OTHER INFORMATION: n = A,T,C or G

<400> SEQUENCE: 1 canntg                                                                    6

<210> SEQ ID NO 2
<211> LENGTH: 21
<212> TYPE: DNA
<213> ORGANISM: Artificial Sequence
<220> FEATURE:
<223> OTHER INFORMATION: synthetically generated oligonucleotides

<400> SEQUENCE: 2
gcgcaatgtt atcccgtcgt t                                                  21

<210> SEQ ID NO 3
<211> LENGTH: 22
<212> TYPE: DNA
<213> ORGANISM: Artificial Sequence
<220> FEATURE:
<223> OTHER INFORMATION: synthetically generated oligonucleotides

<400> SEQUENCE: 3
aaaattcccc gtcgcttctg tg                                                 22

<210> SEQ ID NO 4
<211> LENGTH: 21
<212> TYPE: DNA
<213> ORGANISM: Artificial Sequence
<220> FEATURE:
<223> OTHER INFORMATION: synthetically generated oligonucleotides

<400> SEQUENCE: 4
cttttaactc tggtaaagtg g                                                  21

<210> SEQ ID NO 5
<211> LENGTH: 21
<212> TYPE: DNA
<213> ORGANISM: Artificial Sequence
<220> FEATURE:
<223> OTHER INFORMATION: synthetically generated oligonucleotides

<400> SEQUENCE: 5
ttttggctcc cccctgcaaa t                                                  21

<210> SEQ ID NO 6
<211> LENGTH: 22
<212> TYPE: DNA
<213> ORGANISM: Artificial Sequence
<220> FEATURE:
<223> OTHER INFORMATION: synthetically generated oligonucleotides

<400> SEQUENCE: 6
agatctacat caacgctctg tc                                                 22

```
<210> SEQ ID NO 7
<211> LENGTH: 22
<212> TYPE: DNA
<213> ORGANISM: Artificial Sequence
<220> FEATURE:
<223> OTHER INFORMATION: synthetically generated oligonucleotides

<400> SEQUENCE: 7
actggcctca tcagagtcac tg                                              22

<210> SEQ ID NO 8
<211> LENGTH: 23
<212> TYPE: DNA
<213> ORGANISM: Artificial Sequence
<220> FEATURE:
<223> OTHER INFORMATION: synthetically generated oligonucleotides

<400> SEQUENCE: 8
atgcgctccc ctcagatggt gtc                                             23

<210> SEQ ID NO 9
<211> LENGTH: 24
<212> TYPE: DNA
<213> ORGANISM: Artificial Sequence
<220> FEATURE:
<223> OTHER INFORMATION: synthetically generated oligonucleotides

<400> SEQUENCE: 9
tcgcggtggt gagaaaggtt gtgc                                            24

<210> SEQ ID NO 10
<211> LENGTH: 18
<212> TYPE: DNA
<213> ORGANISM: Artificial Sequence
<220> FEATURE:
<223> OTHER INFORMATION: synthetically generated oligonucleotides

<400> SEQUENCE: 10
aacgggaagc ccatcacc                                                   18

<210> SEQ ID NO 11
<211> LENGTH: 24
<212> TYPE: DNA
<213> ORGANISM: Artificial Sequence
<220> FEATURE:
<223> OTHER INFORMATION: synthetically generated oligonucleotides

<400> SEQUENCE: 11
tcgcggtggt gagaaaggtt gtgc                                            24

<210> SEQ ID NO 12
<211> LENGTH: 21
<212> TYPE: DNA
<213> ORGANISM: Artificial Sequence
<220> FEATURE:
<223> OTHER INFORMATION: synthetically generated oligonucleotides

<400> SEQUENCE: 12
gcgcaatgtt atcccgtcgt t                                               21

<210> SEQ ID NO 13
<211> LENGTH: 22
<212> TYPE: DNA
<213> ORGANISM: Artificial Sequence
<220> FEATURE:
<223> OTHER INFORMATION: synthetically generated oligonucleotides
```

```
<400> SEQUENCE: 13
aaaattcccc gtcgcttctg tg                                              22

<210> SEQ ID NO 14
<211> LENGTH: 21
<212> TYPE: DNA
<213> ORGANISM: Artificial Sequence
<220> FEATURE:
<223> OTHER INFORMATION: synthetically generated oligonucleotides

<400> SEQUENCE: 14
cttttaactc tggtaaagtg g                                               21

<210> SEQ ID NO 15
<211> LENGTH: 21
<212> TYPE: DNA
<213> ORGANISM: Artificial Sequence
<220> FEATURE:
<223> OTHER INFORMATION: synthetically generated oligonucleotides

<400> SEQUENCE: 15
ttttggctcc ccctgcaaa t                                                21

<210> SEQ ID NO 16
<211> LENGTH: 38
<212> TYPE: RNA
<213> ORGANISM: Artificial Sequence
<220> FEATURE:
<223> OTHER INFORMATION: synthetically generated oligonucleotides

<400> SEQUENCE: 16
gcaacguuau cccguccuuu aacagcgaug auggcaca                             38

<210> SEQ ID NO 17
<211> LENGTH: 42
<212> TYPE: RNA
<213> ORGANISM: Artificial Sequence
<220> FEATURE:
<223> OTHER INFORMATION: synthetically generated oligonucleotides

<400> SEQUENCE: 17
gcgcuuggcu gaaccaucau ugugaaauuc uuggcuauua uu                        42

<210> SEQ ID NO 18
<211> LENGTH: 22
<212> TYPE: DNA
<213> ORGANISM: Artificial Sequence
<220> FEATURE:
<223> OTHER INFORMATION: synthetically generated oligonucleotides

<400> SEQUENCE: 18
ggggagaggc aggggaggag ag                                              22

<210> SEQ ID NO 19
<211> LENGTH: 19
<212> TYPE: DNA
<213> ORGANISM: Artificial Sequence
<220> FEATURE:
<223> OTHER INFORMATION: synthetically generated oligonucleotides

<400> SEQUENCE: 19
aggccgggga gggtgacga                                                  19

<210> SEQ ID NO 20
<211> LENGTH: 20
```

```
<212> TYPE: DNA
<213> ORGANISM: Artificial Sequence
<220> FEATURE:
<223> OTHER INFORMATION: synthetically generated oligonucleotides

<400> SEQUENCE: 20
acgtttggca gctccctctc                                                    20

<210> SEQ ID NO 21
<211> LENGTH: 22
<212> TYPE: DNA
<213> ORGANISM: Artificial Sequence
<220> FEATURE:
<223> OTHER INFORMATION: synthetically generated oligonucleotides

<400> SEQUENCE: 21
atagttgatg cctttggtag ta                                                 22

<210> SEQ ID NO 22
<211> LENGTH: 21
<212> TYPE: DNA
<213> ORGANISM: Artificial Sequence
<220> FEATURE:
<223> OTHER INFORMATION: synthetically generated oligonucleotides

<400> SEQUENCE: 22
attccccata tgccagacca c                                                  21

<210> SEQ ID NO 23
<211> LENGTH: 24
<212> TYPE: DNA
<213> ORGANISM: Artificial Sequence
<220> FEATURE:
<223> OTHER INFORMATION: synthetically generated oligonucleotides

<400> SEQUENCE: 23
ggcaaagaca gaatataaaa caag                                               24

<210> SEQ ID NO 24
<211> LENGTH: 18
<212> TYPE: DNA
<213> ORGANISM: Artificial Sequence
<220> FEATURE:
<223> OTHER INFORMATION: synthetically generated oligonucleotides

<400> SEQUENCE: 24
aatcgggtta gttctttg                                                      18

<210> SEQ ID NO 25
<211> LENGTH: 21
<212> TYPE: DNA
<213> ORGANISM: Artificial Sequence
<220> FEATURE:
<223> OTHER INFORMATION: synthetically generated oligonucleotides

<400> SEQUENCE: 25 actcccoctc cctttctggt a                                                  21

<210> SEQ ID NO 26
<211> LENGTH: 19
<212> TYPE: DNA
<213> ORGANISM: Artificial Sequence
<220> FEATURE:
<223> OTHER INFORMATION: synthetically generated oligonucleotides

<400> SEQUENCE: 26
``` caggggagc tgaaggaag                                                    19

<210> SEQ ID NO 27
<211> LENGTH: 23
<212> TYPE: DNA
<213> ORGANISM: Artificial Sequence
<220> FEATURE:
<223> OTHER INFORMATION: synthetically generated oligonucleotides

<400> SEQUENCE: 27
ttttaagtta gcagaggaga tta                                              23

<210> SEQ ID NO 28
<211> LENGTH: 23
<212> TYPE: DNA
<213> ORGANISM: Artificial Sequence
<220> FEATURE:
<223> OTHER INFORMATION: synthetically generated oligonucleotides

<400> SEQUENCE: 28
ctgagcccca aagttgtaat gtt                                              23

<210> SEQ ID NO 29
<211> LENGTH: 21
<212> TYPE: DNA
<213> ORGANISM: Artificial Sequence
<220> FEATURE:
<223> OTHER INFORMATION: synthetically generated oligonucleotides

<400> SEQUENCE: 29
tggggtgcag agaagactaa a                                                21

<210> SEQ ID NO 30
<211> LENGTH: 20
<212> TYPE: DNA
<213> ORGANISM: Artificial Sequence
<220> FEATURE:
<223> OTHER INFORMATION: synthetically generated oligonucleotides

<400> SEQUENCE: 30
accccaggcc tagtgtctcc                                                  20

<210> SEQ ID NO 31
<211> LENGTH: 21
<212> TYPE: DNA
<213> ORGANISM: Artificial Sequence
<220> FEATURE:
<223> OTHER INFORMATION: synthetically generated oligonucleotides

<400> SEQUENCE: 31
tgccagcccc tctattgtca g                                                21

<210> SEQ ID NO 32
<211> LENGTH: 24
<212> TYPE: DNA
<213> ORGANISM: Artificial Sequence
<220> FEATURE:
<223> OTHER INFORMATION: synthetically generated oligonucleotides

<400> SEQUENCE: 32
gtgggggtag tttgccgtaa tgtg                                             24

<210> SEQ ID NO 33
<211> LENGTH: 24
<212> TYPE: DNA
<213> ORGANISM: Artificial Sequence

```
<220> FEATURE:
<223> OTHER INFORMATION: synthetically generated oligonucleotides

<400> SEQUENCE: 33
ggctctggct tctgtaaact ctgc                                          24

<210> SEQ ID NO 34
<211> LENGTH: 30
<212> TYPE: DNA
<213> ORGANISM: Artificial Sequence
<220> FEATURE:
<223> OTHER INFORMATION: synthetically generated oligonucleotides

<400> SEQUENCE: 34
atcacccaaa caaacaaaga gtcagaactt                                    30

<210> SEQ ID NO 35
<211> LENGTH: 30
<212> TYPE: DNA
<213> ORGANISM: Artificial Sequence
<220> FEATURE:
<223> OTHER INFORMATION: synthetically generated oligonucleotides

<400> SEQUENCE: 35
gttaggagcc agaagcaaag ggggtgacac                                    30

<210> SEQ ID NO 36
<211> LENGTH: 30
<212> TYPE: DNA
<213> ORGANISM: Artificial Sequence
<220> FEATURE:
<223> OTHER INFORMATION: synthetically generated oligonucleotides

<400> SEQUENCE: 36
atcacccaaa cacatacgaa gtcagaactt                                    30

<210> SEQ ID NO 37
<211> LENGTH: 30
<212> TYPE: DNA
<213> ORGANISM: Artificial Sequence
<220> FEATURE:
<223> OTHER INFORMATION: synthetically generated oligonucleotides

<400> SEQUENCE: 37
gttaggagcc agaggatcgt ggggtgacac                                    30

<210> SEQ ID NO 38
<211> LENGTH: 29
<212> TYPE: DNA
<213> ORGANISM: Artificial Sequence
<220> FEATURE:
<223> OTHER INFORMATION: synthetically generated oligonucleotides

<400> SEQUENCE: 38
atcacccaaa caaacaagag tcagcactt                                     29

<210> SEQ ID NO 39
<211> LENGTH: 30
<212> TYPE: DNA
<213> ORGANISM: Artificial Sequence
<220> FEATURE:
<223> OTHER INFORMATION: synthetically generated oligonucleotides

<400> SEQUENCE: 39
gttaggagcc agaagcaaag ggggtgactc                                    30
```

```
<210> SEQ ID NO 40
<211> LENGTH: 11
<212> TYPE: PRT
<213> ORGANISM: Artificial Sequence
<220> FEATURE:
<223> OTHER INFORMATION: Synthetic Peptide L803
<220> FEATURE:
<221> NAME/KEY: VARIANT
<222> LOCATION: 10
<223> OTHER INFORMATION: Xaa = Phospho-Serine

<400> SEQUENCE: 40

Lys Glu Ala Pro Pro Ala Pro Pro Gln Xaa Pro
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic Peptide L803-mts
<220> FEATURE:
<221> NAME/KEY: VARIANT
<222> LOCATION: 1
<223> OTHER INFORMATION: Xaa = Myristoylated Glyine
<220> FEATURE:
<221> NAME/KEY: VARIANT
<222> LOCATION: 11
<223> OTHER INFORMATION: Xaa = Phospho-Serine
<220> FEATURE:
<221> NAME/KEY: VARIANT
<222> LOCATION: 12
<223> OTHER INFORMATION: Xaa = C-terminal amide

<400> SEQUENCE: 41

Xaa Lys Glu Ala Pro Pro Ala Pro Pro Gln Xaa Xaa
1               5                   10
```

PATHWAYS TO GENERATE HAIR CELLS

CLAIM OF PRIORITY

This application is the National Stage of International Application No. PCT/US2009/065747, filed Nov. 24, 2009, and claims priority under 35 USC § 119(e) to U.S. Provisional Patent Application Ser. No. 61/117,515, filed on Nov. 24, 2008. The entire contents of the foregoing applications are hereby incorporated by reference.

TECHNICAL FIELD

This disclosure relates to methods and compositions for modulating (e.g., increasing) Atoh1 activity (e.g., biological activity) and/or expression (e.g., transcription and/or translation) in vivo and/or in vitro, e.g., in a biological cell and/or in a subject. More specifically, the methods and compositions described herein can be used in the treatment of diseases and/or disorders that would benefit from increased Atoh1 expression in a biological cell.

BACKGROUND

Atonal protein homologue 1 (Atoh1 or atonal) is a proneural gene that encodes a basic helix-loop-helix (bHLH) domain-containing protein that seems to play an important role in cell fate determination in the development of the *Drosophila* nervous system (Jarman et al., *Cell,* 73:1307-1321, 1993). Atoh1 is evolutionarily conserved, with homologs identified in *Tribolium castenium* (the red flour beetle), *Fugu rubripes* (puffer fish), chicken (Cath1), mouse (Math1), and human (Hath1) (Ben-Arie et al., *Hum. Mol. Gene.,* 5:1207-1216, 1996). Each of these homologs contain a bHLH domain that is identical in length and have high sequence identity to the Atoh1 bHLH domain. For example, the Hath1 and Math1 genes are almost identical in length. These molecules also have highly similar nucleotide sequences (86% identity) and highly similar bHLH amino acid sequences (89%). The bHLH domain of Cath1 is 97% and 95% identical to the bHLH domain of Hath1 and Math1, respectively. The bHLH of Cath1 is 67% identical to the Atoh1 bHLH domain. In contrast, the bHLH domains of other *Drosophila* encoded proteins share only 40-50% sequence identity.

Each of the mammalian Atoh1 homologs function as transcription factors that activate E box (CANNTG (SEQ ID NO:1)) dependent transcription (Arie et al., supra; Akazawa et al., *J. Biol. Chem.,* 270:8730-8738, 1995) and function as critical positive regulators of cell fate determination in neural tissue and the gastrointestinal (GI) tract (Helms et al., *Development,* 125:919-928, 1998; Isaka et al., *Eur. J. Neurosci.,* 11:2582-2588, 1999; Ben-Arie et al., *Development,* 127:1039-1048, 2000). In addition, Atoh1 is critical for auditory hair cell development from inner ear progenitor cells, as demonstrated by the absence of auditory hair cells in Atoh1 knockout animals (Bermingham et al., *Science,* 284:1837-1841, 1999).

Once activated, Atoh1 transcription is self perpetuating due to the binding of Atoh1 to the Atoh1 3' enhancer (Helms et al., *Development,* 127:1185-1196, 2000), and the Atoh1 promoter is switched on in Atoh1 knockout mice (Bermingham et al., *Science,* 284:1837-1841, 1999; Tsuchiya et al., *Gastroenterology,* 132:208-220, 2007). These observation indicate that mechanisms to activate Atoh1, such as upstream regulators of Atoh1, must exist. Such upstream regulators of Atoh1 are likely to have important roles in the regulation of development in the central and peripheral nervous systems and in the intestinal epithelium, all of which rely on Atoh1 for differentiation.

SUMMARY

The present disclosure features methods and compositions for modulating (e.g., increasing) Atoh1 expression (e.g., transcription and/or translation) and/or activity (e.g., biological activity) a subject and/or target cell.

Thus, in one aspect, the invention provides methods for treating a subject who has or is at risk of developing hearing loss or vestibular dysfunction. The methods include identifying a subject who has experienced, or is at risk for developing, hearing loss or vestibular dysfunction; and administering to the ear of the subject a composition comprising one or more compounds that increase β-catenin expression or activity in a cell in the subject's ear; thereby treating the hearing loss or vestibular dysfunction in the subject.

In some embodiments, the subject has or is at risk for developing sensorineural hearing loss, auditory neuropathy, or both. In some embodiments, the subject has or is at risk for developing a vestibular dysfunction that results in dizziness, imbalance, or vertigo.

In some embodiments, the composition is administered systemically. In some embodiments, the composition is administered locally to the inner ear.

In some embodiments, the composition comprises a β-catenin polypeptide. In some embodiments, the composition comprises one or more Wnt/β-catenin pathway agonists. In some embodiments, the composition comprises one or more glycogen synthase kinase 3 β (GSK3β) inhibitors. In some embodiments, the composition comprises one or more casein kinase 1 (CK1) inhibitors.

In some embodiments, the methods further include administering an inhibitor of the Notch signaling pathway to the subject. In some embodiments, the inhibitor of the Notch signaling pathway is a gamma secretase inhibitor.

In some embodiments, the composition comprises a pharmaceutically acceptable excipient.

In another aspect, the invention provides methods for treating a subject who has or is at risk of developing hearing loss or vestibular dysfunction, the method comprising selecting a subject in need of treatment, obtaining a population of cells capable of differentiating into hair cells, contacting the population of cells in vitro with an effective amount of a composition comprising one or more compounds that increase β-catenin expression or activity for a time sufficient to induce at least some of the cells to express one or more of p27$_{kip}$, p75, S100A, Jagged-1, Prox1, myosin VIIa, atonal homolog 1 (Atoh1) or homologues thereof, α9 acetylcholine receptor, espin, parvalbumin 3 and F-actin (phalloidin), optionally purifying the population of cells, e.g., to a purity of at least 50%, 60%, 70%, 80%, 90%, or more, and administering the population of cells, or a subset thereof, to the subjects's ear.

In some embodiments, the subject has or is at risk for developing sensorineural hearing loss, auditory neuropathy, or both.

In some embodiments, the population of cells capable of differentiating into auditory hair cells includes cells selected from the group consisting of stem cells, progenitor cells, support cells, Deiters' cells, pillar cells, inner phalangeal cells, tectal cells, Hensen's cells, and germ cells.

In some embodiments, the stem cells are adult stem cells, e.g., adult stem cells are derived from the inner ear, bone marrow, mesenchyme, skin, fat, liver, muscle, or blood, or embryonic stem cells or stem cells obtained from a placenta or umbilical cord.

In some embodiments, the progenitor cells are derived from the inner ear, bone marrow, mesenchyme, skin, fat, liver, muscle, or blood.

In some embodiments, the composition comprises DNA encoding β-catenin; a β-catenin polypeptide; one or more Wnt/β-catenin pathway agonists; one or more glycogen synthase kinase 3 β (GSK3β) inhibitors; and/or one or more casein kinase 1 (CK1) inhibitors.

In some embodiments, administering the population of cells comprises (a) injecting the cells into the luminae of the cochlea, into the auditory nerve trunk in the internal auditory meatus, or into the scala tympani or (b) implanting the cells within a cochlea implant.

In some embodiments, the methods further include contacting the cells with an inhibitor of the Notch signaling pathway, e.g., a gamma secretase inhibitor, e.g., one or more of an arylsulfonamide, a dibenzazepine, a benzodiazepine, N—[N-(3,5-difluorophenacetyl)-L-alanyl]-(S)-phenylglycine t-butyl ester (DAPT), L-685,458, or MK0752.

In some embodiments, the methods further include administering to the ear of the subject a composition comprising one or more compounds capable of increasing β-catenin expression or activity in a cell in the subject's ear, e.g., DNA encoding β-catenin, a β-catenin polypeptide, one or more Wnt/β-catenin pathway agonist, one or more glycogen synthase kinase 3 β (GSK3β) inhibitors, and/or one or more casein kinase 1 (CK1) inhibitors.

In some embodiments, the methods further include administering to the ear of the subject a composition comprising one or more inhibitors of the Notch signaling pathway, e.g., a gamma secretase inhibitor.

In yet a further aspect, the invention provides methods for treating a subject who has or is at risk of developing hearing loss or vestibular dysfunction including identifying a subject who has experienced, or is at risk for developing, hearing loss or vestibular dysfunction; administering to the ear of the subject a composition comprising one or more compounds that specifically increase β-catenin expression or activity in a cell in the subject's ear; and administering an inhibitor of the Notch signaling pathway, e.g., a gamma secretase inhibitor, to the subject; thereby treating the hearing loss or vestibular dysfunction in the subject.

In some embodiments, the composition includes one or more Wnt/β-catenin pathway agonists. In some embodiments, the composition comprises one or more glycogen synthase kinase 3 β (GSK3β) inhibitors. In some embodiments, composition comprises one or more casein kinase 1 (CK1) inhibitors.

In some embodiments, the one or more CK1 inhibitors is antisense RNA or siRNA that binds specifically to CK1 mRNA In some embodiments, the composition comprises one or more proteasome inhibitors.

In some aspects, the present disclosure provides methods for treating a subject or subjects that have or are at risk of developing hearing loss or vestibular dysfunction. These methods include methods for treating hearing loss or vestibular dysfunction in the subject steps by identifying a subject who has experienced, or is at risk for developing, hearing loss or vestibular dysfunction, and administering to the ear of the subject a composition comprising one or more compounds capable of increasing β-catenin expression or activity in a cell in the subject's ear.

In another aspect, the present disclosure provides methods of treating a subject who has or is at risk of developing hearing loss or vestibular dysfunction. These methods include selecting a subject in need of treatment, obtaining a population of cells capable of differentiating into auditory hair cells, contacting the population of cells in vitro with an effective amount of a composition comprising one or more compounds capable of increasing β-catenin expression or activity for a time sufficient to induce at least some of the cells to express: (a) one or more of $p27_{kip}$, p75, S100A, Jagged-1, Prox1, myosin VIIa, atonal homolog 1 (Atoh1) or homologues thereof, α9 acetylcholine receptor, espin, parvalbumin 3 and F-actin (phalloidin); or (b) one or more of myosin VIIa, atonal homolog 1 (Atoh1) or homologues thereof, and administering the population of cells, or a subset thereof, to the subject's ear. In some embodiments, the population of cells capable of differentiating into hair cells expresses one or more of $p27_{kip}$, p75, S100A, Jagged-1, Prox1, myosin VIIa, atonal homolog 1 (Atoh1) or homologues thereof, α9 acetylcholine receptor, espin, parvalbumin 3 and F-actin (phalloidin).

In yet another aspect, the present disclosure provides methods of increasing the number of cells that express one or more of (a) $p27_{kip}$, p75, S100A, Jagged-1, Prox1, myosin VIIa, atonal homolog 1 (Atoh1) or homologues thereof, α9 acetylcholine receptor, espin, parvalbumin 3 and F-actin (phalloidin), or (b) one or more of myosin VIIa, atonal homolog 1 (Atoh1) or homologues thereof, e.g., in vitro. These methods include steps of obtaining a population of cells capable of differentiating into cells that express one or more of (a) $p27_{kip}$, p75, S100A, Jagged-1, Prox1, myosin VIIa, atonal homolog 1 (Atoh1) or homologues thereof, α9 acetylcholine receptor, espin, parvalbumin 3 and F-actin (phalloidin), or (b) one or more of myosin VIIa, atonal homolog 1 (Atoh1) or homologues thereof, and contacting the population of cells in vitro with an effective amount of a composition comprising one or more compounds capable of increasing β-catenin expression or activity for a time sufficient to increase the number of cells with the characteristics of auditory hair cells in the population of cells.

In a further aspect, the present disclosure provides a population of cells in which the number of cells that express one or more of (a) $p27_{kip}$, p75, S100A, Jagged-1, Prox1, myosin VIIa, atonal homolog 1 (Atoh1) or homologues thereof, α9 acetylcholine receptor, espin, parvalbumin 3 and F-actin (phalloidin), or (b) one or more of myosin VIIa, atonal homolog 1 (Atoh1) or homologues thereof, is increased. In some embodiments, this population of cells is obtained by obtaining a population of cells capable of differentiating into cells that express one or more of (a) $p27_{kip}$, p75, S100A, Jagged-1, Prox1, myosin VIIa, atonal homolog 1 (Atoh1) or homologues thereof, α9 acetylcholine receptor, espin, parvalbumin 3 and F-actin (phalloidin), or (b) one or more of myosin VIIa, atonal homolog 1 (Atoh1) or homologues thereof, contacting the population of cells in vitro with an effective amount of a composition comprising one or more compounds capable of increasing β-catenin expression or activity for a time sufficient to increase the number of cells with the characteristics of auditory hair cells in the population of cells.

In some embodiments, this population of cells contacted expresses one or more of p27kip, p75, A100AS100A, Jagged-1, Prox1, α9 acetylcholine receptor, espin, parvalbumin 3 and F-actin (phalloidin).

In a further aspect, the present disclosure includes kits that include a composition comprising one or more compounds capable of increasing β-catenin expression or activity and informational material. In some embodiments, the these kits include DNA encoding β-catenin.

In an additional aspect, the present disclosure provides methods of treating a subject who has or is at risk of developing hearing loss or vestibular dysfunction. Such methods include steps of identifying a subject who has experienced, or is at risk for developing, hearing loss or vestibular dysfunction, administering to the ear of the subject a composition comprising one or more compounds capable of increasing β-catenin expression or activity in a cell in the subject's ear, and administering an inhibitor of the Notch signaling pathway to the subject.

In some aspects, the subject selected for any of the methods disclosed herein is at risk for developing sensorineural hearing loss, auditory neuropathy, or both. For example, the subject is at risk for developing a vestibular dysfunction that results in dizziness, imbalance, or vertigo. Alternatively or in addition, the subject cn be a subject that has been or will be treated with an orthotoxic agent In some aspects, the methods disclosed herein effectively increases the expression of one or more of (a) nestin, sox2, musashi, Brn3c, islet 1, Pax2, $p27_{kip}$, p75, S100A, Jagged-1, Prox1, myosin VIIa, Atoh1 or homologues thereof, α9 acetylcholine receptor, espin, parvalbumin 3, and F-actin (phalloidin); (b) myosin VIIa, Atoh1 in cells in the subject's inner ear; (c) one or more of $p27_{kip}$, p75, S100A, Jagged-1, and Prox1 in cells in the subject's inner ear; (d) one or more of murine atonal gene 1 myosin VIIa, Atoh1 or homologues thereof, α9 acetylcholine receptor, espin, parvalbumin 3, and F-actin (phalloidin) in cells in the patient's inner ear.

In some aspects, any composition disclosed herein can be administered systemically, for example, using a systemic route of administration is selected from the group consisting of parenteral administration, intravenous injection, intramuscular injection, intraperitoneal injection, oral administration, lozenges, compressed tablets, pills, tablets, capsules, drops, ear drops, syrups, suspensions, emulsions, rectal administration, a rectal suppository, an enema, a vaginal suppository, a urethral suppository, transdermal administration, inhalation, nasal sprays, and administration using a catheter or pump.

In some aspects, any composition disclosed herein can be administered locally to the inner ear. For example, using injection into the luminae of the cochlea, into the auditory nerve trunk in the internal auditory meatus, and/or into the scala tympani. Such methods can also include, for example, administered to the middle, or the inner ear, or both, e.g., using a catheter or pump.

In some aspects, any composition disclosed herein can be administered by a route of administration selected from the group consisting of an intratympanic injection, an injection into the outer, middle, or inner ear, an injection through the round window of the ear, and an injection through the cochlear capsule.

In some aspects, the compositions administered in the methods disclosed herein include one or more of DNA encoding β-catenin (e.g., naked DNA encoding β-catenin, plasmid expression vectors encoding β-catenin, viral expression vectors encoding β-catenin), β-catenin polypeptides, one or more Wnt/β-catenin pathway agonists (e.g., selected from the group consisting of Wnt ligands, DSH/DVL1, 2, 3, LRP6N, WNT3A, WNT5A, and WNT3A, 5A), one or more glycogen synthase kinase 3 β (GSK3 β) inhibitors (e.g., selected from the group consisting of lithium chloride (LiCl), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl)urea (AR-A014418), indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5, 5'-dibromoindirubin; 5-nitroindirubin; 5-chloroindirubin; 5-methylindirubin, 5-bromoindirubin, 4-Benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-Dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-yl)urea (AR-A014418), H-KEAPPAPPQSpP-NH2 (L803) (SEQ ID NO: 40) and Myr-N-GKEAPPAPPQSpP-NH2 (L803-mts)(SEQ ID NO: 41)), one or more anti-sense RNA or siRNA that bind specifically to GSK3β mRNA, one or more casein kinase 1 (CK1) inhibitors (e.g., antisense RNA or siRNA that binds specifically to CK1 mRNA), one or more protease inhibitors, one or more proteasome inhibitors. The compositions and methods disclosed herein can also further include the use or administration of an inhibitor of the Notch signaling pathway (e.g., one or more of a gamma secretase inhibitor (e.g., one or more of an arylsulfonamide, a dibenzazepine, a benzodiazepine, N—[N-(3,5-difluorophenacetyl)-L-alanyl]-(S)-phenylglycine t-butyl ester (DAPT), L-685,458, or MK0752, and an inhibitory nucleic acid including small interfering RNA, an antisense oligonucleotide, and a morpholino oligo). Where an inhibitor of Notch signaling is administered, it can be administered systemically (e.g., selected from the group consisting of parenteral administration, intravenous injection, intramuscular injection, intraperitoneal injection, oral administration, lozenges, compressed tablets, pills, tablets, capsules, drops, ear drops, syrups, suspensions, emulsions, rectal administration, a rectal suppository, an enema, a vaginal suppository, a urethral suppository, transdermal administration, inhalation, nasal sprays, and administration using a catheter or pump) and or locally (e.g., locally to the ear, for example, by injection into the luminae of the cochlea, into the auditory nerve trunk in the internal auditory meatus, and/or into the scala tympani). In some aspects, the inhibitor of Notch signaling can be administered by a route of administration selected from the group consisting of an intratympanic injection, an injection into the outer, middle, or inner ear, an injection through the round window of the ear, injection through the cochlear capsule, and/or to the middle, or the inner ear, or both using a catheter or pump.

In some aspects, the methods disclosed herein include the use of single cells (i.e., an isolated cell) and/or populations of cells, wherein the cell or population of cells are capable of differentiating (e.g., can, when subjected to the methods disclosed herein, differentiate into) auditory hair cells selected from the group consisting of stem cells (e.g., adult stem cells (e.g., adult stem cells obtained from the inner ear, bone marrow, mesenchyme, skin, fat, liver, muscle, or blood of a subject, e.g., the subject to be treated), embryonic stem cells, or stem cells obtained from a placenta or umbilical cord), progenitor cells (e.g., progenitor cells derived from the inner ear, bone marrow, mesenchyme, skin, fat, liver, muscle, or blood), support cells, Deiters' cells, pillar cells, inner phalangeal cells, tectal cells, Hensen's cells, and germ cells.

Definitions

As used herein, "Atoh1" refers to any and all Atoh1-associated nucleic acid or protein sequences and includes any sequence that is orthologous or homologous to, or has significant sequence similarity to, an Atoh1 nucleic acid or amino acid sequence, respectively. The sequence can be present in any animal including mammals (e.g., humans) and insects. Examples of Atoh1 associated sequences include, but are not limited to Atoh1 (e.g., GenBank Accession Number NM_001012432.1), Hath1 (e.g., NM_005172.1), Math1 (e.g., NM_007500.4), and Cath1 (e.g., U61149.1 and AF467292.1), as well as all other synonyms that may be used to refer to this protein, e.g., atonal, atonal homolog 1, Ath1, and helix-loop-helix protein Hath1. Furthermore, multiple homologous or similar sequences can exist in an animal.

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient that can be attributed to or associated with treatment by the compositions and methods of the present invention.

The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome.

Effective amounts of one or more compounds or a pharmaceutical composition for use in the present invention include amounts that promote increased β-catenin levels (e.g., protein levels) and/or activity (e.g., biological activity) in target cells, increased β-catenin levels (e.g. protein levels) and/or activity (e.g., biological activity) in the nucleus of target cells, increased Atoh1 expression or activity, and/or that promote complete or partial differentiation of one or more cells to treat a disease that would benefit from increased Atoh1 expression, e.g., prevent or delay the onset, delay the progression, ameliorate the effects of, or generally improve the prognosis of a subject diagnosed with one or more diseases that would benefit from increased Atoh1 expression, e.g., one or more of the diseases described herein. For example, in the treatment of hearing impairment, a compound which improves hearing to any degree or arrests any symptom of hearing impairment would be therapeutically effective. A therapeutically effective amount of a compound is not required to cure a disease but will provide a treatment for a disease.

The term "subject" is used throughout the specification to describe an animal, human or non-human, to whom treatment according to the methods of the present invention is provided. Veterinary and non-veterinary applications are contemplated. The term includes, but is not limited to, birds and mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

As used herein "target cell" and "target cells" refers to a cell or cells that are capable of undergoing conversion (e.g., differentiation) to or towards a cell or cells that have characteristics of auditory hair cells. Target cells include, but are not limited to, e.g., stem cells (e.g., inner ear stem cells, adult stem cells, bone marrow derived stem cells, embryonic stem cells, mesenchymal stem cells, skin stem cells, and fat derived stem cells), progenitor cells (e.g., inner ear progenitor cells), support cells (e.g., Deiters' cells, pillar cells, inner phalangeal cells, tectal cells and Hensen's cells), support cells expressing one or more of $p27_{kip}$, p75, S100A, Jagged-1, Prox1, and/or germ cells. As described herein, prior to treatment with the methods, compounds, and compositions described herein, each of these target cells can be identified using a defined set of one or more markers (e.g., cell surface markers) that is unique to the target cell. A different set of one or more markers (e.g., cell surface markers) can also be used to identify target cells that have a partial or complete conversion (e.g., partial or complete differentiation) to or towards a cell that has characteristics of auditory hair cells or an auditory hair cell.

Target cells can be generated from stem cells isolated from a mammal, such as a mouse or human, and the cells can be embryonic stem cells or stem cells derived from mature (e.g., adult) tissue, such as the inner ear, central nervous system, blood, skin, eye or bone marrow. Unless stated otherwise, any of the methods described below for culturing stem cells and inducing differentiation into ear cells (e.g., hair cells) can be used.

As used herein, "β-catenin" refers to any and all β-catenin-associated nucleic acid or protein sequences and includes any sequence that is orthologous or homologous to, or has significant sequence similarity to, a β-catenin nucleic acid or amino acid sequence.

In some embodiments, β-catenin, as used herein, refers to β-catenin (e.g., mammalian β-catenin), α-catenin (e.g., mammalian α-catenin), γ-catenin (e.g., mammalian γ-catenin), δ-catenin (e.g., mammalian δ-catenin).

As used herein, "β-catenin modulating compounds" or simply "compounds" include any compound that can increase β-catenin levels (e.g., protein levels) and/or activity (e.g., biological activity) in target cells. Alternatively or in addition, the strategies can promote an increase in the levels (e.g. protein levels) and/or activity (e.g., biological activity) of β-catenin in the nucleus of target cells.

As used herein, the term "expression" means protein and/or nucleic acid expression and/or protein activity.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 10A, C, and E are images of gels showing the expression levels of β-catenin, Atoh1, and β-actin following treatment of cells with the γ-secretase inhibitor DAPT (used at 10 μM and 50 μM), GSK3β inhibitor, and/or siRNA targeted against β-catenin.

FIG. 10B is a bar graph showing the effect of two siRNAs directed against β-catenin as evaluated by RT-PCR.

FIG. 10D is a bar graph showing data collected using Pofut1−/− cells in which Notch signaling is inhibited.

FIG. 10F is an image of a gel showing β-catenin expression in cells following treatment with β-catenin agonists and Notch signaling inhibitors.

DETAILED DESCRIPTION

Figures 1A, 1B:
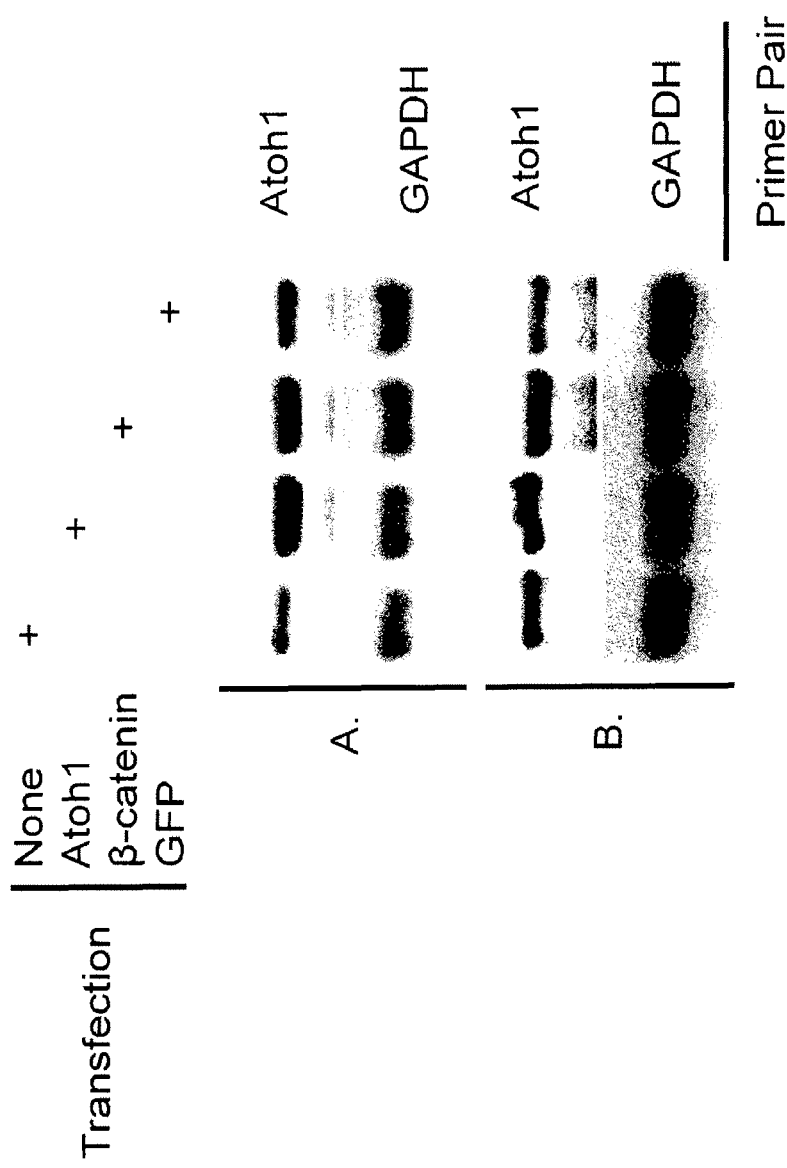
FIGS. 1A and 1B are images of an agarose gel showing Atoh1 and GAPDH mRNA expression in HEK and HT29 cells, respectively. "None" indicates that the cells were untransfected.

The present disclosure provides, inter alia, methods and pharmaceutical compositions for treating subjects for the conditions noted below. Accordingly, the present disclosure is based, at least in part, on the discovery that differentiation of a cell to or towards a mature cell of the inner ear, e.g., an auditory hair cell can be promoted through β-catenin-dependent WNT signaling. In other words, the present disclosure provides methods and compositions relating to the WNT/β-catenin signaling pathway for generating cells that have characteristics of auditory hair cells.

While the treatment methods are not limited to those in which particular underlying cellular events occur, the present compounds and compositions may increase the expression of an Atoh1 gene in a subject and/or target cell.

As shown herein, β-catenin, the intracellular mediator of the canonical Wnt signaling pathway, is capable of increasing Atoh1 expression in a biological cell. Characterization of this effect revealed that β-catenin increases Atoh1 expression through a direct interaction with two distinct β-catenin binding domains encoded in the Atoh1 3' enhancer region (e.g., at nucleotides 309-315 and nucleotides 966-972 of GenBank Accession No. AF218258 (e.g., AF218258.1; GI7677269)). These two β-catenin binding domains also interact with T-cell factor (TCF) and lymphoid enhancer-binding protein (LEF), which are transcription factors that normally maintain target genes of the WNT signaling pathway in a repressed state by interacting, in combination with other co-repressors, with the promoter or enhancer regions of Wnt target genes. Thus, the data presented herein demonstrates that β-catenin serves as an upstream regulator of Atoh1. Additionally, the data presented herein demonstrates that β-catenin dependent-Atoh1 expression promotes the differentiation of inner ear progenitor cells to or towards cells that have characteristics of auditory hair cells.

Catenins

Catenins are a group of proteins that are commonly found in complex with cadherin cell adhesion molecules, e.g., in animal cells. Four catenins have been identified to date, namely: α-catenin, (β-catenin, δ-catenin, and γ-catenin.

α-catenin is an actin-binding protein at the adherens junction, that has overall similarity to vinculin, another actin-binding protein present at adhesional complexes. α-catenin is about 100 kDa (e.g., 102 kDa) as detected by Western Blotting (see, e.g., Nagafuchi et al., Cell, 65:849-857, 1991). α-catenin is detectable by Western blotting using, e.g., anti-alpha catenin monoclonal antibody available from GenWay (e.g., catalogue number 20-272-191447).

β-catenin is capable of binding to the subdomain of some cadherins and is implicated in the WNT signaling pathway. The ability of β-catenin to bind to other proteins is regulated by tyrosine kinases and serine kinases such as GSK-3 (see, e.g., Lilien et al., Current Opinion in Cell Biology, 17:459-465, 2005). β-catenin is about a 80-100 kDa (e.g., 88 kDa-92 kDa, e.g., 92 kDa) as detected by Western Blotting. β-catenin is detectable by Western blotting using, e.g., anti-beta catenin monoclonal antibody available from Abcam (e.g., catalogue number Ab2982).

δ-catenin (e.g., δ1-catenin and δ2-catenin) is a member of a family of proteins with ten armadillo repeats (the p120 catenin subfamily of catenins). δ-catenin is expressed predominantly in neural tissue where it interacts with presenilins (see, e.g., Israely et al., Current Biology, 14:1657-1663, 2004 and Rubio et al., Mol. And Cell. Neurosci., 4:611-623, 2005). δ-catenin is about a 100-150 kDa (e.g., about 125 kDa) as detected by Western Blotting. δ1-catenin is detectable by Western blotting using, e.g., anti-delta catenin antibody available from Sigma Aldrich (e.g., catalogue number C4989). δ2-catenin is detectable by Western blotting using, e.g., anti-delta catenin antibody available from Abcam (e.g., catalogue number ab54578).

γ-catenin is commonly found as a component of desmosomes and can bind to desmoglein I (see e.g., Franke et al., Proc. Natl. Acad. Sci. U.S.A., 86:4027-31, 1989). γ-catenin is about a 80-100 kDa (e.g., about 80 kDa) as detected by Western Blotting. γ-catenin is detectable by Western blotting using, e.g., anti-gamma catenin monoclonal antibody available from Abcam (e.g., catalogue number Ab11799).

WNT/β-Catenin Signaling

The expression of bHLH transcription factors, such as Atoh1, is partly regulated by various components of the Notch pathway. However, Notch may be only a part of the complex regulatory circuits governing the timing and amount of bHLH transcription factor expression as well as the tissue specificity of expression.

WNT signaling pathways (see, e.g., FIG. 14) play a key role in early development of several tissues, including but not limited to, for example, the intestinal epithelium and the inner ear (Clevers, Cell, 127:469-480, 2006; Ohyama et al., Development, 133:865-875, 2006; Pinto et al., Exp. Cell. Res., 306:357-363, 2005; Stevens et al., Dev. Biol., 261: 149-164, 2003; van E S et al., Nat. Cell. Biol., 7:381-386, 2005; van E S et al., Nature, 435:959-963, 2005). Furthermore, disruption of Wnt signaling prevents intestinal epithelial differentiation to mature cell types accompanied by decreased Atoh1 expression (Pinto et al., supra).

WNTs are secreted cysteine-rich glycoproteins that act as short-range ligands to locally activate receptor-mediated signaling pathways. In mammals, 19 members of the WNT protein family have been identified. WNTs activate more than one signaling pathway (Veerman et al., Dev. Cell., 5:367-377, 2003) including both β-catenin-dependent and β-catenin-independent pathways. The best understood of the WNT-activated pathways, however, is the WNT/β-catenin pathway, and the list of proteins identified as being involved in the WNT/β-catenin pathway is extensive and expanding.

Wnt signaling is transduced intracellularly by the frizzled (Fzd) family of receptors (Hendrickx and Leyns, Dev. Growth Differ., 50:229-243, 2008). Activation of the WNT/β-catenin pathway leads to an increase in the post-translational stability of β-catenin. As β-catenin levels rise, it accumulates in the nucleus, where it interacts and forms a complex with DNA-bound TCF and LEF family members to activate the transcription of target genes. Conversely, in the absence of WNT signaling, β-catenin is recruited to a destruction complex containing adenomatous polyposis coli (APC) and AXIN, which together serve to facilitate the phosphorylation of β-catenin by casein kinase 1 (CK1) and then glycogen synthase kinase 3 (GSK3). This process leads to the ubiquitination and proteosomal degradation of β-catenin. As a result, in the absence of WNT signaling, cells maintain low cytoplasmic and nuclear β-catenin levels. Some β-catenin is spared from proteosomal degradation through an association with cadherins at the plasma membrane (Nelson et al., Science, 303, 1483-1487, 2004).

β-catenin expression is involved in maintaining the balance between stem cell proliferation and stem cell differentiation (Chem and Walsh, Science, 297:365-369, 2002). A role for β-catenin in the development of mouse auditory epithelia has also been described and it has been shown that β-catenin expression was linked with auditory epithelia development in mouse models (Takebayashi et al., Acta. Otolaryngol Suppl., 551:18-21, 2004). Other studies also support a role for β-catenin in promoting cell proliferation in the developing auditory epithelia of mice (Takebyashi et al., Neuroreport, 16:431-434, 2005; Warchol, *J. Neurosci.*, 22:2607-2616, 2002) and rat utricles (Kim et al., Acta. Otolaryngol Suppl., 551:22-25, 2004). A further study performed in rat embryos also reports that suppression of β-catenin using antisense technology reduced the number of cells in the otic cup, which the authors concluded demonstrated that β-catenin plays a role in cell proliferation in the otic placodes and in differentiation in acoustic neurons within the acoustic neural crest complex (Matsuda and Keino, *Anat. Embryol. (Berl)*., 202:39-48, 2000). In addition, it is reported that the Wnt/β-catenin pathway is involved in defining and maintaining the sensory/neurosensory boundaries in the cochlea duct (Stevens et al., Dev. Biol., 261:149-164, 2003). Together, previously published data indicated that β-catenin is involved in promoting stem cell proliferation, not differentiation.

Methods of Treatment

In some embodiments, the present disclosure provides novel therapeutic strategies for treating diseases that would benefit from an increase in Atoh1 expression and/or activity. In some embodiments, such strategies can promote an increase in the levels (e.g., protein levels) and/or activity (e.g., biological activity) of β-catenin in target cells, thereby promoting differentiation of a target cell to or towards a mature cell of the inner ear, e.g., an auditory hair cell. Alternatively or in addition, the strategies can promote an increase in the levels (e.g. protein levels) and/or activity (e.g., biological activity) of β-catenin in the nucleus of target cells, thereby promoting differentiation of a target cell to or towards a mature cell of the inner ear, e.g., an auditory hair cell.

In some embodiments, the methods and compositions described herein promote differentiation of target cells to or towards mature cells of the inner ear, e.g., auditory hair cells without promoting substantial cellular proliferation. In some embodiments, 0, 0.5, 1, 3, 5, 10, 15, 20, 25, 30, 40, or 50% of the target cells undergo proliferation upon treatment with the methods and compositions described herein.

Compositions and Methods for Modulating β-Catenin Expression

In some embodiments, the present disclosure includes the use of compounds, compositions (referred to collectively herein as β-catenin modulating compounds) and methods that increase the levels (e.g., protein levels) and/or activity (e.g., biological activity) of β-catenin in target cells. Exemplary β-catenin modulating compounds and methods include, but are not limited to compositions and methods for increasing β-catenin expression (e.g., transcription and/or translation) or levels (e.g., concentration) in target cells include the use of:

(i) DNA encoding β-catenin: β-catenin can be expressed using one or more expression constructs. Such expression constructs include, but are not limited to, naked DNA, viral, and non-viral expression vectors). Exemplary β-catenin nucleic acid sequences that may be usefully expressed include, but are not limited to, for example, NM_001098209 (e.g., NM_001098209.1), GI:148233337, NM_001904 (e.g., NM_001904.3), GI:148228165, NM_001098210 (e.g., NM_001098210.1), GI:148227671, NM_007614 (e.g., NM_007614.2), GI:31560726, NM_007614 (e.g., NM_007614.2), and GI:31560726.

In some embodiments, β-catenin nucleic acid can include nucleic acid encoding α-catenin (e.g., NM_001903.2), δ-catenin (e.g., NM_001085467.1 (δ1) and NM_01332.2 (K)), and γ-catenin (e.g., AY243535.1 and GI:29650758)

In some embodiments, DNA encoding β-catenin can be an unmodified wild type sequence. Alternatively, DNA encoding β-catenin can be modified using standard molecular biological techniques. For example, DNA encoding β-catenin can be altered or mutated, e.g., to increase the stability of the DNA or resulting polypeptide. Polypeptides resulting from such altered DNAs will retain the biological activity of wild type β-catenin. In some embodiments, DNA encoding β-catenin can be altered to increase nuclear translocation of the resulting polypeptide. In some embodiments, DNA encoding β-catenin can be modified using standard molecular biological techniques to include an additional DNA sequence that can encode one or more of, e.g., detectable polypeptides, signal peptides, and protease cleavage sites.

(ii) β-catenin encoding polypeptides. Exemplary useful β-catenin polypeptides include, but are not limited to, for example, NP_001091679 (e.g., NP_001091679.1), GI:148233338, NP_001895 (e.g., NP_001895.1), GI:4503131, NP_001091680 (e.g., NP_001091680.1), GI:148227672, NP_031640 (e.g., NP_031640.1), and GI:6671684. Such β-catenin encoding polypeptides can be used in combination with compositions to enhance uptake of the polypeptides into biological cells. In some embodiments, β-catenin encoding polypeptides can be mutated to include amino acid sequences that enhance uptake of the polypeptides into a biological cell. In some embodiments, β-catenin encoding polypeptides can be altered or mutated to increase the stability and/or activity of the polypeptide (e.g., β-catenin point mutants). In some embodiments, β-catenin encoding polypeptides can be altered to increase nuclear translocation of the polypeptide. In some embodiments, altered polypeptides will retain the biological activity of wild type β-catenin.

In some embodiments, useful β-catenin nucleic acid sequences and β-catenin encoding polypeptides include modified β-catenin nucleic acid sequences and β-catenin encoding polypeptides. Such modified β-catenin nucleic acid sequences and β-catenin encoding polypeptides can be nucleic acids and/or polypeptide having sequences that are substantially identical to the nucleic acid or amino acid sequences of NM_001098209 (e.g., NM_001098209.1), GI:148233337, NM_001904 (e.g., NM_001904.3), GI:148228165, NM_001098210 (e.g., NM_001098210.1), GI:148227671, NM_007614 (e.g., NM_007614.2), GI:31560726, NM_007614 (e.g., NM_007614.2), GI:31560726, NP_001091679 (e.g., NP_001091679.1), GI:148233338, NP_001895 (e.g., NP_001895.1), GI:4503131, NP_001091680 (e.g., NP_001091680.1), GI:148227672, NP_031640 (e.g., NP_031640.1), and GI:6671684. In some embodiments, useful β-catenin nucleic acid sequences can be 50%, 60%, 70%, 80%, 85%, 90%, 95%, 98%, 99%, or 100% homologous to NM_001098209 (e.g., NM_001098209.1), GI:148233337, NM_001904 (e.g., NM_001904.3), GI:148228165, NM_001098210 (e.g., NM_001098210.1), GI:148227671, NM_007614 (e.g., NM_007614.2), GI:31560726, NM_007614 (e.g., NM_007614.2), and GI:31560726. In some embodiments, useful β-catenin encoding polypeptides sequences can be 50%, 60%, 70%, 80%, 85%, 90%, 95%, 98%, 99%, or 100% homologous to NP_001091679 (e.g., NP_001091679.1), GI:148233338, NP_001895 (e.g., NP_001895.1), GI:4503131, NP_001091680 (e.g., NP_001091680.1), GI:148227672, NP_031640 (e.g., NP_031640.1), and GI:6671684. In some embodiments, molecules encoded by useful modified β-catenin nucleic acid sequences and β-catenin encoding polypeptide sequences will possess at least a portion of the activity (e.g., biological activity) of the molecules encoded by the corresponding, e.g., unmodified β-catenin nucleic acid sequences and β-catenin encoding polypeptide sequences. For example, molecules encoded by modified β-catenin nucleic acid sequences and β-catenin encoding polypeptides can retain 50%, 60%, 70%, 80%, 85%, 90%, 95%, 98%, 99%, or 100% of the activity (e.g., biological activity) of the molecules encoded by the corresponding, e.g., unmodified β-catenin nucleic acid sequences and β-catenin encoding polypeptide sequences. The methods required to assess the activity of β-catenin or a β-catenin-like molecule are described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997). Useful β-catenin encoding polypeptide sequences or polypeptide fragments can have up to about 20 (e.g., up to about 10, 5, or 3) amino acid deletions, additions, or substitutions, such as conservative substitutions, to be useful for the compositions and methods described herein. Conservative amino acid substitutions are known in the art.

(iii) Wnt/β-catenin pathway agonists. In some embodiments, β-catenin levels (e.g., protein levels) and/or activity (e.g., biological activity) can be modulated (e.g., increased) using compounds or compositions that target one or more components of the WNT/β-catenin pathway. For example, suitable compounds or compositions can target two, three, four, five or more components of the WNT/β-catenin pathway. In some embodiments, components with opposing effects on β-catenin levels (e.g., protein levels) and/or activity (e.g., biological activity) can be targeted. For example, a first component that increases β-catenin levels (e.g., protein levels) and/or activity (e.g., biological activity) can be targeted in combination with a second target that inhibits β-catenin levels (e.g., protein levels) and/or activity (e.g., biological activity). In this example, the first target would be activated and the second target would be inhibited.

Exemplary useful β-catenin pathway agonists increase β-catenin expression (e.g., transcription and/or translation), levels (e.g., concentration), or activity by acting on one or more components of the Wnt/β-catenin signaling pathway. For example, suitable Wnt/β-catenin pathway agonists can act indirectly (e.g., on upstream modulators or inhibitors of β-catenin or on components of cellular transcription machinery), by increasing the stability of β-catenin (e.g., by decreasing the degradation of β-catenin, such as through the inhibition of casein kinase 1 (CK1) and glycogen synthase kinase 3 β (GSK3β)), and/or by promoting the release of sequestered endogenous intracellular β-catenin. Exemplary Wnt/β-catenin pathway agonists include, but are not limited to, e.g., Wnt ligands, DSH/DVL1, 2, 3, LRP6ΔN, WNT3A, WNT5A, and WNT3A, 5A. Additional Wnt/β-catenin pathway activators and inhibitors are reviewed in the art (Moon et al., Nature Reviews Genetics, 5:689-699, 2004). In some embodiments, suitable Wnt/β-catenin pathway agonists can include antibodies and antigen binding fragments thereof, and peptides that bind specifically to frizzled (Fzd) family of receptors.

(iv) Kinase inhibitors, e.g., casein kinase 1 (CK1) and glycogen synthase kinase 3 β (GSK3 β) inhibitors. In some embodiments, useful kinase inhibitors can increase β-catenin levels by reducing the degradation of β-catenin. In some embodiments, exemplary useful kinase inhibitors, e.g., GSK3 β inhibitors include, but are not limited to, lithium chloride (LiCl), Purvalanol A, olomoucine, alsterpaullone, kenpaullone, benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, N-(4-Methoxybenzyl)-N'-(5-nitro-1,3-thiazol-2-yl)urea (AR-A014418), and indirubins (e.g., indirubin-5-sulfonamide; indirubin-5-sulfonic acid (2-hydroxyethyl)-amide indirubin-3'-monoxime; 5-iodo-indirubin-3'-monoxime; 5-fluoroindirubin; 5, 5'-dibromoindirubin; 5-nitroindirubin; 5-chloroindirubin; 5-methylindirubin, 5-bromoindirubin), 4-Benzyl-2-methyl-1,2,4-thiadiazolidine-3,5-dione (TDZD-8), 2-thio(3-iodobenzyl)-5-(1-pyridyl)-[1,3,4]-oxadiazole (GSK3 inhibitor II), 2,4-Dibenzyl-5-oxothiadiazolidine-3-thione (OTDZT), (2'Z,3'E)-6-Bromoindirubin-3'-oxime (BIO), α-4-Dibromoacetophenone (i.e., Tau Protein Kinase I (TPK I) Inhibitor), 2-Chloro-1-(4,5-dibromo-thiophen-2-yl)-ethanone, (vi) N-(4-Methoxybenzyl)-N'-(5-nitro-1,3-thiazol-2-yl)urea (AR-A014418), and H-KEAPPAPPQSpP-NH2 (L803) (SEQ ID NO: 40) or its cell-permeable derivative Myr-N-GKEAPPAPPQSpP-NH2 (L803-mts)(SEQ ID NO: 41). Other GSK3β inhibitors are disclosed in U.S. Pat. Nos. 6,417,185; 6,489,344; 6,608,063 and Published U.S. Applications Nos. 690497, filed Oct. 20, 2003; 468605, filed Aug. 19, 2003; 646625, filed Aug. 21, 2003; 360535, filed Feb. 6, 2003; 447031, filed May 28, 2003; and 309535 filed Dec. 3, 2002. In some embodiments, suitable kinase inhibitors can include RNAi and siRNA designed to decrease GSK3β and/or CK1 protein levels. In some embodiments, useful kinase inhibitors include FGF pathway inhibitors. In some embodiments, FGF pathway inhibitors include, for example, SU5402.

(v) Protease inhibitors and Proteasome inhibitors. In some embodiments, useful protease inhibitors can increase β-catenin levels by reducing the degradation of β-catenin. Suitable protease inhibitors are known in the art (see e.g., Shargel et al., Comprehensive Pharmacy Review, Fifth Edition, published by Lippincott Williams, and Wilkins, at, e.g., pages 373 and 872-874). In some embodiments, useful protease inhibitors can include, for example, natural protease inhibitors, synthetic protease inhibitors, antiretroviral protease inhibitors, and protease inhibitor cocktails.

In some embodiments, useful protease inhibitors can include inhibitors of the proteasome or proteasome inhibitors. Suitable proteasome inhibitors include, but are not limited to, for example, Velcade® (e.g., bortezomib, Millenium Pharmaceuticals), MG132 (Calbiochem), lactacystin (Calbiochem), and proteasome inhibitor (PSI). In some embodiments, useful protease inhibitors can include inhibitors of the ubiquitin pathway.

(vi) Any combination of (i)-(v).

(vii) Any combination of (i)-(v) in combination with an inhibitor of the Notch signaling pathway, e.g., a gamma-secretase inhibitor or inhibitory nucleic acid. Exemplary gamma secretase inhibitors include, but are not limited to, e.g., arylsulfonamides, dibenzazepines, benzodiazepines, N—[N-(3,5-difluorophenacetyl)-L-alanyl]-(S)-phenylglycine t-butyl ester (DAPT), L-685,458, or MK0752. Other exemplary Notch pathway inhibitors and methods for identifying inhibitors of the Notch signaling pathway are disclosed in, e.g., PCT/US2007/084654, U.S. P.G. Pub. No. 2005/0287127, and U.S. application Ser. No. 61/027,032.

In some embodiments, the present disclosure provides methods whereby:

(a) one or more β-catenin modulating compounds are administered to a subject, e.g., to the ear of a subject (direct therapy);

(b) one or more target cells are contacted, e.g., in vitro, with one or more β-catenin modulating compounds to promote complete or partial conversion (e.g., differentiation) of those cells to or toward a mature cell type, e.g., a hair cell.

(c) one or more target cells that have been treated according to method (b) (e.g., one or more cells resulting from method (b)) is administered to a subject, e.g., to the ear of a subject (cell therapy); and (d) methods whereby one or more target cells that have been treated according to method (b) (e.g., one or more cells resulting from method (b)) are administered to a subject in combination with one or more β-catenin modulating compounds administered to a subject, e.g., to the ear of a subject (combination therapy).

Subject Selection

It is widely accepted that although cells capable of generating hair cells are present in the inner ear, natural hair cell regeneration in the inner ear is low (Li et al., Trends Mol. Med., 10, 309-315 (2004); Li et al., Nat. Med., 9, 1293-1299 (2003); Rask-Andersen et al., Hear. Res., 203, 180-191 (2005)). As a result, lost or damaged hair cells may not be adequately replaced by natural physiological processes (e.g., cell differentiation), and a loss of hair cells occurs. In many individuals, such hair cell loss can result in, e.g., sensorineural hearing loss, hearing impairment, and imbalance disorders. Therapeutic strategies that increase the number of hair cells in the inner ear will benefit a subject with hair cell loss, e.g., with one or more of these conditions.

The importance of Atoh1 in hair cell genesis is well documented. For example, Atoh1 is required for hair cell development and the differentiation of inner ear progenitor cells to inner ear support cells and/or hair cells (Bermingham et al., Science, 284:1837-1841, 1999). In addition, adenovirus mediated Math1 overexpression in the endolymph of the mature guinea pig results in the differentiation of non-sensory cells in the mature cochlea into immature hair cells (Kawamoto et al., The Journal of Neuroscience, 23:4395-4400, 2003;). The implications of these studies are twofold. First, they demonstrate that non-sensory cells of the mature cochlea retain the ability to differentiate into sensory cells, e.g., hair cells. Second, they demonstrate that Math1 overexpression is necessary and sufficient to direct hair cell differentiation from non-sensory cells. A later study furthered these findings by demonstrating that adenovirus mediated Atoh1 overexpression induces hair cell regeneration and substantially improves hearing thresholds in an experimentally deafened animal model (Izumikawa et al., Nat. Med., 11:271-276, 2005).

In some embodiments, the methods, compounds, and compositions described herein can be used for treating subjects who have, or who are at risk for developing, an auditory disorder resulting from a loss of auditory hair cells, e.g., sensorineural hair cell loss.

Subjects with sensorineural hair cell loss experience the degeneration of cochlea hair cells, which frequently results in the loss of spiral ganglion neurons in regions of hair cell loss. Such subjects may also experience loss of supporting cells in the organ of Corti, and degeneration of the limbus, spiral ligament, and stria vascularis in the temporal bone material.

In some embodiments, the present invention can be used to treat hair cell loss and any disorder that arises as a consequence of cell loss in the ear, such as hearing impairments, deafness, and vestibular disorders, for example, by promoting differentiation (e.g., complete or partial differentiation) of one or more cells into one or more cells capable of functioning as sensory cells of the ear, e.g., hair cells.

In some embodiments, the methods include steps of selecting a subject at risk of hair cell loss and/or a subject with hair cell loss. Alternatively or in addition, the methods include steps of selecting a subject at risk of sensorineural hearing loss and/or a subject with sensorineural hearing loss. Any subject experiencing or at risk for developing hearing loss is a candidate for the treatment methods described herein. A human subject having or at risk for developing a hearing loss can hear less well than the average human being, or less well than a human before experiencing the hearing loss. For example, hearing can be diminished by at least 5, 10, 30, 50% or more.

In some embodiments, the subject can have sensorineural hearing loss, which results from damage or malfunction of the sensory part (the cochlea) or the neural part (the auditory nerve) of the ear, or conductive hearing loss, which is caused by blockage or damage in the outer and/or middle ear. Alternatively or in addition, the subject can have mixed hearing loss caused by a problem in both the conductive pathway (in the outer or middle ear) and in the nerve pathway (the inner ear). An example of a mixed hearing loss is a conductive loss due to a middle-ear infection combined with a sensorineural loss due to damage associated with aging.

In some embodiments, the subject can be deaf or have a hearing loss for any reason, or as a result of any type of event. For example, a subject can be deaf because of a genetic or congenital defect; for example, a human subject can have been deaf since birth, or can be deaf or hard-of-hearing as a result of a gradual loss of hearing due to a genetic or congenital defect. In another example, a human subject can be deaf or hard-of-hearing as a result of a traumatic event, such as a physical trauma to a structure of the ear, or a sudden loud noise, or a prolonged exposure to loud noises. For example, prolonged exposures to concert venues, airport runways, and construction areas can cause inner ear damage and subsequent hearing loss.

In some embodiments, a subject can experience chemical-induced ototoxicity, wherein ototoxins include therapeutic drugs including antineoplastic agents, salicylates, quinines, and aminoglycoside antibiotics, contaminants in foods or medicinals, and environmental or industrial pollutants.

In some embodiments, a subject can have a hearing disorder that results from aging. Alternatively or in addition, the subject can have tinnitus (characterized by ringing in the ears).

In some embodiments, a subject suitable for the treatment using the methods and β-catenin modulating compounds featured in this disclosure can include a subject having a vestibular dysfunction, including bilateral and unilateral vestibular dysfunction. Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunction can be the result of a genetic or congenital defect; an infection, such as a viral or bacterial infection; or an injury, such as a traumatic or nontraumatic injury. Vestibular dysfunction is most commonly tested by measuring individual symptoms of the disorder (e.g., vertigo, nausea, and fuzzy vision).

In some embodiments, the methods and β-catenin modulating compounds provided herein can be used prophylactically, such as to prevent hearing loss, deafness, or other auditory disorders associated with loss of inner ear function. For example, a composition containing one or more compounds can be administered with a second therapeutic, such as a therapeutic that may affect a hearing disorder. Such ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin; diuretics; salicylates such as aspirin; and certain malaria treatments such as quinine and chloroquine. For example, a human undergoing chemotherapy can be treated using compounds and methods described herein. The chemotherapeutic agent cisplatin, for example, is known to cause hearing loss. Therefore, a composition containing one or more compounds can be administered with cisplatin therapy to prevent or lessen the severity of the cisplatin side effect. Such a composition can be administered before, after and/or simultaneously with the second therapeutic agent. The two agents can be administered by different routes of administration.

In some embodiments, the treatment of auditory hair cell loss includes steps whereby one or more β-catenin modulating compounds are administered to a subject to promote the formation of auditory hair cells (e.g., an inner ear and/or outer ear hair cells) and/or increase the number of hair cells (e.g., an inner ear and/or outer ear hair cells) in the ear of a subject by promoting complete or partial hair cell differentiation from non-hair cell types naturally present in the inner ear of a subject. This method of treatment is referred to as direct therapy.

In some embodiments, the treatment of auditory hair cell loss includes steps whereby one or more target cells are contacted, e.g., in vitro, with one or more β-catenin modulating compounds to promote complete or partial differentiation of those cells to or toward a mature cell type of the inner ear, e.g., a hair cell (e.g., an inner ear and/or outer ear hair cell).

Alternatively or in addition, the methods include steps whereby one or more target cells that have been contacted with one or more β-catenin modulating compounds, e.g., in vitro, are administered to the ear (e.g., the inner ear) of the subject. This method of therapy is referred to as cell therapy.

In some embodiments, the methods include steps whereby one or more target cells that have been contacted with one or more β-catenin modulating compounds, e.g., in vitro are administered to the ear (e.g., inner ear) of a subject in combination with one or more β-catenin modulating compounds. This method of treatment is referred to as combination therapy.

In general, compounds and methods described herein can be used to generate hair cell growth in the ear and/or to increase the number of hair cells in the ear (e.g., in the inner, middle, and/or outer ear). For example, the number of hair cells in the ear can be increased about 2-, 3-, 4-, 6-, 8-, or 10-fold, or more, as compared to the number of hair cells before treatment. This new hair cell growth can effectively restore or establish at least a partial improvement in the subject's ability to hear. For example, administration of an agent can improve hearing loss by about 5, 10, 15, 20, 40, 60, 80, 100% or more.

Where appropriate, following treatment, the human can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlea hair cells, and electro-cochleography provides information about the functioning of the cochlea and the first part of the nerve pathway to the brain. In some embodiments, treatment can be continued with or without modification or can be stopped.

Routes of Administration

Direct Therapy

The route of administration will vary depending on the disease being treated. Hair cell loss, sensorineural hearing loss, and vestibular disorders can be treated using direct therapy using systemic administration and/or local administration. In some embodiments, the route of administration can be determined by a subject's health care provider or clinician, for example following an evaluation of the subject. In some embodiments, a individual subject's therapy may be customized, e.g., one or more β-catenin modulating compounds, the routes of administration, and the frequency of administration can be personalized. Alternatively, therapy may be performed using a standard course of treatment, e.g., using one or more pre-selected β-catenin modulating compounds and pre-selected routes of administration and frequency of administration.

In some embodiments, one or more β-catenin modulating compounds can be administered to a subject, e.g., a subject identified as being in need of treatment for hair cell loss, using a systemic route of administration. Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

Alternatively or in addition, one or more β-catenin modulating compounds can be administered to a subject, e.g., a subject identified as being in need of treatment for hair cell loss, using a local route of administration. Such local routes of administration include administering one or more compounds into the ear of a subject and/or the inner ear of a subject, for example, by injection and/or using a pump.

In some embodiments, one or more β-catenin modulating compounds can be injected into the ear (e.g., auricular administration), such as into the luminae of the cochlea (e.g., the Scala media, Sc vestibulae, and Sc tympani). For example, one or more β-catenin modulating compounds can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlea capsule.

In another mode of administration, one or more β-catenin modulating compounds can be administered in situ, via a catheter or pump. A catheter or pump can, for example, direct a pharmaceutical composition into the cochlea luminae or the round window of the ear. Exemplary drug delivery apparatus and methods suitable for administering one or more compounds into an ear, e.g., a human ear, are described by McKenna et al., (U.S. Publication No. 2006/0030837) and Jacobsen et al., (U.S. Pat. No. 7,206,639). In some embodiments, a catheter or pump can be positioned, e.g., in the ear (e.g., the outer, middle, and/or inner ear) of a subject during a surgical procedure. In some embodiments, a catheter or pump can be positioned, e.g., in the ear (e.g., the outer, middle, and/or inner ear) of a subject without the need for a surgical procedure.

Alternatively or in addition, one or more compounds can be administered in combination with a mechanical device such as a cochlea implant or a hearing aid, which is worn in the outer ear. An exemplary cochlea implant that is suitable for use with the present invention is described by Edge et al., (U.S. Publication No. 2007/0093878).

In some embodiments, the modes of administration described above may be combined in any order and can be simultaneous or interspersed.

Alternatively or in addition, the present invention may be administered according to any of the Food and Drug Administration approved methods, for example, as described in CDER Data Standards Manual, version number 004 (which is available at fda.give/cder/dsm/DRG/drg00301.htm).

β-catenin Expression Constructs

In some aspects, β-catenin can be expressed using expression constructs, e.g., naked DNA constructs, DNA vector based constructs, and/or viral vector and/or viral based constructs.

The present application also provides such expression constructs formulated as a pharmaceutical composition, e.g., for administration to a subject. Such pharmaceutical compositions are not limited to one expression construct and rather can include two or more expression constructs (e.g., two, three, four, five, six, seven, eight, nine, ten or more expression constructs).

Naked DNA constructs and the therapeutic use of such constructs are well known to those of skill in the art (see, e.g., Chiarella et al., *Recent Patents Anti-Infect. Drug Disc.*, 3:93-101, 2008; Gray et al., *Expert Opin. Biol. Ther.*, 8:911-922, 2008; Melman et al., *Hum. Gene Ther.*, 17:1165-1176, 2008). Typically, naked DNA constructs include one or more therapeutic nucleic acids (e.g., DNA encoding β-catenin) and a promoter sequence. A naked DNA construct can be a DNA vector, commonly referred to as pDNA. Naked DNA typically do not incorporate into chromosomal DNA. Generally, naked DNA constructs do not require, or are not used in conjunction with, the presence of lipids, polymers, or viral proteins. Such constructs may also include one or more of the non-therapeutic components described herein.

DNA vectors are known in the art and typically are circular double stranded DNA molecules. DNA vectors usually range in size from three to five kilo-base pairs (e.g., including inserted therapeutic nucleic acids). Like naked DNA, DNA vectors can be used to deliver and express one or more therapeutic proteins in target cells. DNA vectors do not incorporate into chromosomal DNA.

Generally, DNA vectors include at least one promoter sequence that allows for replication in a target cell. Uptake of a DNA vector may be facilitated (e.g., improved) by combining the DNA vector with, for example, a cationic lipid, and forming a DNA complex.

Also useful are viral vectors, which are also well known to those of skill in the art. Typically, viral vectors are double stranded circular DNA molecules that are derived from a virus. Viral vectors are typically larger in size than naked DNA and DNA vector constructs and have a greater capacity for the introduction of foreign (i.e., not virally encoded) genes. Like naked DNA and DNA vectors, viral vectors can be used to deliver and express one or more therapeutic nucleic acids in target cells. Unlike naked DNA and DNA vectors, certain viral vectors stably incorporate themselves into chromosomal DNA.

Typically, viral vectors include at least one promoter sequence that allows for replication of one or more vector encoded nucleic acids, e.g., a therapeutic nucleic acid, in a host cell. Viral vectors may optionally include one or more non-therapeutic components described herein. Advantageously, uptake of a viral vector into a target cell does not require additional components, e.g., cationic lipids. Rather, viral vectors transfect or infect cells directly upon contact with a target cell.

The approaches described herein include the use of retroviral vectors, adenovirus-derived vectors, and/or adeno-associated viral vectors as recombinant gene delivery systems for the transfer of exogenous genes in vivo, particularly into humans. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14, and other standard laboratory manuals.

The genome of an adenovirus can be manipulated such that it encodes and expresses a gene product of interest but is inactivated in terms of its ability to replicate in a normal lytic viral life cycle. See, for example, Berkner et al., BioTechniques 6:616, 1988; Rosenfeld et al., Science 252: 431-434, 1991; and Rosenfeld et al. *Cell* 68:143-155, 1992. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham, J. Virol., 57:267, 1986).

Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129, 1992). It is also one of the few viruses that may integrate its DNA into non-dividing cells, and exhibits a high frequency of stable integration (see for example Flotte et al., Am. J. Respir. Cell. Mol. Biol. 7:349-356, 1992; Samulski et al., J. Virol., 63:3822-3828, 1989; and McLaughlin et al., J. Virol., 62:1963-1973, 1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260, 1985 can be used to introduce DNA into cells. Skilled practitioners will appreciate that the use of any number of viral vectors in the presently described methods is possible.

All the molecular biological techniques required to generate an expression construct described herein are standard techniques that will be appreciated by one of skill in the art. Detailed methods may also be found, e.g., *Current Protocols in Molecular Biology*, Ausubel et al. (eds.) Greene Publishing Associates, (1989), Sections 9.10-9.14 and other standard laboratory manuals. DNA encoding altered β-catenin can be generated using, e.g., site directed mutagenesis techniques.

Polypeptides Encoding β-Catenin

Polypeptides encoding β-catenin can be generated using recombinant techniques or using chemical synthesis. Methods for generating such polypeptides, and the methods required for the purification of such polypeptides will be appreciated by one of skill in the art.

Pharmaceutical Compositions

In some embodiments, one or more β-catenin modulating compounds can be formulated as a pharmaceutical composition. Pharmaceutical compositions containing one or more β-catenin modulating compounds can be formulated according to the intended method of administration.

One or more β-catenin modulating compounds can be formulated as pharmaceutical compositions for direct administration to a subject. Pharmaceutical compositions containing one or more compounds can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In some embodiments, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral.

A pharmaceutical composition can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, *Remington's Pharmaceutical Sciences*, 18th Ed., Gennaro, ed., Mack Publishing Co., Easton, Pa., 1990.

One or more β-catenin modulating compounds can be administered, e.g., as a pharmaceutical composition, directly and/or locally by injection or through surgical placement, e.g., to the inner ear. The amount of the pharmaceutical composition may be described as the effective amount or the amount of a cell-based composition may be described as a therapeutically effective amount. Where application over a period of time is advisable or desirable, the compositions of the invention can be placed in sustained released formulations or implantable devices (e.g., a pump).

Alternatively or in addition, the pharmaceutical compositions can be formulated for systemic parenteral administration by injection, for example, by bolus injection or continuous infusion. Such formulations can be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

In addition to the formulations described previously, the compositions can also be formulated as a depot preparation. Such long acting formulations can be administered by implantation (e.g., subcutaneously). Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions formulated for systemic oral administration can take the form of tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

In some embodiments, the pharmaceutical compositions described herein can include one or more of the compounds formulated according to any of the methods described above, and one or more cells obtained to the methods described herein.

Cell Therapy

In general, the cell therapy methods described herein can be used to promote complete or partial differentiation of a cell to or towards a mature cell type of the inner ear (e.g., a hair cell) in vitro. Cells resulting from such methods can be transplanted or implanted into a subject in need of such treatment. The cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described below.

Cell Selection

Target cells suitable for use in the present invention include, but are not limited to, cells that are capable of differentiating completely or partially into a mature cell of the inner ear, e.g., a hair cell (e.g., an inner ear and/or outer ear hair cell), when contacted, e.g., in vitro, with one or more β-catenin modulating compounds. Exemplary cells that are capable of differentiating into a hair cell include, but are not limited to stem cells (e.g., inner ear stem cells, adult stem cells, bone marrow derived stem cells, embryonic stem cells, mesenchymal stem cells, skin stem cells, and fat derived stem cells), progenitor cells (e.g., inner ear progenitor cells), support cells (e.g., Deiters' cells, pillar cells, inner phalangeal cells, tectal cells and Hensen's cells), and/or germ cells. The use of stem cells for the replacement of inner ear sensory cells is described, e.g., in Li et al., (U.S. Publication No. 2005/0287127) and Li et al., (U.S. patent Ser. No. 11/953,797). The use of bone marrow derived stem cells for the replacement of inner ear sensory cells is described, e.g., in Edge et al., PCT/US2007/084654.

Such suitable cells can be identified by analyzing (e.g., qualitatively or quantitatively) the presence of one or more tissue specific genes. For example, gene expression can be detected by detecting the protein product of one or more tissue-specific genes. Protein detection techniques involve staining proteins (e.g., using cell extracts or whole cells) using antibodies against the appropriate antigen. In this case, the appropriate antigen is the protein product of the tissue-specific gene expression. Although, in principle, a first antibody (i.e., the antibody that binds the antigen) can be labeled, it is more common (and improves visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized.

Tissue-specific gene expression can also be assayed by detection of RNA transcribed from the gene. RNA detection methods include reverse transcription coupled to polymerase chain reaction (RT-PCR), Northern blot analysis, and RNAse protection assays.

Exemplary tissue specific genes that may be used to identify a stem cell (e.g., an undifferentiated cell) include, but are not limited to, e.g., nestin, sox1, sox2, or musashi, NeuroD, Atoh1, and neurogenin1. Alternatively or in addition, stem cells can be selected based on one or more of the unique properties that such cell types present in vitro. For example, in vitro, stem cells often show a distinct potential for forming spheres by proliferation of single cells. Thus, the identification and isolation of spheres can aid in the process of isolating stem cells from mature tissue for use in making differentiated cells of the inner ear. For example, stem cells can be cultured in serum free DMEM/high-glucose and F12 media (mixed 1:1), and supplemented with N2 and B27 solutions and growth factors. Growth factors such as EGF, IGF-1, and bFGF have been demonstrated to augment sphere formation in culture.

Exemplary tissue specific genes that may be used to identify a progenitor cells and/or an inner ear progenitor cell (e.g., a less than fully differentiated or partially differentiated cell) include but are not limited to, e.g., nestin, sox2, and musashi, in addition to certain inner-ear specific marker genes such as Brn3c, islet1 and Pax2

Exemplary tissue specific genes that may be used to identify fully differentiated support cells include, but are not limited to, e.g., $p27_{kip}$, p75, S100A, Jagged-1, and Prox1.

Exemplary tissue specific genes that may be used to identify fully differentiated cells capable of functioning as inner ear sensory cells) include, but are not limited to, e.g., myosin VIIa, Math1 (Atoh1), α9 acetylcholine receptor, espin, parvalbumin 3, and F-actin (phalloidin).

Alternatively or in addition, cells suspected as being fully differentiated (e.g., cells capable of functioning as inner ear sensory cells) may be subjected to physiological testing to determine whether conductance channels that would be present in mature hair cells are present and active.

Alternatively or in addition, inner ear hair cells may be distinguished from other fully differentiated cells of the inner ear (e.g., spiral ganglia) by analyzing the expression of markers that are specific to spiral ganglia, which include but are not limited to ephrinB2, ephrinB3, trkB, trkC, GATA3, and BF1. In some embodiments, cells identified as expressing one or more markers that are specific to spiral ganglia, e.g., ephrinB2, ephrinB3, trkB, trkC, GATA3, and BF1 will be isolated and removed.

In some embodiments, suitable cells can be derived from a mammal, such as a human, mouse, rat, pig, sheep, goat, or non-human primate. For example, stem cells have been identified and isolated from the mouse utricular macula (Li et al., *Nature Medicine* 9:1293-1299, 2003). The cells can also be obtained from a subject to whom they will subsequently be readministered.

In some embodiments, target cells can be isolated from the inner ear of an animal. More specifically, a suitable cells can be obtained from the cochlea organ of Corti, the modiolus (center) of the cochlea, the spiral ganglion of the cochlea, the vestibular sensory epithelia of the saccular macula, the utricular macula, or the cristae of the semicircular canals.

In some embodiments, target cells can be any cell that expresses or can express Atoh1. In some embodiments, target cells can be obtained from tissues such as bone marrow, blood, skin, or an eye. In some embodiments, target cells can be obtained from any tissue that expresses or can express Atoh1, for example, intestinal tissue, skin (e.g., Merkel's cells), and cerebellum.

In some embodiments, target cells can be obtained from a single source (e.g., the ear or a structure or tissue within the ear) or a combination of sources (e.g., the ear and one or more peripheral tissues (e.g., bone marrow, blood, skin, or an eye)).

Alternatively or in addition, methods include obtaining tissue from the inner ear of the animal, where the tissue includes at least a portion of the utricular maculae. The animal can be a mammal, such as a mouse, rat, pig, rabbit, goat, horse, cow, dog, cat, primate, or human. The isolated tissue can be suspended in a neutral buffer, such as phosphate buffered saline (PBS), and subsequently exposed to a tissue-digesting enzyme (e.g., trypsin, leupeptin, chymotrypsin, and the like) or a combination of enzymes, or a mechanical (e.g., physical) force, such as trituration, to break the tissue into smaller pieces. Alternatively, or in addition, both mechanisms of tissue disruption can be used. For example, the tissue can be incubated in about 0.05% enzyme (e.g., about 0.001%, 0.01%, 0.03%, 0.07%, or 1.0% of enzyme) for about 5, 10, 15, 20, or 30 minutes, and following incubation, the cells can be mechanically disrupted. The disrupted tissue can be passed through a device, such as a filter or bore pipette, that separates a stem cell or progenitor cell from a differentiated cell or cellular debris. The separation of the cells can include the passage of cells through a series of filters having progressively smaller pore size. For example, the filter pore size can range from about 80 μm or less, about 70 μm or less, about 60 μm or less, about 50 μm or less, about 40 μm or less, about 30 μm or less, about 35 μm or less, or about 20 μm or less.

The cells obtained may constitute an enriched population of stem cells and/or progenitor cells; isolation from all (or essentially all) differentiated cells or other cellular material within the tissue may be achieved but is not required to meet the definition of "isolated." Absolute purity is not required. The invention encompasses cells obtained by the isolation procedures described herein. The cells may be mixed with a cryoprotectant and stored or packaged into kits. Once obtained, the stem cells and/or progenitor cells can be expanded in culture.

Where a mixed population of cells is used, the proportion of stem cells within the test population can vary. For example, the population can contain few stem cells (e.g., about 1-10%) a moderate proportion of stem cells (e.g., about 10-90% (e.g., about 20, 25, 30, 40, 50, 60, 70, 75, 80, or 85% stem cells)) or many stem cells (e.g., at least 90% of the population (e.g., 92, 94, 96, 97, 98, or 99%) can be stem cells). The cells will have the potential to differentiate into a completely or partially differentiated cell of the inner ear (e.g., the cell can be a pluripotent stem cell that differentiates into a cell that expresses one or more auditory proteins). Partially differentiated cells are useful in the treatment methods (whether therapeutic or prophylactic) so long as they express a sufficient number and type of auditory-specific proteins to confer a benefit on the subject (e.g., improved hearing).

Differentiation Methods

In general, differentiation can be promoted by contacting a suitable target cell and/or cell population with one or more β-catenin modulating compounds for a time sufficient to promote complete or partial conversion (e.g., differentiation) of the target cells to or towards a mature sensory cell of the inner ear, e.g., a hair cell.

Suitable target cells, e.g., identified according to the methods described above, can be cultured in vitro. In general, standard culture methods are used in the methods described herein. Appropriate culture medium is described in the art, such as in Li et al. *Nature Medicine* 9:1293-1299, 2003. The growth medium for cultured stem cells can contain one or more or any combination of growth factors. For example, growth media can contain leukemia inhibitory factor (LIF), which prevents stem cells from differentiating.

Target cells can be separated into individual well of a culture dish and cultured. Formation of spheres (clonal floating colonies) from the isolated cells can be monitored, and the spheres can be amplified by disrupting them (e.g., by physically means) to separate the cells, and the cells can be cultured again to form additional spheres. Such cultured cells can then be contacted with one or more β-catenin modulating compounds.

Alternatively or in addition, target cells may be contacted with one or more β-catenin modulating compounds in combination with an additional induction protocol. There are a number of induction protocols known in the art for inducing differentiation of stem cells with neurogenic potential into neural progenitor cells, including growth factor treatment (e.g., treatment with EGF, FGF, and IGF, as described herein) and neurotrophin treatment (e.g., treatment with NT3 and BDNF, as described herein). Other differentiation protocols are known in the art; see, e.g., Corrales et al., *J. Neurobiol.* 66(13):1489-500 (2006); Kim et al., *Nature* 418, 50-6 (2002); Lee et al., *Nat Biotechnol* 18, 675-9 (2000); and Li et al., *Nat. Biotechnol.*, 23, 215-21 (2005).

As one example of an additional induction protocol, target cells are grown in the presence of supplemental growth factors that induce differentiation into progenitor cells. These supplemental growth factors are added to the culture medium. The type and concentration of the supplemental growth factors is be adjusted to modulate the growth characteristics of the cells (e.g., to stimulate or sensitize the cells to differentiate) and to permit the survival of the differentiated cells such as neurons, glial cells, supporting cells or hair cells.

Exemplary supplementary growth factors include, but are not limited to basic fibroblast growth factor (bFGF), insulin-like growth factor (IGF), and epidermal growth factor (EGF). Alternatively, the supplemental growth factors can include the neurotrophic factors neurotrophin-3 (NT3) and brain derived neurotrophic factor (BDNF). Concentrations of growth factors can range from about 100 ng/mL to about 0.5 ng/mL (e.g., from about 80 ng/mL to about 3 ng/mL, such as about 60 ng/mL, about 50 ng/mL, about 40 ng/mL, about 30 ng/mL, about 20 ng/mL, about 10 ng/mL, or about 5 ng/ml).

Alternatively or in addition, the medium can be exchanged for medium lacking growth factors. For example, the medium can be serum-free DMEM/high glucose and F12 media (mixed 1:1) supplemented with N2 and B27 solutions. Equivalent alternative media and nutrients can also be used. Culture conditions can be optimized using methods known in the art.

Methods for Analyzing Complete or Partial Differentiation

Target cells that have been contacted with one or more β-catenin modulating compounds can be analyzed to determine if complete of partial differentiation has occurred. Such a determination can be performed by analyzing the presence or absence of tissue specific genes, as described above (see Cell Selection). Alternatively or in addition, a hair cell can be identified by physiological testing to determine if the cells generate conductance channels characteristic of mature hair or spiral ganglion cells. Such cells can be distinguished from spiral ganglia cells using the markers described above.

Secondary assays can be used to confirm, or provide additional evidence, that a cell has differentiated into a cell of the inner ear. For example, a gene useful as a marker for identifying a cell of the inner ear can be expressed exclusively in a particular cell type (e.g., exclusively in a hair cell or exclusively in cells of the spiral ganglion), or the cell may also be expressed in a few other cell types (preferably not more than one, two, three, four, or five other cell types). For example, ephrinB1 and ephrinB2 are expressed in spiral ganglion cells, and also in retinal cells. Thus detection of ephrinB1 or ephrinB2 expression is not definitive proof that a stem cell has differentiated into a cell of the spiral ganglion. Secondary assays can be used to confirm that a cell has developed into a cell of the spiral ganglion. Such assays include detection of multiple genes known to be expressed in the suspected cell type. For example, a cell that expresses ephrinB1 and/or ephrinB2, can also be assayed for expression of one or more of GATA3, trkB, trkC, BF1, FGF10, FGF3, CSP, GFAP, and Islet1. A determination that these additional genes are expressed is additional evidence that a stem cell has differentiated into a spiral ganglion cell.

Secondary assays also include detection of the absence of gene expression or the absence of proteins that are not typically expressed in hair cells. Such negative markers include the pan-cytokeratin gene, which is not expressed in mature hair cells but is expressed in supporting cells of the inner ear (Li et al., *Nature Medicine* 9:1293-1299, 2003).

Cells that are confirmed to have undergone complete or partial differentiation towards a inner ear sensory cell, e.g., a hair cell can be transplanted or implanted into a subject.

Implantation Methods

Partially and/or fully differentiated cells, e.g., generated by the methods described above, can be transplanted or implanted, such as in the form of a cell suspension, into the ear by injection, such as into the luminae of the cochlea. Injection can be, for example, through the round window of the ear or through the bony capsule surrounding the cochlea. The cells can be injected through the round window into the auditory nerve trunk in the internal auditory meatus or into the scala tympani.

To improve the ability of transplanted or implanted cells to engraft, cells can be modified prior to differentiation. For example, the cells can be engineered to overexpress one or more anti-apoptotic genes in the progenitor or differentiated cells. The Fak tyrosine kinase or Akt genes are candidate anti-apoptotic genes that can be useful for this purpose; overexpression of FAK or Akt can prevent cell death in spiral ganglion cells and encourage engraftment when transplanted into another tissue, such as an explanted organ of Corti (see for example, Mangi et al., *Nat. Med.* 9:1195-201, 2003). Neural progenitor cells overexpressing $\alpha_v\beta_3$ integrin may have an enhanced ability to extend neurites into a tissue explant, as the integrin has been shown to mediate neurite extension from spiral ganglion neurons on laminin substrates (Aletsee et al., *Audiol. Neurootol.* 6:57-65, 2001). In another example, ephrinB2 and ephrinB3 expression can be altered, such as by silencing with RNAi or overexpression with an exogenously expressed cDNA, to modify EphA4 signaling events. Spiral ganglion neurons have been shown to be guided by signals from EphA4 that are mediated by cell surface expression of ephrin-B2 and -B3 (Brors et al., *J. Comp. Neurol.* 462:90-100, 2003). Inactivation of this guidance signal may enhance the number of neurons that reach their target in an adult inner ear. Exogenous factors such as the neurotrophins BDNF and NT3, and LIF can be added to tissue transplants to enhance the extension of neurites and their growth towards a target tissue in vivo and in ex vivo tissue cultures. Neurite extension of sensory neurons can be enhanced by the addition of neurotrophins (BDNF, NT3) and LIF (Gillespie et al., *NeuroReport* 12:275-279, 2001).

In some embodiments, the cells described herein can be used in a cochlea implant, for example, as described in Edge et al., (U.S. Publication No. 2007/0093878). A cochlea implant is an electronic device that is used to improve hearing in humans who have experienced hearing loss, particularly severe to profound hearing loss. These devices typically include an "external" and an "internal" part. The external part includes a microphone, which can be placed behind the ear, that detects sounds in the environment. The sounds are then digitized and processed by a small computer called a speech processor. The external components may be referred to as a processor unit. In addition to the microphone and speech processor, the external portion of the implant can include a power source, such as a battery and an external antenna transmitter coil. The internal part is an electronic device that is put under the skin in the vicinity of the ear and is commonly referred to as a stimulator/receiver unit (see FIG. 1). The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with the implanted antenna receiver coil provided with the stimulator/receiver unit. The communication is typically provided by a radio frequency (RF) link, but other such links have been proposed and implemented with varying degrees of success.

The implanted stimulator/receiver unit typically includes the antenna receiver coil that receives the coded signal and power from the external processor component, and a stimulator that processes the coded signal and outputs a stimulation signal to an electrode assembly, which applies the electrical stimulation directly to the auditory nerve producing a hearing sensation corresponding to the original detected sound.

An electrode connected to the electronic device is inserted into the inner ear. The electrode can be a bundle of wires that have open contacts spread along the length of the cochlea and represent different frequencies of sounds. The number of electrodes can vary from 1 to about 30 electrodes, such as about 5, 10, 15, 18, 20, 22, 24, 26, or 28 electrodes.

Combination Therapies

In some embodiments, the present invention provides methods for treating a subject with one or more compounds using the direct administration and cell therapy methods described above.

Effective Dose

Toxicity and therapeutic efficacy of the compounds and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any compound used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. A subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

Generally the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: *Remington's Pharmaceutical Sciences,* 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: Goodman & Gilman's "The Pharmacological Basis of Therapeutics", 9th Ed., Hardman et al., eds., McGraw-Hill, New York, N.Y., 1996).

Methods of Screening

In some embodiments, a candidate compound can be tested for its ability to increase β-catenin levels (e.g., protein levels) and/or activity (e.g., biological activity) in target cells and/or to promote an increase in the levels (e.g. protein levels) and/or activity (e.g., biological activity) of β-catenin in the nucleus of target cells using cells (e.g., stem cells) that have been engineered to express a β-catenin reporter construct. These engineered cells make up a reporter cell line. A reporter construct includes (1) any gene or nucleic acid sequence whose expression may be indirectly or directly detected and/or assayed; and (2) a β-catenin reporter sequence (e.g., any nucleic acid sequence whose expression is specifically correlated with β-catenin activity or expression), wherein (2) is operably linked to (1) such that (2) drives the expression of (1). S Examples of (1) include, without limitation, green fluorescent protein (GFP), α-glucuronidase (GUS), luciferase, chloramphenicol transacetylase (CAT), horseradish peroxidase (HRP), alkaline phosphatase, acetylcholinesterase and β-galactosidase. Other optional fluorescent reporter genes include but are not limited to red fluorescent protein (RFP), cyan fluorescent protein (CFP) and blue fluorescent protein (BFP), or any paired combination thereof, provided the paired proteins fluoresce at distinguishable wavelengths. Examples of a β-catenin reporter sequence include β-catenin transcriptional binding sequences (e.g., nucleic acid sequences that can be bound (e.g., specifically bound) by β-catenin, wherein binding of β-catenin to the sequence modulates expression of the sequence (e.g., a promoter sequence that can be bound by (β-catenin)). In some embodiments, a candidate compound can be assessed using the TOPflash genetic reporter system (Chemicon).

Alternatively or in addition, a reporter gene can be under control of a promoter that is active in cells of the inner ear, including progenitor cells and cells at varying degrees of differentiation, but not in stem cells. In such cases, ideally, the promoter is stably upregulated in the differentiated cells or progenitors cells to allow assessment of the partially or fully differentiated phenotype (e.g., expression of the reporter gene and further identification of genes known to be expressed in the inner ear).

Methods for Assessing β-Catenin Levels and/or Activity

β-catenin levels (e.g., protein levels) and/or activity (e.g., biological activity) in target cells and/or in the nucleus of target cells can be assessed using standard methods such as Western Blotting, reverse transcriptase polymerase chain reaction, immunocytochemistry, and genetic reporter assays, examples of each of which are provided herein. Increases in β-catenin levels (e.g., protein levels) and/or activity (e.g., biological activity) in target cells and/or in the nucleus of target cells can be assessed by comparing β-catenin levels and/or activity in a first sample or a standard with β-catenin levels and/or activity in a second sample, e.g., after treatment of the sample using a method or composition expected to increase β-catenin levels and/or activity.

Kits

The compounds and pharmaceutical compositions described herein can be provided in a kit, as can cells that have been induced to differentiate (e.g., stem cells, progenitor cells, and/or support cells that have differentiated into, for example, hair cells or hair-like cells) and/or that are capable of differentiating into hair cells. The kit can also include combinations of the compounds, pharmaceutical compositions, and cells described herein. The kit can include (a) one or more compounds, such as in a composition that includes the compound, (b) cells that have been induced to differentiate (e.g., stem cells, progenitor cells, and/or support cells that have differentiated into, for example, hair cells or hair-like cells) and/or that are capable of differentiating into hair cells, (c) informational material, and any combination of (a)-(c). The informational material can be descriptive, instructional, marketing or other material that relates to the methods described herein and/or to the use of the agent for the methods described herein. For example, the informational material relates to the use of the compound to treat a subject who has, or who is at risk for developing, a auditory hair cell loss hearing. The kits can also include paraphernalia for administering one or more compounds to a cell (in culture or in vivo) and/or for administering a cell to a patient, and any combination of the methods described herein.

In one embodiment, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In another embodiment, the informational material can include instructions to administer the pharmaceutical composition to a suitable subject, e.g., a human, e.g., a human having, or at risk for developing, auditory hair cell loss.

The informational material of the kits is not limited in its form. In many cases, the informational material (e.g., instructions) is provided in printed matter, such as in a printed text, drawing, and/or photograph, such as a label or printed sheet. However, the informational material can also be provided in other formats, such as Braille, computer readable material, video recording, or audio recording. Of course, the informational material can also be provided in any combination of formats.

In addition to the compound, the composition of the kit can include other ingredients, such as a solvent or buffer, a stabilizer, a preservative, a fragrance or other cosmetic ingredient, and/or a second agent for treating a condition or disorder described herein. Alternatively, the other ingredients can be included in the kit, but in different compositions or containers than the compound. In such embodiments, the kit can include instructions for admixing the agent and the other ingredients, or for using one or more compounds together with the other ingredients.

The kit can include one or more containers for the pharmaceutical composition. In some embodiments, the kit contains separate containers, dividers or compartments for the composition and informational material. For example, the composition can be contained in a bottle (e.g., a dropper bottle, such as for administering drops into the ear), vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the pharmaceutical composition. For example, the kit can include a plurality of syringes, ampoules, foil packets, or blister packs, each containing a single unit dose of the pharmaceutical composition. The containers of the kits can be air tight and/or waterproof, and the containers can be labeled for a particular use. For example, a container can be labeled for use to treat a hearing disorder.

As noted above, the kits optionally include a device suitable for administration of the composition (e.g., a syringe, pipette, forceps, dropper (e.g., ear dropper), swab (e.g., a cotton swab or wooden swab), or any such delivery device).

EXAMPLES

The invention is further described in the following examples, which do not limit the scope of the invention described in the claims.

An adenoviral library was employed to test the affect of a number of gene on Atoh1 expression. Preliminary data generated using this method indicated that β-catenin modulated the expression of Atoh1. To confirm and characterize these findings, β-catenin was expressed in various human and non-human cell lines and animal models as described in the subsequent Examples.

Example 1: β-Catenin Modulates Atoh1 mRNA Expression in Human Cells

Human embryonic kidney (HEK) cells and the human intestinal epithelial cell line HT29 (Human colon adenocarcinoma grade II cell line) were maintained in culture media containing Dulbecco's Modified Eagles Medium (DMEM) supplemented with 10% heat inactivated fetal calf serum (FCS), 2 mM Glutamax, penicillin (50 U/mL), and streptomycin (50 μg/mL) using standard cell culture methods. For β-catenin overexpression experiments, $10^6$ HEK and HT29 cells were seeding per 10 cm dish.

β-catenin overexpression was achieved by transfecting HEK and HT29 cells seeded as described above with 5 μg of pcDNA3 (Invitrogen) encoding human β-catenin under the control of a cytomegalovirus (CMV) promoter (Michiels et al., *Nature Biotechnology*, 20:1154-1157, 2002). Negative control cells included untransfected cells and cells transfected with 5 μg green fluorescent protein, under the control of a CMV promoter (GFP: Michiels et al., supra). Positive control cells were transfected with 5 μg of Atoh1 under the control of a CMV promoter (Lumpkin et al., *Gene Expr. Patterns*, 3:389-395, 2003). All transfections were performed using 15 μL Lipofectamine™ 2000 for four hours, according to the manufacturer's instruction (Invitrogen). At the four hour time point, the transfection solution was replaced with culture media. Cells were then cultured for a total of 24 hours before RNA extractions were performed using the RNeasy Mini kit, according to the manufacturer's instruction (Qiagen). 1 μg RNA was then subjected to reverse transcriptase polymerase chain reaction using Super-Transcript™ III and Taq DNA polymerase, according to the manufacturer's instruction (New England Biolabs), using the following primer pairs:

```
Atoh1 (human):
                                    (SEQ ID NO: 2)
Sense: 5'-GCGCAATGTTATCCCGTCGTT-3'
                                    (SEQ ID NO: 3)
Antisense: 5'-AAAATTCCCCGTCGCTTCTGTG-3'

Glyceraldehyde 3-phosphate dehydrogenase
(GAPDH-human)
                                    (SEQ ID NO: 4)
Sense: 5'-CTTTTAACTCTGGTAAAGTGG-3'
                                    (SEQ ID NO: 5)
Antisense: 5'-TTTTGGCTCCCCCCTGCAAAT-3'
```

Annealing temperatures and cycles were optimized for each primer pair. The polymerase chain reaction (PCR) products that resulted from the above Atoh1 and GAPDH primer pairs were 479 base pairs (bp) and 287 bp, respectively. PCR products were resolved and analyzed by agarose gel electrophoresis.

As shown in FIGS. 1A and 1B, β-catenin expression promoted an increase in Atoh1 mRNA expression in HEK and HT29, respectively, which was similar to the increase promoted by cells transfected with Atoh1 as a positive control in each cell line. In contrast, untransfected and GFP transfected cells did not show an increase in Atoh1 mRNA expression.

The Atoh1 upregulation observed in FIG. 1 was quantified in HEK cells using real-time PCR(RT-PCR). Briefly, cells were cultured and transfected as described above. RT-PCR primers Atoh1 and S18 were purchased from Applied Biosystems and RT-PCR was performed using a Perkin Elmer ABI PRISM™ 7700 Sequence Detector (PE Applied Biosystems). Two independent experiments were performed in triplicate and Atoh1 expression was expressed as the mean value relative to the expression of the housekeeping gene, S18.

As shown in FIG. 1B, Atoh1 expression increased in HEK cells 36.02±4.46 fold compared to untreated control cells.

Similar experiments were also performed using neural progenitor cells.

Neural progenitor cells were obtained using ROSA26 mouse embryonic stem cells (Zambrowicz et al., Proc. Natl. Acad. Sci. USA., 94:3789-3794, 1997) using the methods described in Li et al. (BMC Neurosci., 10:122, 2009). β-catenin was overexpressed as described above.

Atoh1 and β-catenin levels were determined following β-catenin overexpression by subjecting 1 µg of RNA to RT-PCR using SuperTranscript™ III and Taq DNA polymerase (New England Biolabs), as described above. GAPDH levels were assessed as control. Levels of each of the markers were assessed using the following oligonucleotide primers:

```
Atoh1:
                                        (SEQ ID NO: 6)
Sense: 5'-AGATCTACATCAACGCTCTGTC'-3'
                                        (SEQ ID NO: 7)
Antisense: 5'-ACTGGCCTCATCAGAGTCACTG-3'

β-catenin:
                                        (SEQ ID NO: 8)
Sense: 5'-ATGCGCTCCCCTCAGATGGTGTC-3'
                                        (SEQ ID NO: 9)
Antisense: 5'-TCGCGGTGGTGAGAAAGGTTGTGC-3'

GAPDH:
                                        (SEQ ID NO: 10)
Sense: 5'-AACGGGAAGCCCATCACC-3'
                                        (SEQ ID NO: 11)
Antisense: 5'-TCGCGGTGGTGAGAAAGGTTGTGC-3'
```

Figures 1C, 1D:
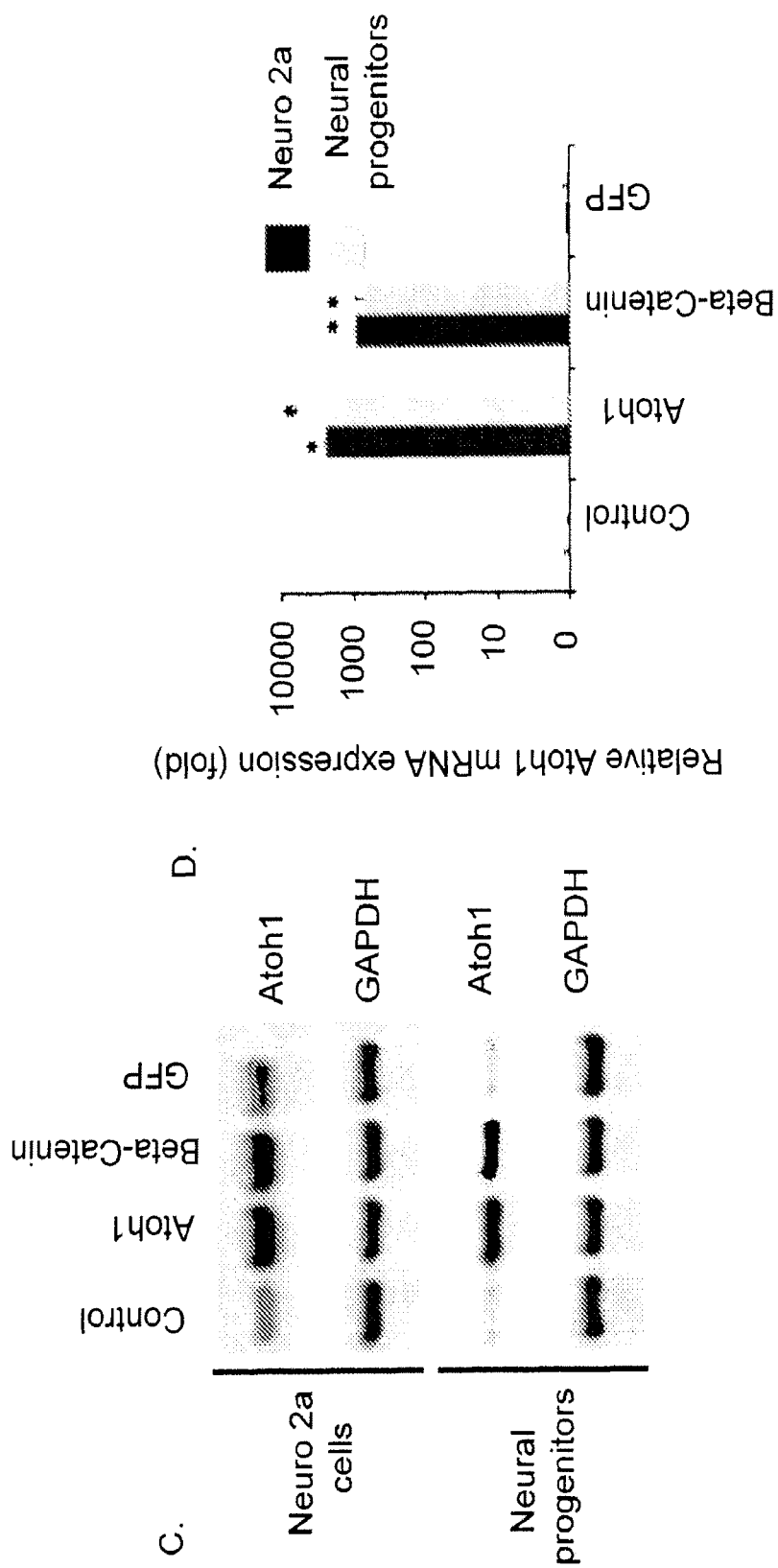
FIG. 1C is an image of a gel showing mRNA expression levels of Atoh1 and GAPDH in Neuro2a and neural progenitor cells transfected with Atoh1, β-catenin, or green fluorescent protein (GFP) (as shown).
FIGS. 1D and 1F are bar graphs showing relative Atoh1 expression as assessed by RT-PCR. Atoh1 levels were normalized against the S18 housekeeping gene.

As shown in FIGS. 1C and 1D, Atoh1 mRNA expression was upregulated in neural progenitor cells following β-catenin expression (741.2±218.2) compared to untransfected control cells or cells transfected with GFP (1±0.2). As expected, Atoh1 expression also increased following transfection with Atoh1.

These observations suggest that β-catenin increases Atoh1 mRNA expression in human cell lines.

Example 2: β-catenin Modulates Atoh1 Protein Expression in Human Cells

Atoh1 protein expression was analyzed in HEK cells transfected as described in Example 1. Following transfection, cells were cultured for 72 hours. Proteins were then resolved on 4-12% nuPAGE® Bis-Tris gels (Invitrogen) and transferred to 0.2 µm nitrocellulose membranes (BioRad). Membranes were then immunoblotted with mouse anti-Atoh1 antibody (Developmental Studies Hybridoma bank) followed by HRP-conjugated anti-mouse antibody (Sigma). Immunoblots were processed using ECL™, according to the manufacturer instructions (Amersham Pharmacia).

Figure 3:
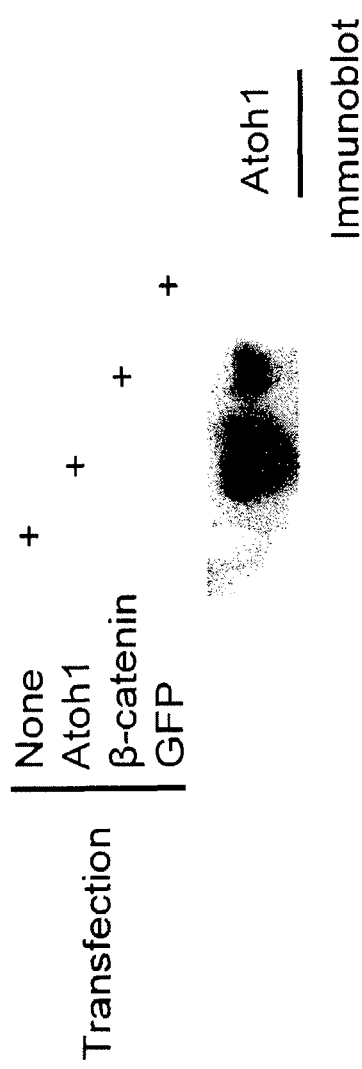
FIG. 3 is an image of an immunoblot showing Atoh1 protein expression in untransfected HEK cells and HEK cells transfected with Atoh1, β-catenin or GFP each of which was under the control of a CMV promoter.

As shown in FIG. 3, Atoh1 was not detectable in untransfected control HEK cells or GFP transfected cells. In contrast, Atoh1 was detectable in HEK cells transfected with β-catenin and Atoh1.

These observations suggest that β-catenin increases Atoh1 protein expression in human cell lines. Atoh1 expression also increased following transfection with Atoh1 possibly due to the activation of endogenous Atoh1 via an Atoh1 auto-feedback loop (Helms et al., *Development*, 127:1185-1196, 2000).

Example 3: β-catenin Modulates Atoh1 mRNA Expression in Mouse Cells

Murine Neuro2a cells and mouse neural progenitor cells derived from mouse ES cells (mES) were cultured and transfected as described in Example 1. Atoh1 and GAPDH mRNA was amplified using PCR and the following primer pairs:

```
Atoh1 (mouse)
                                        (SEQ ID NO: 12)
Sense: 5'-GCGCAATGTTATCCCGTCGTT-3'
                                        (SEQ ID NO: 13)
Antisense: 5'-AAAATTCCCCGTCGCTTCTGTG-3'

GAPDH (mouse)
                                        (SEQ ID NO: 14)
Sense: 5'-CTTTTAACTCTGGTAAAGTGG-3'
                                        (SEQ ID NO: 15)
Antisense: 5'-TTTTGGCTCCCCCCTGCAAAT-3'
```

Annealing temperatures and cycles were optimized for each primer pair. The polymerase chain reaction (PCR) products that resulted from the above Atoh1 and GAPDH primer pairs were 479 base pairs (bp) and 287 bp, respectively. PCR products were resolved and analyzed by agarose gel electrophoresis.

Figures 4A, 4B:
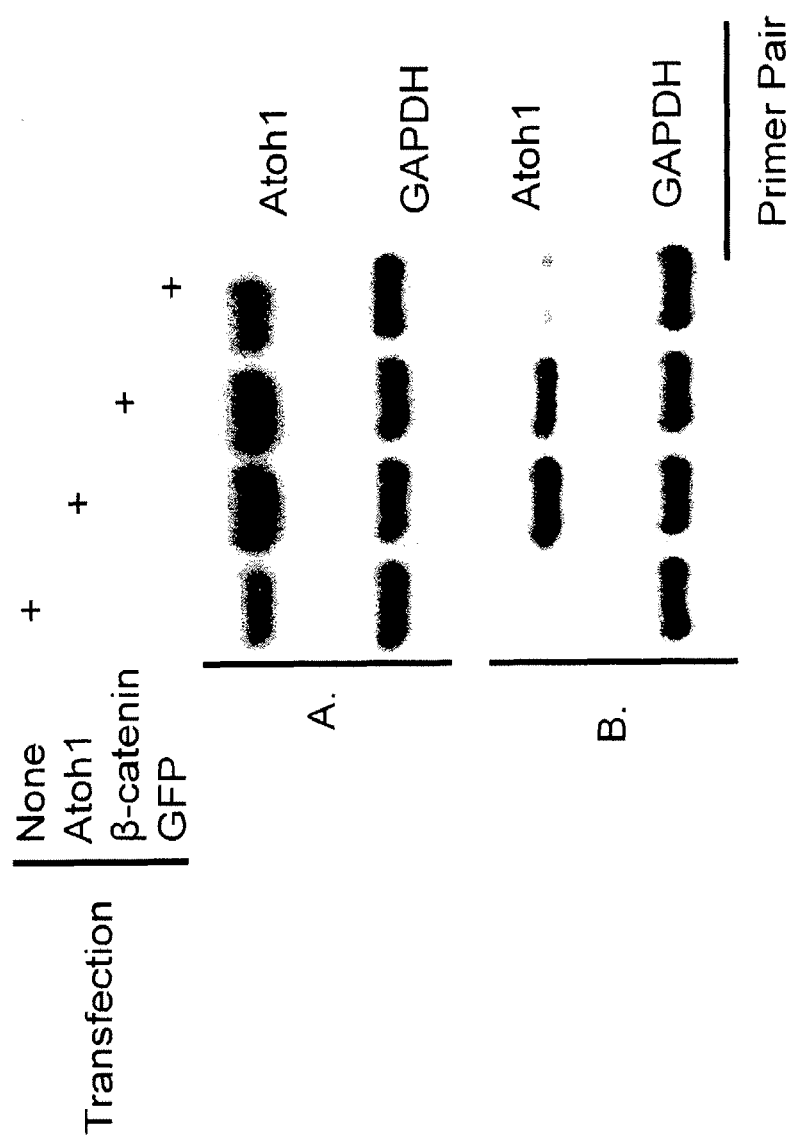
FIGS. 4A and 4B are images of an agarose gel showing Atoh1 and GAPDH mRNA expression in Neuro2a and mouse progenitor cells derived from mouse embryonic stem (ES) cells (mES), respectively. None indicates that cells are untransfected.

As shown in FIGS. 4A and 4B, β-catenin expression promoted an increase in Atoh1 mRNA expression in Neuro2a and mES cells, respectively. This increase was similar to the increase promoted by cells transfected with Atoh1 as a positive control in both cell lines. In contrast, untransfected and GFP transfected cells did not show an increase in Atoh1 mRNA expresion.

The Atoh1 upregulation observed in FIG. 4 was quantified in Neuro2a cells using real-time PCR(RT-PCR), as described in Example 1.

Figure 5:
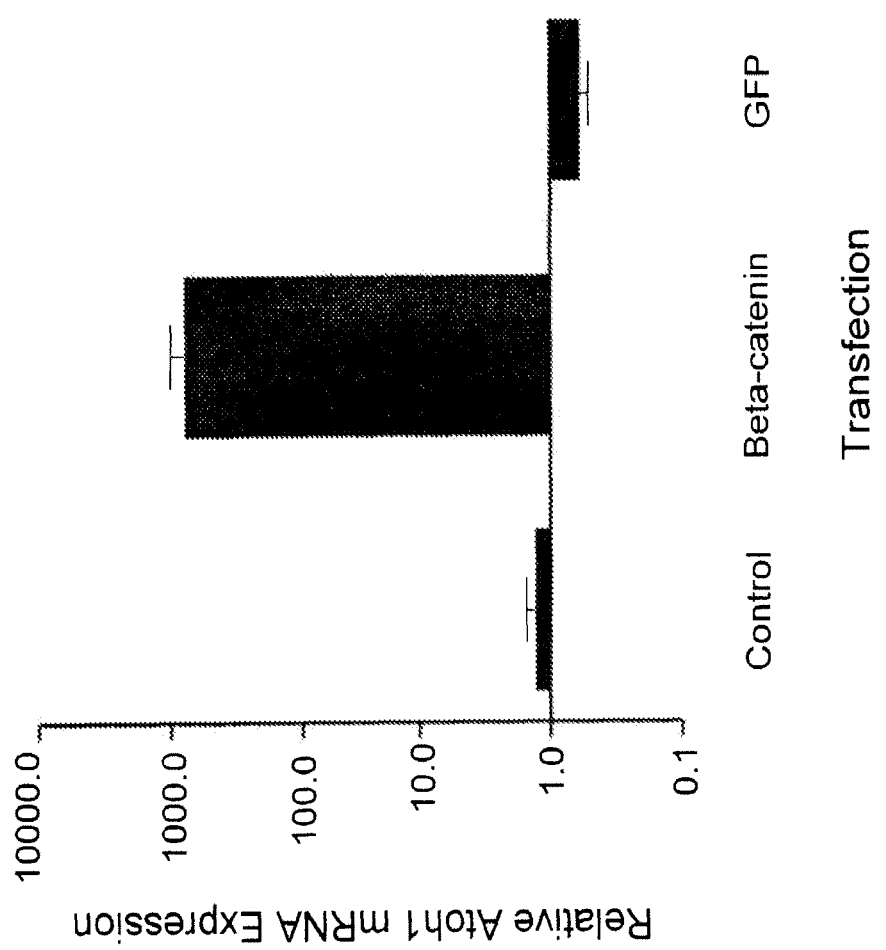
FIG. 5 is a bar graph showing Atoh1 expression in Neuro2a cells quantified using RT-PCR. Columns represent the mean of two independent experiments each performed in triplicate. Atoh1 levels are shown relative to control cells without transfection and are normalized to S18.

As shown in FIG. 5, Atoh1 expression increased in Neuro2a cells 871.86±141.31 fold compared to untreated control cells.

Neuro2a data is also shown in FIGS. 1C and 1D.

These observations suggest that β-catenin increases Atoh1 mRNA expression in murine cell lines.

The data shown in Examples 1-3 was corroborated using gene silencing. Briefly, siRNA were designed to silence Atoh1 (NM 007500.4, NM 005172.1) and β-catenin (NM_007614.2 and NM_001904.3), as shown below:
Atoh1:
GCAACGUUAUCCCGUCCUUUAACAGC-GAUGAUGGCACA (SEQ ID NO:16)
β-Catenin:
GCGCUUGGCUGAACCAUCAUUGUGAAAUUC-UUGGCUAUUAUU (SEQ ID NO:17)

200 nM of each siRNA were transfected using the GeneSilencer™ transfection reagent at 5 µL/mL. Cells were incubated in the presence of the transfection mix for 16 hours and were harvested following a total of 48 hours. Non-targetting siRNA was used as control. Gene silencing was confirmed using RT-PCR. Cells were also transfected with Atoh1, β-catenin, or GFP using the methods described above.

Figures 1E, 1F:
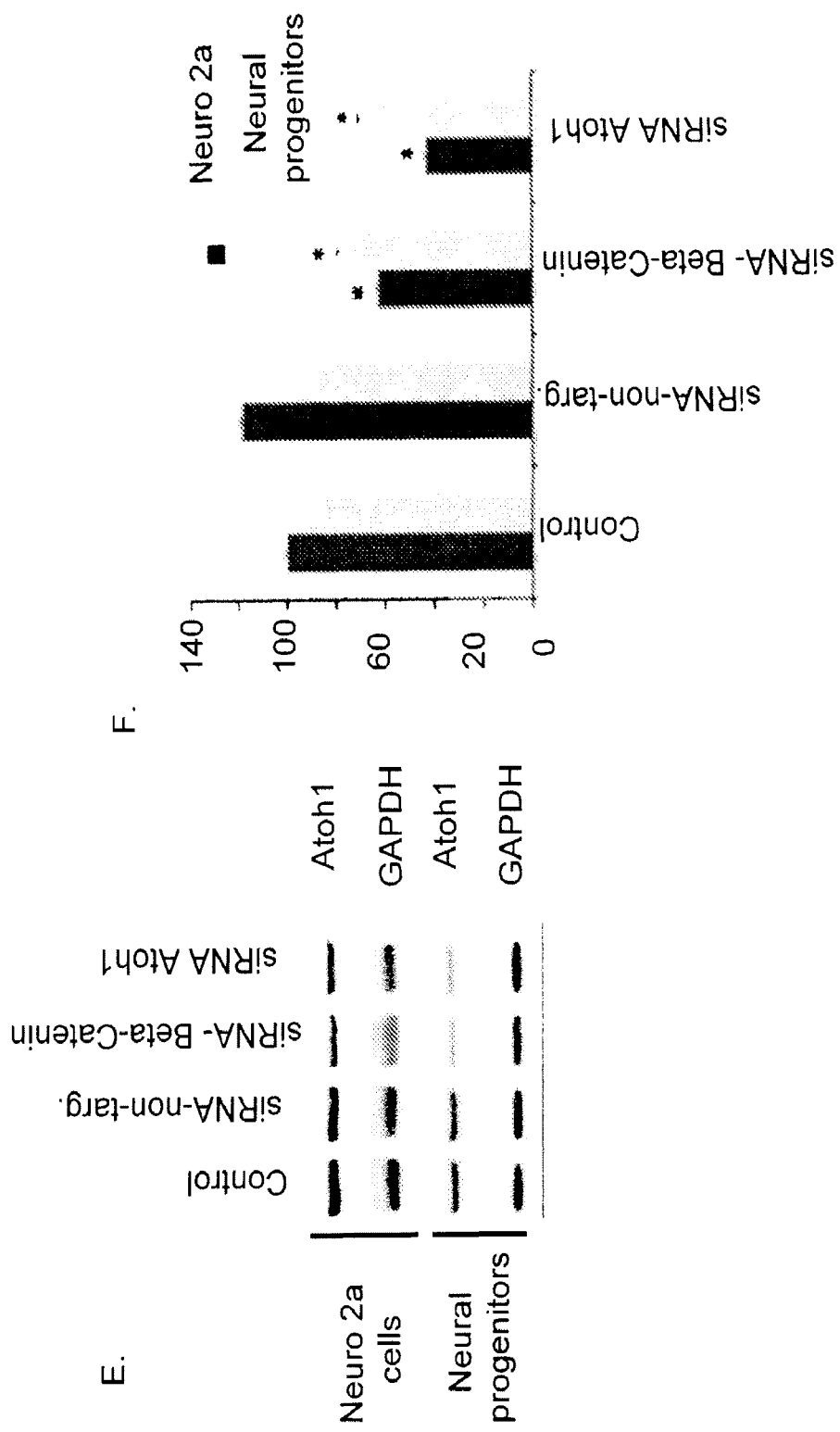
FIG. 1E is an image of a gel showing mRNA expression levels of Atoh1 and GAPDH in Neuro2a and neural progenitor cells transfected with siRNA targeted against Atoh1 or β-catenin mRNA or non-targeted siRNA as a control.

As shown in FIGS. 1E and F, Atoh1 expression was decreased by siRNA directed against Atoh1 and β-catenin in both neural progenitor cells (see Example 2) and Neuro2a (Atoh1 expression in the presence of Atoh1 siRNA decreased by about 45%. Atoh1 expression in the presence of β-catenin decreased by about 40%). β-catenin also suppressed β-catenin expression levels in all cell types tested.

The correlation between β-catenin and Atoh1 was also corroborated using genetic reporter assays. Briefly, $10^5$ Neuro2a cells were seeded into a 24-well plate one day prior to transfection. 0.125 µg of Atoh1-luciferase reporter construct and 0.125 µg o CBFl-luciferase reporter construct (Hseih et al., Mol. Cell. Biol., 16(3):952-959, 1996) TOP-Flash or FOPFlas (Addgene) or 0.125 µg of *Renilla*-luciferase were mixed in the presence or absence of 0.25 µg β-catenin and 0.5 µL lipofectamine 2000 in 0.125 mL of opti-MEM. This transfection mixture was then incubated on the cells for 4 hours. Cells were lysed after 48 hours and luciferase activity was measured using the Dual Luciferase Reporter Assay System (Promega) in a TD-20/20 Luminometer (Turner Designs).

Figures 1G, 1H:
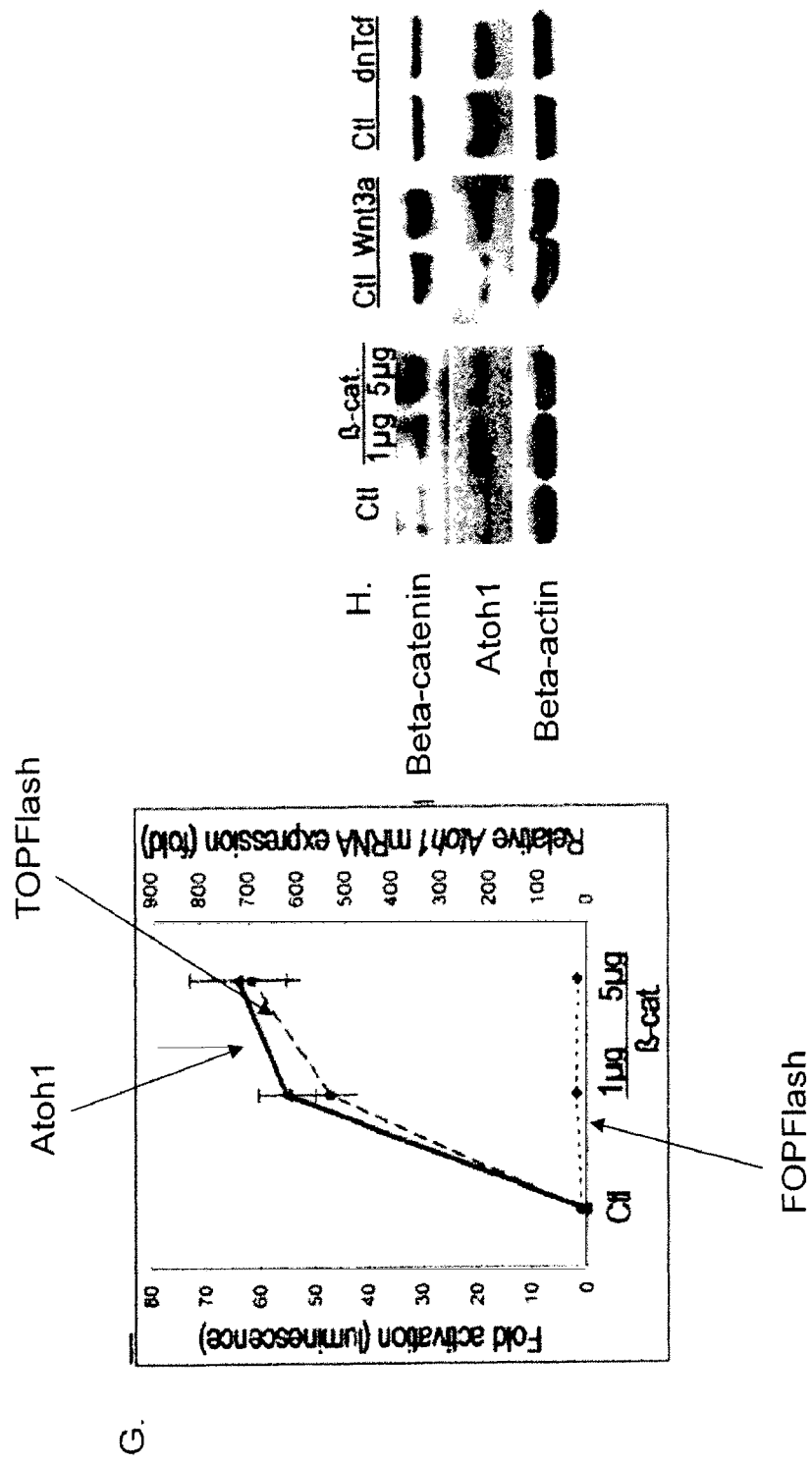
FIG. 1G is a line graph showing luciferase reporter expression levels.
FIG. 1H is an image of a Western blot gel showing Atoh1 and nuclear unphosphorylated β-catenin expression levels from the nuclear fraction.

As shown in FIGS. 1G and H, reporter activity of TOP-Flash (which contains multiple β-catenin binding sites) was comparable to reporter activity of the Atoh1 reporter, indicating that Atoh1 is regulated by β-catenin (FIG. 1G). Increased β-catenin expression also raised the level of the active fraction of nuclear β-catenin as detected using an antibody that binds specifically to the unphosphorylated form (FIG. 1H) (unphosphorylated β-catenin was detected using the anti-unphosphorylated (3-catenin antibody disclosed by van Noort et al., Blood, 110(7):2778-2779, 2007).

Nuclear unphosphorylated β-catenin and Atoh1 levels were also increased when cells were incubated in Wnt3a conditioned media (FIG. 1H). In contrast, overexpression of dominant negative Tcf4, which lacks the β-catenin binding site, decreased the level of Atoh1.

Example 4: β-catenin Directly Interacts with the Atoh1 Enhancer Region

To investigate whether β-catenin, in combination with Tcf-Lef factor, has a direct interaction with regulatory regions of the Atoh1 gene, DNA binding to β-catenin was analyzed using chromatin immunoprecipitation (ChIP).

$10^7$ HEK cells were crosslinked in DMEM containing 1% formaldehyde for 10 minutes followed by 5 minutes at 37° C. in formaldehyde saturated with 0.125 M glycine. Cross-linked cells were harvested, rinsed in phosphate buffered saline (PBS), and centrifuged for 5 minutes at 160 g at 4° C. in cold PBS. Samples were then resuspended in sonication buffer (1% Triton® X-100, 0.1% deoxycholate, 50 mM Tris pH 8.1, 150 mM NaCl, 5 mM ethylenediaminetetraacetic acid (EDTA), 2 mM phenylmethanesulphonylfluoride (PMSF), and a 1:100 dilution of fresh proteinase inhibitor cocktail (Sigma)) and genomic DNA was sheared using 15 pulses (5 seconds/pulse) in a sonication bath. Cell extracts were pelleted and resuspended in 1 ml radioimmunoprecipitation assay (RIPA) buffer supplemented with fresh proteinase inhibitors (Sigma). Each sample was then separated into one 200 µL aliquot and two 400 µL aliquots. The 200 µL aliquot was not subjected to immunoprecipitation, but was used as the input control for the subsequent PCR reaction (input). The first 400 aliquot was immunoprecipitated using mouse anti-β-catenin antibody (Upstate, 05-601) as the primary antibody at a dilution of 1:100. The second 400 µL aliquot was immunoprecipitated using nonimmune IgG as the primary antibody at a concentration of 1:6000 (Sigma, M5905). Immunoprecipitations were performed using the primary antibodies at 4° C. for 16 hours. Protein A agarose (Amersham Pharmacia) and 2 µL herrin sperm DNA (10 mg/mL) were then added to the samples for 2 hours. Immunoprecipitates were then washed and heated at 65° C. for 3 minutes in RIPA buffer. DNA was recovered from immunoprecipitates and input using ethanol precipitation and phenol extraction. Atoh1 enhancer DNA was amplified using PCR and following primer pair:

```
                                       (SEQ ID NO: 18)
Sense: 5'-GGGGAGAGGCAGGGGAGGAGAG-3'

(SEQ ID NO: 19)
Antisense: 5'-AGGCCGGGGAGGGTGACGA-3'
```

Figure 6:
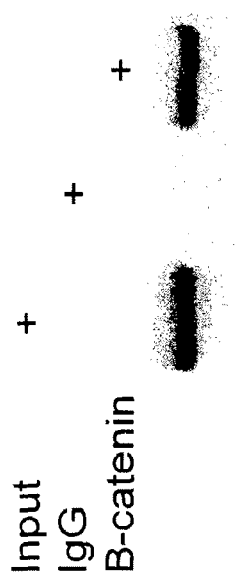
FIG. 6 is an image of an agarose gel showing Atoh1 enhancer region from HEK cells amplified using chromatin immunoprecipitation (ChIP).

Samples were then analyzed using agarose gel electrophoresis. As shown in FIG. 6, Atoh1 enhancer DNA was detected in the β-catenin precipitated samples and input samples. Atoh1 enhancer DNA was not amplified from control chromatin immunoprecipitated with nonimmune IgG These observations suggest that β-catenin binds directly to the Atoh1 enhancer.

Similar chromatin immunoprecipitation experiments were also performed using Neuro2a cells. Such methods are as described above except that harvested cells were pelleted for 10 minutes at 720 g at 4° C. Nuclei were then released in a Dounce homogenizer in PBS containing protease inhibitors (see above) and collected at 4° C. by centrifugation at 2400 g. Sheared chromatin was collected in the supernatant by centrifugation (8,000 g at 4° C. for 10 minutes) after treatment of the nuclei with the enzymatic cocktail from the ChIP-IT™ Express kit (Active Motif) for 10 minutes at 37° C. 1 µg of sheared DNA was used for immunoprecipitation using 1 µg of mouse anti-β-catenin antibody (Upstate, 05-601, 1:100), mouse anti-LEF-1 antibody (Sigma L7901) or nonimmune mouse serum (Sigma). Precipitated chromatin was recovered after reversing cross-links and the proteins were digested with proteinase K. Target Atoh1 regulatory DNA (AF218258) was amplified by PCR using the following primers, which cover the entire 1.3 kB sequence in overlapping segments (as indicated)

```
Sense 1 (nucleotides 33-272):
ACGTTTGGCAGCTCCCTCTC         (SEQ ID NO: 20)

Anti-sense 1:
ATAGTTGATGCCTTTGGTAGTA       (SEQ ID NO: 21)

Sense 2 (nucleotides 148-434):
ATTCCCCATATGCCAGACCAC        (SEQ ID NO: 22)

Anti-sense 2:
GGCAAAGACAGAATATAAAACAAG     (SEQ ID NO: 23)

Sense 3 (nucleotides 349-609):
AATCGGGTTAGTTCTTTG           (SEQ ID NO: 24)

Antisense 3:
ACTCCCCCTCCCTTTCTGGTA        (SEQ ID NO: 25)

Sense 4 (nucleotides 501-742):
CAGGGGGAGCTGAAGGAAG          (SEQ ID NO: 26)

Anti-sense 4:
TTTTAAGTTAGCAGAGGAGATTA      (SEQ ID NO: 27)

Sense 5 (nucleotides 675-939):
CTGAGCCCCAAAGTTGTAATGTT      (SEQ ID NO: 28)

Anti-sense 5:
TGGGGTGCAGAGAAGACTAAA        (SEQ ID NO: 29)

Sense 6 (nucleotides 926-1161):
ACCCCAGGCCTAGTGTCTCC         (SEQ ID NO: 30)

Anti-sense 6:
TGCCAGCCCCTCTATTGTCAG        (SEQ ID NO: 31)

Sense 7 (nucleotides 1094-1367):
GTGGGGGTAGTTTGCCGTAATGTG     (SEQ ID NO: 32)

Anti-sense 7:
GGCTCTGGCTTCTGTAAACTCTGC     (SEQ ID NO: 33)
```

Figure 2A:
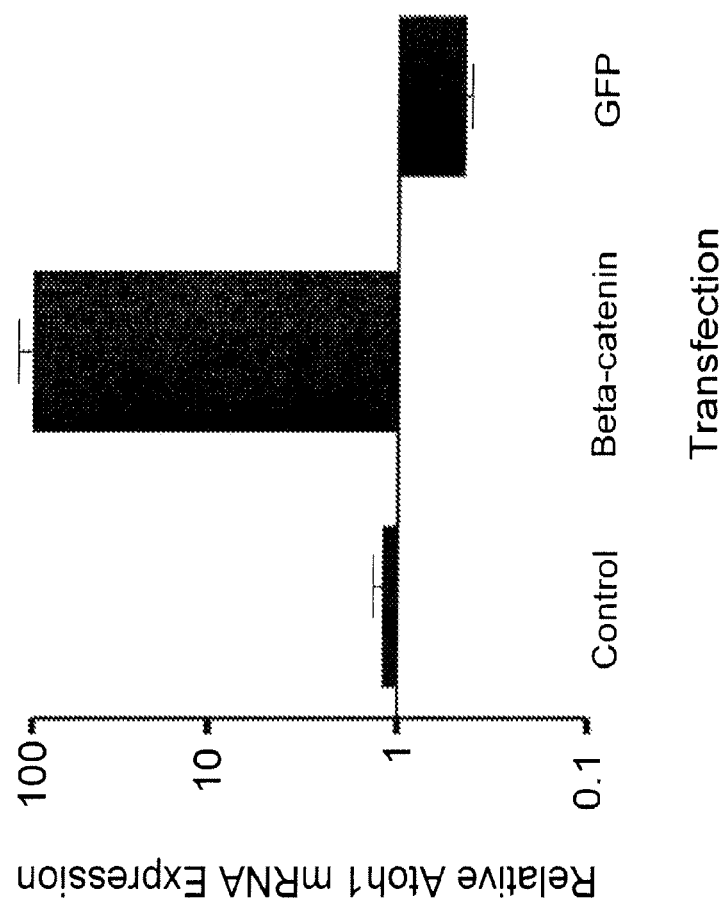
FIG. 2A is a bar graph showing Atoh1 expression in HEK cells quantified using real-time polymerase chain reaction (RT-PCR). Columns represent the mean of two independent experiments each performed in triplicate. Atoh1 levels are shown relative to control cells without transfection and are normalized to S18.
Figure 2B:
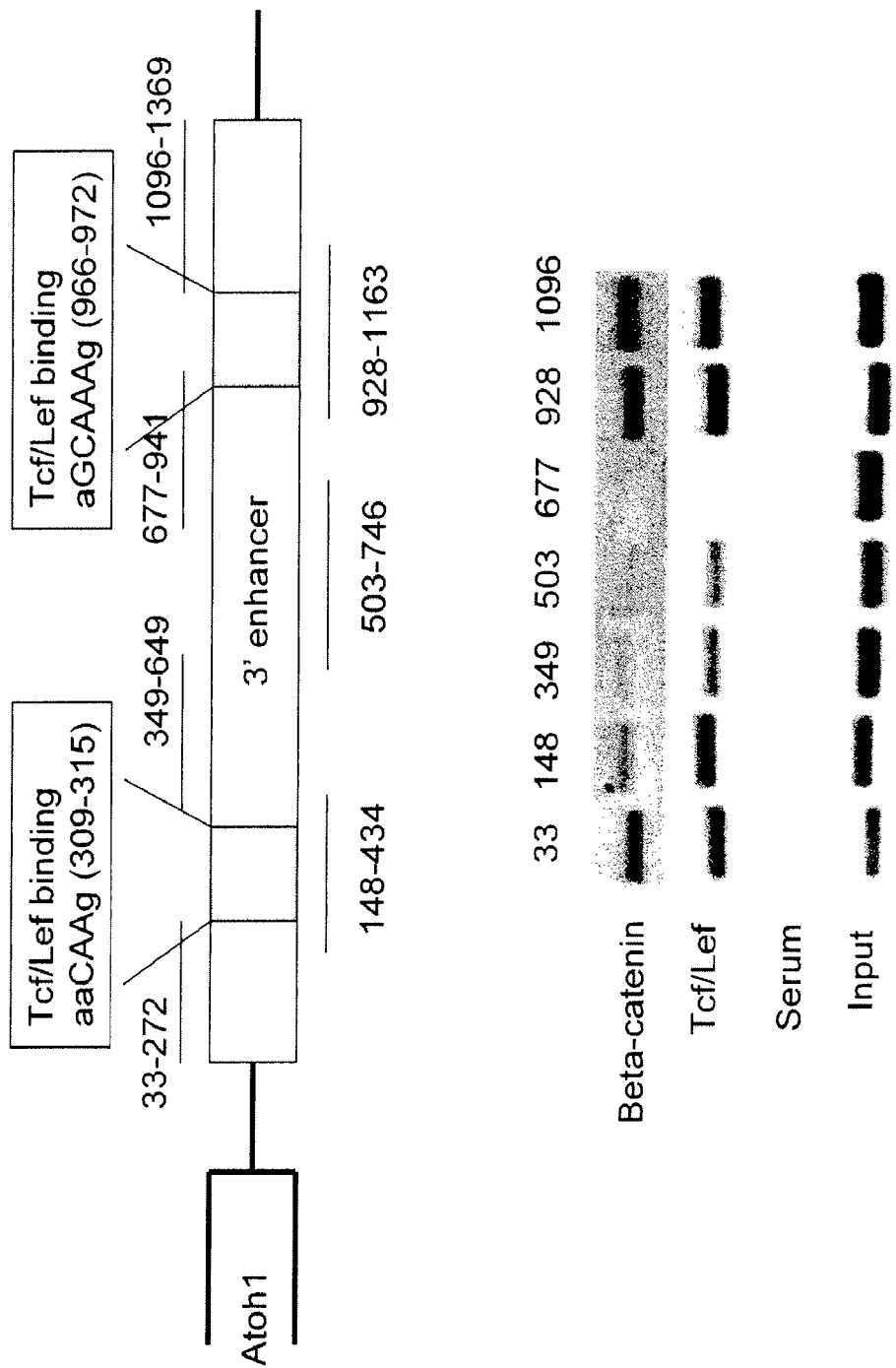
FIG. 2B is a schematic representation of the Atoh1 3' enhancer and an image of a gel showing Atoh1 bound to β-catenin, Tcf/Lef, or serum. Input (DNA without antibody precipitation) is shown as control.

As shown in FIG. 2B, β-catenin and Tcf-Lef antibody immunoprecipitated DNA at the 5' and 3' ends of the 1.3 kB sequence. This observation indicates that DNA in these regions has an affinity for both proteins. These sequences were not seen in control samples exposed to serum.

Atoh1 has a 1.7 kb regulatory enhancer located 3' to its coding region. This 3' Atoh1 enhancer is sufficient to direct expression of a heterologous reporter gene in transgenic mice (Helms et al., *Development*, 127:1185-1196, 2000). To define the binding sites on the mouse Atoh1 enhancer, the murine Atoh1 3' enhancer sequence (AF218258) was searched using MatInspector (Genomatix) software. These searches identified two candidate binding sites for β-catenin in combination with Tcf-Lef transcriptional coactivators at nucleotides 309-315 and 966-972 of AF218258. To determine whether these candidate sites had binding affinity for β-catenin we performed DNA pulldown assays with two biotin-labeled oligonucleotides probes, termed probe 309 and probe 966. Each of these probes contain sequence homologous to the candidate sites at nucleotides 309-315 and 966-972 of AF218258 and surrounding nucleotides. Probe 309 spans nucleotides 297-326 and probe 966 spans nucleotides 956-985 of AF218258. The sequences of probes 309 and 966 are as follows:

```
Probe 309
                                            (SEQ ID NO: 34)
5'-ATCACCCAAACAAACAAAGAGTCAGAACTT-3'

Probe 966
                                            (SEQ ID NO: 35)
5'-GTTAGGAGCCAGAAGCAAAGGGGTGACAC-3'
```

Both probe 309 and 966 encode five prime termini biotin labels. The sequences of the candidate β-catenin/Tcf-Lef binding sites (309-315 and 966-972) are shown in bold.

Pulldown assays were performed as follows. Nuclei were isolated from $10^6$ HEK and Neuro2a cells following mechanical disruption with a 20 gauge needle. Proteins were extracted from nuclei in 200 μl RIPA buffer with fresh proteinase inhibitors at 4° C. for 60 minutes. Chromatin DNA was pelleted at 14,000 g for 15 min at 4° C. and the nuclear lysate (supernatant) was collected. Biotin-labeled DNA probe (0.3 μg) with or without 10 μg unlabeled DNA probe was incubated with 40 μl nuclear lysate for 30 min at room temperature with gentle shake in binding buffer (10 mM Tris, 50 mM KCl, 1 mM DTT, 5% glycerol, pH 7.5, 40 mM 20 mer poly A and poly C) with proteinase inhibitors. Probe-bound proteins were collected with 50 Streptavidin magnetic beads (Amersham Pharmacia). Precipitated proteins were washed five times with binding buffer and boiled in 50 μl 2× sample buffer (BioRad), and the supernatant was collected for Western blotting.

Western blots were performed to detect proteins interacting with probes 309 and 966. Briefly, proteins were separated on 4-12% NuPAGE Bis-Tris gels (Invitrogen) and electrotransferred to 0.2 μm nitrocellulose membranes (Bio-Rad). The membranes were probed with mouse anti-Atoh1 antibody (Developmental Studies Hybridoma Bank), anti-Lef-1/Tcf antibody (Sigma L4270), or rabbit anti-β-catenin antibody (Sigma C2206), followed by HRP-conjugated anti-mouse (Sigma), anti-goat (Santa-Cruz) or anti-rabbit (Chemicon) antibodies. The blots were processed with ECL™ (Amersham Pharmacia) according to the manufacturer's instructions.

Figures 7A, 7B:
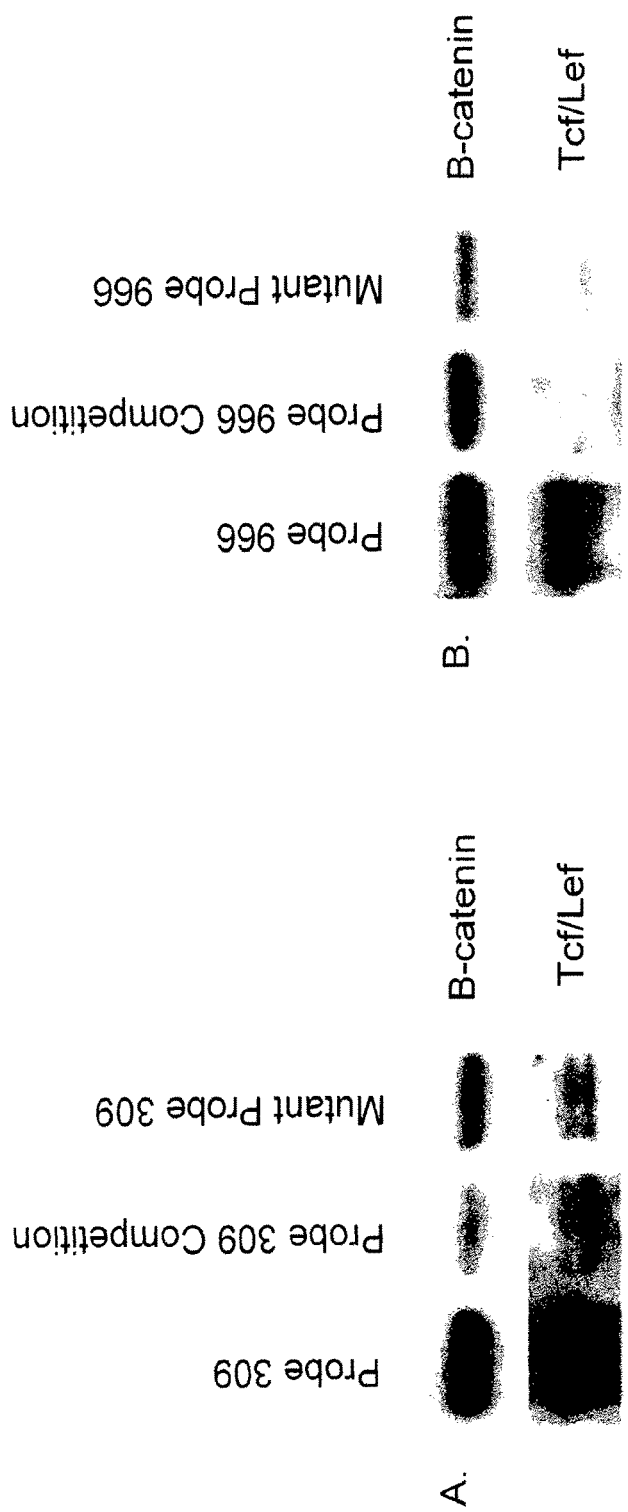
FIGS. 7A and 7B are images of immunoblots showing β-catenin and Tcf-Lef detection following DNA pull down. Left lanes show proteins pulled down using probe 309 (7A) and probe 966 (7B). Center lanes show probe 309 (7A) and probe 966 (7B) competition pull downs. Right lane show proteins pulled down using mutant probe 309 (7A) and mutant probe 966 (7B).

As shown in FIGS. 7A and 7B, left columns, both β-catenin and Tcf-Lef, respectively, were detected following DNA pull down using Western blotting. As shown in the center column of FIGS. 7A and 7B, binding of β-catenin and Tcf-Lef to the probes was reduced by competition with unlabelled probe. As shown in the right column of FIGS. 7A and 7B, mutation of the candidate binding sites (see SEQ ID NOs: 11 and 12) of probes 309 and 966 also reduced binding of β-catenin and Tcf-Lef to the probes. The sequences of the mutant 309 and 966 probes are as follows:

```
Mutant Probe 309
                                            (SEQ ID NO: 36)
5'-ATCACCCAAACACATACGAAGTCAGAACTT-3'

Mutant Probe 966
                                            (SEQ ID NO: 37)
5'-GTTAGGAGCCAGAGGATCGTGGGGTGACAC-3'

The sequences of the wild type probes
are as follows:
Wild Type Probe 309 (nucleotides 297-326)
                                            (SEQ ID NO: 38)
5'-ATCACCCAAACAAACAAGAGTCAGCACTT-3'

Wild Type Probe 966
                                            (SEQ ID NO: 39)
5'-GTTAGGAGCCAGAAGCAAAGGGGTGACTC-3'
```

The sequences of the mutated candidate β-catenin/Tcf-Lef binding sites (309-315 and 966-972) are shown in bold. Both mutant probes 309 and 966 encode five prime termini biotin labels. Thus, probe bound proteins were collected with Streptavidin magnetic beads (50 μL; Amersham-Pharmacia). Precipitated proteins were washed five times with binding buffer and boiled in 50 μL sample buffer. Supernatant was collected for Western blotting with anti-β-catenin antibody and anti-Lef-1-Tcf antibody.

The precise sequences within Atoh1 that have binding affinity for β-catenin and Tcf-Lef were identified using the above described DNA pulldown. Consistent with the observation reported above in HEK cells, in Neuro2a cell, as shown in FIG. 7C, probe 309 and 966 interacted with β-catenin and Tcf-Lef and this interaction was reduced by competition and destroyed by mutation.

The competition and mutation assays confirm the specificity of the DNA pull down assay.

These data suggest that both of the candidate binding sites identified in the Atoh1 enhancer region bound to β-catenin in the Tcf/Lef complex.

Figures 7C, 7D:
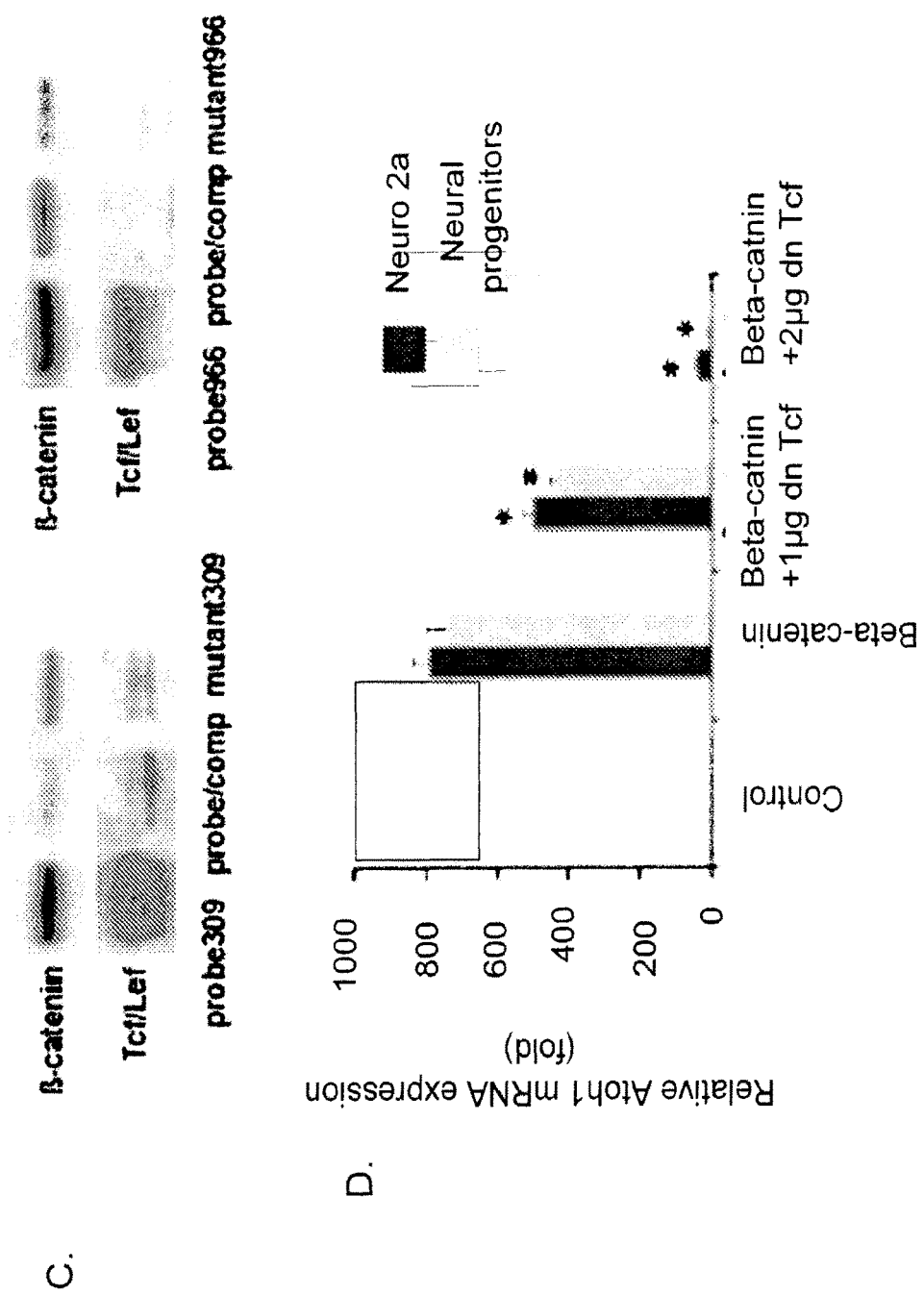
FIG. 7C is an image of gels showing Western blotting of β-catenin and Tcf-Lef.
FIG. 7D is a bar graph showing the expression of Atoh1 in untransfected Neuo2a cells and neural progenitors.
Figures 8A, 8B, 8C:
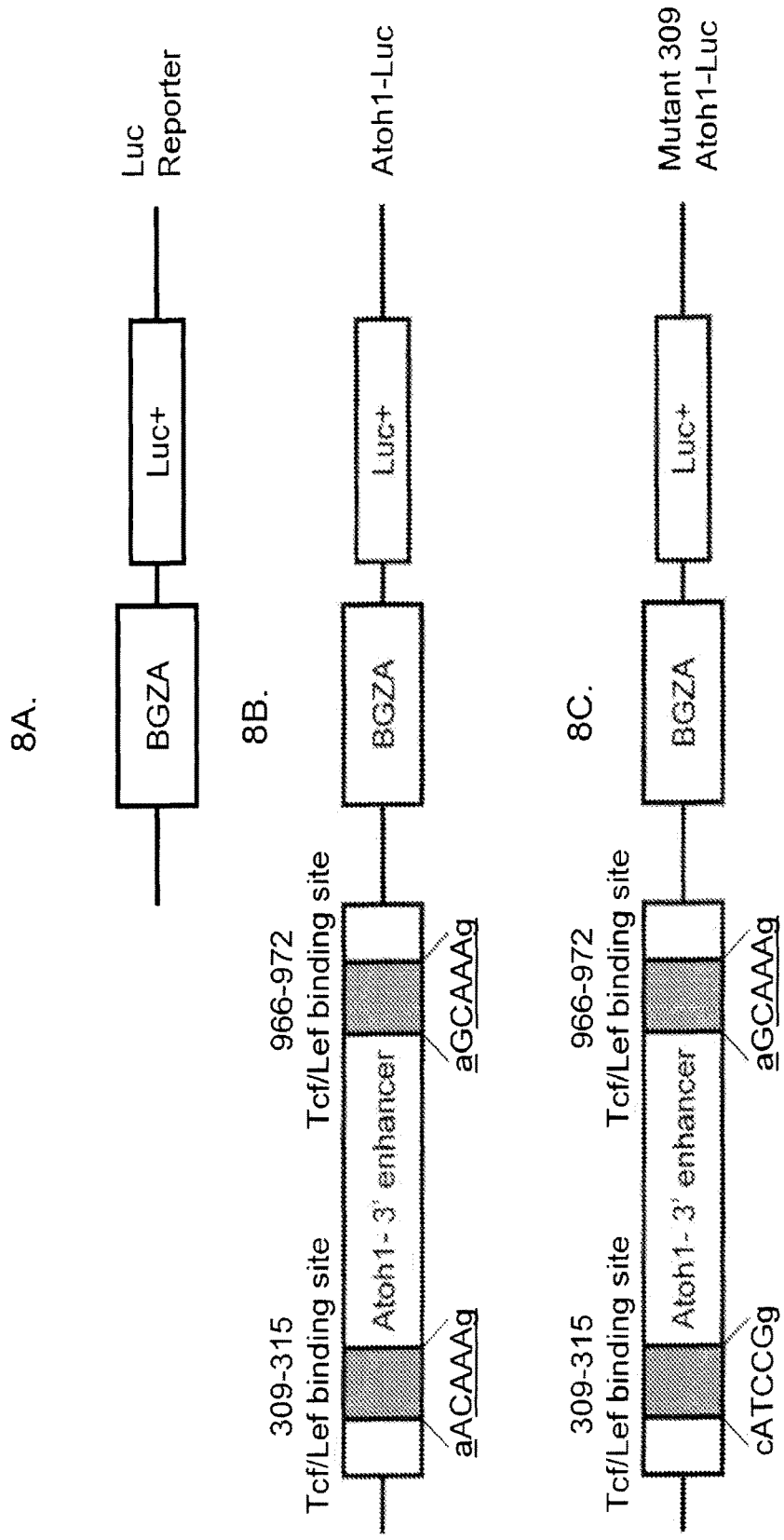
FIGS. 8A-8E are schematics showing luciferase reporter expression cassettes encoded by the luciferase vector pGL3. (8A) control luciferase reporter expression cassette encoding a β-globin promoter (BGZA) and a firefly luciferase gene (Luc+) in the absence of a Atoh1 3' enhancer. (8B) Wild type luciferase reporter expression cassette encoding a BGZA promoter (BGZA), Luc+, and a wild type Atoh1 3' enhancer. (8C) Mutant luciferase reporter expression cassette encoding a BGZA promoter (BGZA), Luc+, and a Atoh1 3' enhancer encoding a mutated first β-catenin binding site located at nucleotides 309-315 of AF218258. (8D) Mutant luciferase reporter expression cassette encoding a BGZA promoter (BGZA), Luc+, and a Atoh1 3' enhancer encoding a mutated second β-catenin binding site located at nucleotides 966-972 of AF218258. (8E) Mutant luciferase reporter expression cassette encoding a BGZA promoter (BGZA), Luc+, and a Atoh1 3' enhancer encoding mutated first and second β-catenin binding sites at nucleotides 309-315 and 966-972 of AF218258. Nucleotides encoded by the first and second β-catenin binding sites at nucleotides 309-315 and 966-972 of AF218258 are shown in upper case font. * indicates a mutated nucleotide. Nucleotides shown with * are mutant nucleotides.
Figures 8D, 8E:
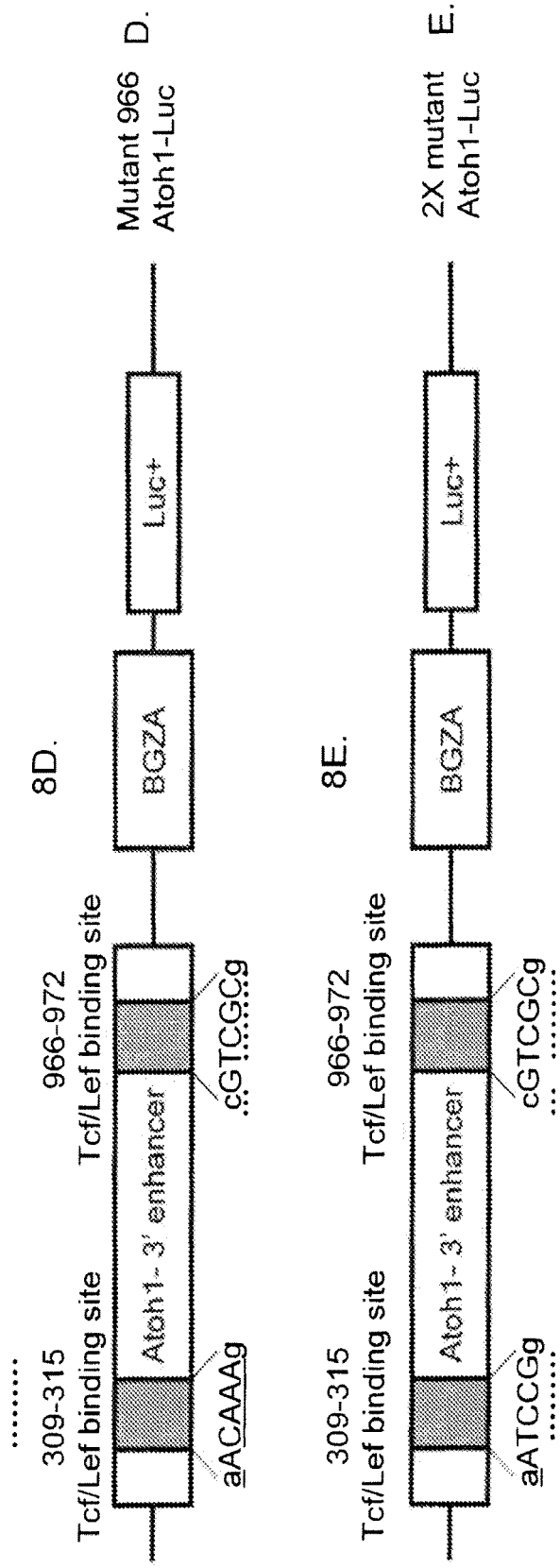

As shown in FIG. 7D, dominant negative Tcf4 suppressed β-catenin induced Atoh1 expression. Furthermore, inhibition was almost complete at higher levels, indicating that a complex between β-catenin and Tcf-Lef is required for activation of Atoh1 by β-catenin.

Example 5: β-catenin Modulates the Activity of the Atoh1 Enhancer Region

To determine whether the two confirmed β-catenin binding sites on the Atoh1 enhancer increased the functional activity of the Atoh1 enhancer, we constructed multiple Atoh1 enhancer-reporter genes with intact or mutated Atoh1 3' enhancers.

A construct with the Atoh1 3' enhancer controlling expression of the firefly luciferase gene (Luc) was made as follows. A BamH1/NcoI fragment containing the Atoh1 3' enhancer region (containing the β-catenin/Tcf-Lef binding sites identified above) with a basic β-globin promoter was excised from an Atoh1-GFP construct (Lumpkin et al., supra) and inserted into the luciferase vector, pGL3 (Promega), at BglII/NcoI in the multiple cloning region to create a Atoh1-luc vector.

A control Luc construct was made using the Atoh1-luc vector by excising the Atoh1 enhancer with BgII/EcoR1, followed by blunt end ligation. All the sequences were confirmed by sequencing.

Site-directed mutagenesis was performed using the QuickChange® II Site-Directed Mutagenesis Kit (Stratagene), according to the manufacturer's instructions. In short, the vector containing the target gene was denatured and annealed to the oligonucleotide primers that were designed according to the manfacturer's instructions, with the desired mutations in the complimentary strands. Following temperature cycling, circular DNA was generated from the template vector containing the incorporated mutagenic primers using PfuTurbo DNA polymerase, and methylated, parental DNA was digested with Dpn1 endonuclease. Finally the circular, nicked dsDNA was transformed into competent cells for repair. All mutations were confirmed after amplification by sequencing. Each of the β-catenin binding sites on the Atoh1 enhancer were mutated, alone or together, in a luciferase reporter construct, as indicated in FIGS. 8A-8E.

The wild type (WT) and mutant (MUT) constructs illustrated in FIG. 8 were then used to assess the functional activity of the Atoh1 enhancer by luciferase assay. Briefly, $10^5$ murine Neuro2a cells were seeded into a 24 well plate one day before transfection. 0.125 µg Atoh1-Luciferase reporter construct, 0.125 µg Renilla-Luciferase construct with or without 0.25 µg β-catenin expression construct were mixed with 0.5 µl Lipofectamine™ 2000 transfection reagent in 0.125 ml opti-MEM and incubated with the cells for 4 hr. Cells were lysed after 24 hr and luciferase activity was measured using the Dual Luciferase Reporter Assay System (Promega) in a TD-20/20 Luminometer (Turner Designs).

Figure 9:
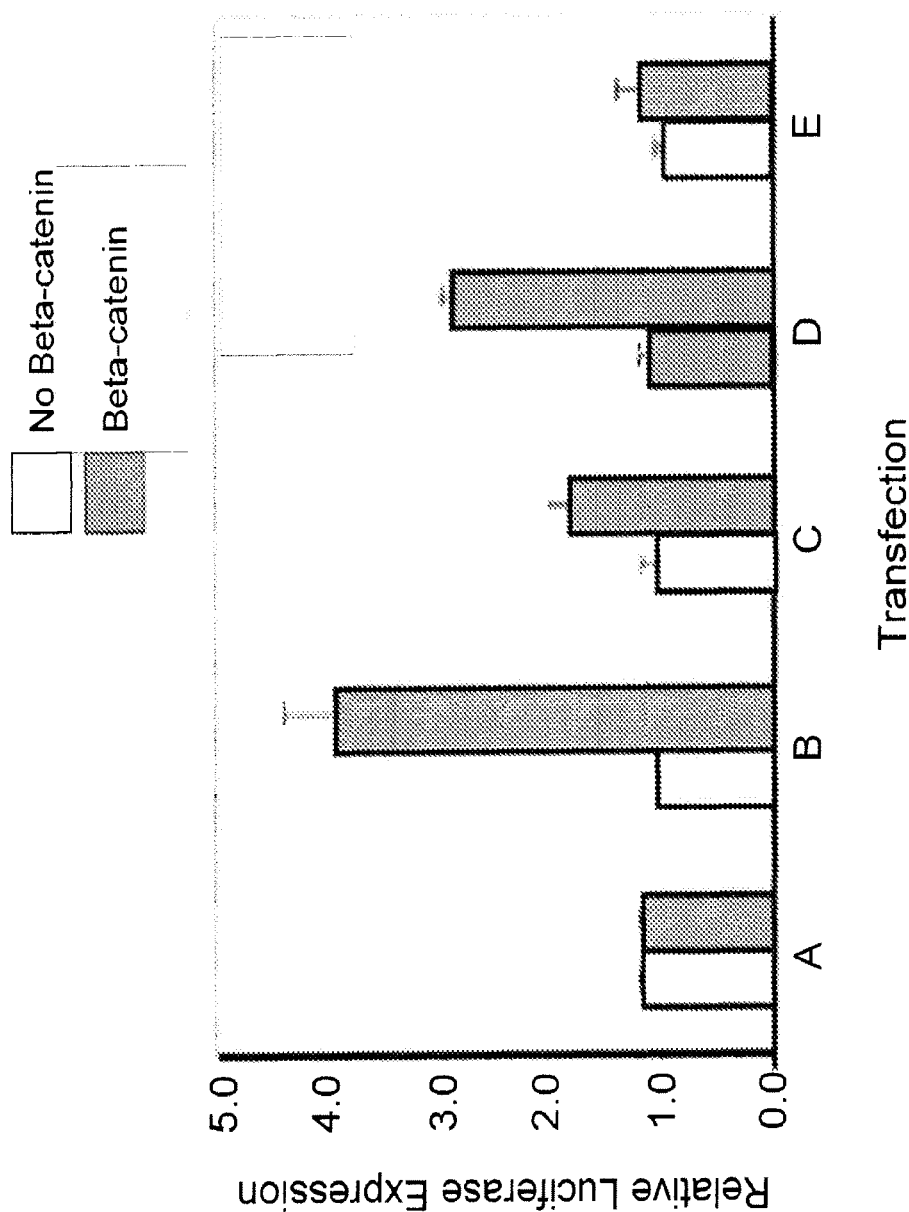
FIG. 9 is a bar graph showing relative luciferase expression in murine Neuro2a cells alone (open bars) or in the presence of β-catenin (solid bars). Cells were transfected with luciferase constructs (A)-(E) depicted in FIGS. 8A-8E.

As shown in FIG. 9, β-catenin had no effect on the control luciferase construct, which does not include the Atoh1 3' enhancer. Conversely, β-catenin increased reporter gene expression from the luciferase construct encoding the WT Atoh1 3' enhancer. β-catenin mediated Atoh1 3' enhancer reporter gene expression was reduced in the presence of β-catenin in all mutant constructs. β-catenin mediated upregulation was abolished in the double mutant construct.

These data indicate that β-catenin binding to the Atoh1 3' enhancer increases activity of the enhancer and that both of the β-catenin binding sites are required for maximum enhancer activity.

Example 6: A Combination of Notch Signaling Inhibition and β-Catenin Activity Promotes Enhanced Atoh1 Expression Notch signaling was inhibited using a γ-secretase inhibitor (DAPT) and β-catenin was activated using a GSK3β inhibitor (GSKi). Briefly, bone marrow derived MSCs that exhibit increased Atoh1 activity following the inhibition of Notch signaling were exposed to a γ-secretase inhibitor and a GSK3β inhibitor. Altered Notch activity was confirmed using CBF-1 luciferase reporter.

Mesenchymal stem cells (MSCs) were isolated from human bone marrow using the methods described by Jeon et al. (Mol. Cell. Neurosci., 34(1):59-68, (2007)). Cells were expanded once before use and cultured in MEM-α cell culture media (Sigma-Aldrich) supplemented with 9% horse serum, 9% fetal calf serum, and penicillin (100 U/mL) and streptomycin (100 µg/mL).

As shown in FIG. 10A, β-catenin expression was increased in cells exposed to γ-secretase inhibitor. Furthermore, as noted above, Atoh1 expression is increased by β-catenin. As shown in FIG. 10A, Atoh1 expression is further increased by a combination of β-catenin and Notch inhibition. To confirm the role of β-catenin in this observation, β-catenin expression was modulated using siRNA (as described in Example 3 above). The decrease in β-catenin is shown in FIG. 10B. As shown in FIG. 10C, suppression of β-catenin prevented any β-catenin expression following γ-secretase treatment and reduced Atoh1 expression. Similar results were also observed when Notch signaling was inhibited using non-γ-secretase inhibitors (see FIG. 10D). This result demonstrates the relationship between the inhibition of Notch signaling and β-catenin activity is not limited to the use of γ-secretase inhibitors.

Disruption of β-catenin mediated transcription by overexpression of dominant negative Tcf (dn Tcf) also reversed the increase in Atoh1 expression observed in cells treated with the inhibitor of Notch signaling (see FIG. 10E). Conversely, whereas β-catenin and Atoh1 expression were diminished following the elevation of Notch signaling, activation of β-catenin by Wnt3a rescued Atoh1 expression (see FIG. 10E).

These results suggest that the inhibition of Notch signaling combined with β-catenin activity may function synergistically to increase Atoh1 expression. Accordingly, combined therapy using Notch signaling inhibition and a β-catenin modulating compound, such as a β-catenin agonist, can be used to promote Atoh1 expression.

Example 7: β-catenin Promotes the Conversion of Inner Ear Stem Cells to Atoh1 Positive Cells in Transgenic Mice Mice that express nuclear green fluorescent protein (GFP) under the control of the Atoh1 enhancer (Atoh1-nGFP mice (Lumpkin et al., supra)) were used to assess the conversion of inner ear stem cells into hair cells. Increased expression of GFP in these animals indicates an increase in the activity of the Atoh1 3' enhancer. Inner ear stem cells derived from the transgenic animals were transduced with adenoviruses containing β-catenin or GFP under the control of a CMV promoter (Michiels et al., *Nat. Biotec.*, 20:1154-1157, 2002).

Inner ear stem cells were isolated from Atoh1-nGFP as previously described (Li et al., *Nat. Med.*, 9:1293-1299, 2003). Briefly utricles were dissected from 4 Atoh1-nGFP mice at postnatal day four (P4) and were trypsinized into a single cell suspension. The released cells were then grown in suspension for seven days in DMEM/FD12 medium (1:1) supplemented with N2/B27, 10 ng/mL FGF-2 (Chemicon), 50 ng/mL IGF (Chemicon), and 20 ng/mL EGF (Chemicon) to obtain spheres.

Inner ear stem cells isolated as spheres were seeded into a four-compartment 35 mm tissue culture dish and grown as a monolayer in DMEM/N2 medium. $10^6$ cells were infected with β-catenin, GFP or empty adenoviruses ($9 \times 10^7$ viral particles) in 100 µL Opti-MEM for 16 hours.

Figures 11A, 11B, 11C, 11D:
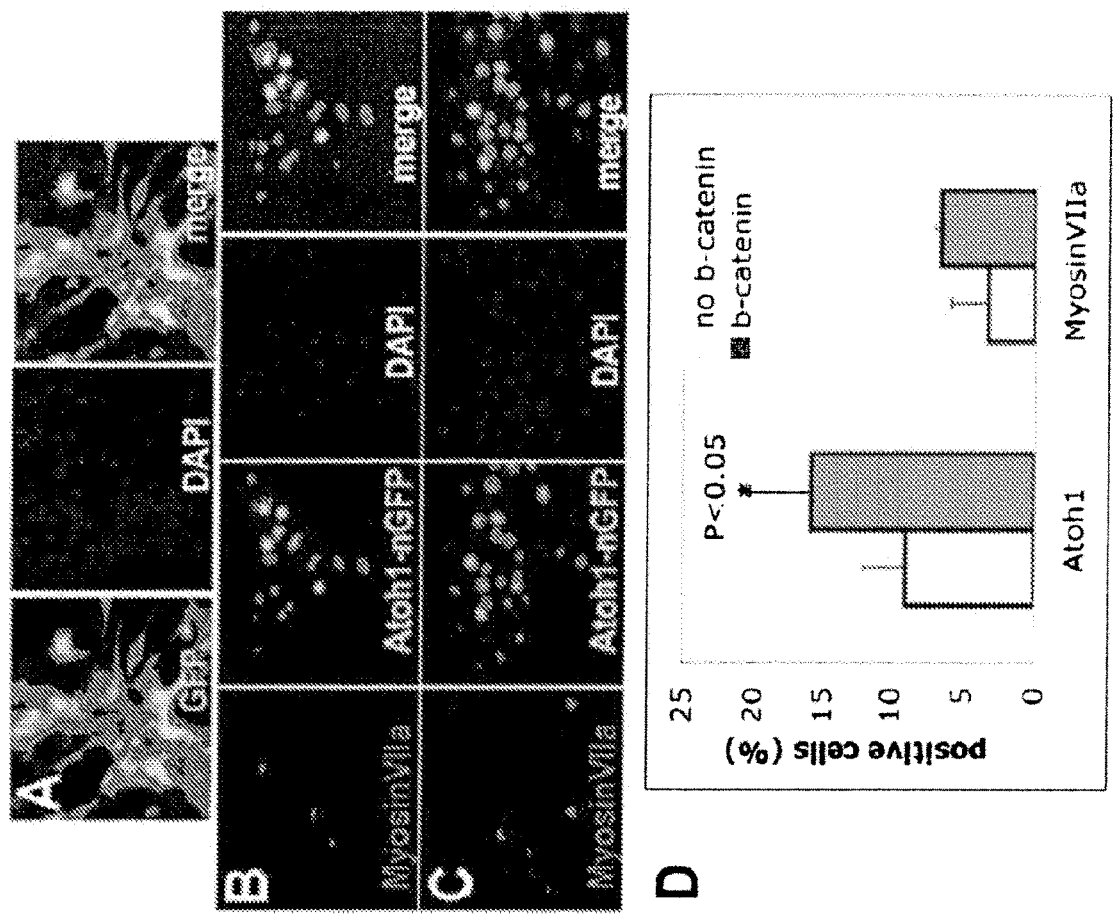
FIGS. 11A-11C are images of inner ear stem cells expressing fluorescent markers. (11A) Cells infected with adenoviruses encoding GFP. Left panel shows inner ear stem cells expressing green fluorescent protein (GFP); center panel shows cells stained with the nuclear stain 4'-6-Diamidino-2-phenylindole (DAPI—blue); right panel shows a merge of the left and center panels. (11B) and (11C) left panels show cells stained for myosin VIIa (red); second panels show Atoh1-nGFP positive cells (green); third panels show cells stained with DAPI; right panels show merged cells (red, green and blue). Triple stained cells are shown with arrows. (11B) cells infected with empty adenovirus vector. (11C) cells infected with adenoviruses encoding human β-catenin.
FIG. 11D is a bar graph showing quantification of Atoh1 and myosin VIIa double stained cells. Data represents three independent experiments in which 5000 cells were counted.

As shown in FIG. 11A, transduction of inner ear stem cells with the control GFP adenovirus resulted in GFP expression in 68% of the cells. As shown in FIG. 5C, transduction of inner ear stem cells with β-catenin adenovirus increased the number of Atoh1 positive cells compared to inner ear stem cells transduced with empty virus. This data suggests that β-catenin increased Atoh1 activity in inner ear stem cells obtained from Atoh1-nGFP mice. This observation is consistent with the differentiation of inner ear stem cells to hair cells. To further confirm the differentiation of the inner ear stem cells to hair cells, transduced cells were analyzed using immunocytochemistry to detect hair cell specific markers. Immunostaining was performed using rabbit antibody to myosin VII1 (Proteus Bioscience) at a 1:1000 dilution or mouse monoclonal antibody PC10 to detect PCNA (eBioscience) at a 1:100 dilution. Positively stained cells were counted using MetaMorph Imaging 7.0 and statistics were performed from three independent experiments.

As shown in FIG. 11D, when 5000 cells were counted in three independent experiments, the number of cells staining positive for Atoh1 and myosin VIIa doubled in cells expressing β-catenin (Atoh1 positive cells increased from 8.9% to 15.8% and myosin VIIa positive cells increased from 3.3% to 6.6%). As Atoh1 and myosin VIIa are known specific hair cell markers, this observation confirms that β-catenin promotes the differentiation of inner ear stem cells into hair cells. To correlate β-catenin overexpression with the conversion of inner ear progenitor cells into Atoh1 positive cells, an expression vector encoding the Ji-catenin coding region followed by the reporter sequence IRES-DsRed was constructed.

The β-catenin-IRES-DsRed construct was by cloning human β-catenin cDNA containing Xba I (enzymes from New England Biolabs) sticky ends into pIRES2-DsRed Express (Clontech) at the Nhe I site.

Inner ear stem cells isolated and seeded as described above where transfected with 4 µg IRES-DsRed empty vector or 4 µg β-catenin-IRES-DsRed using 3 µL, Lipofectamine™ 2000 transfection reagent in 100 µL, Opti-MEM for 4 hours. Transfected cells were then analyzed by immunocytochemistry after 5 days. Immunostaining was performed as described above.

Figures 12A, 12B:
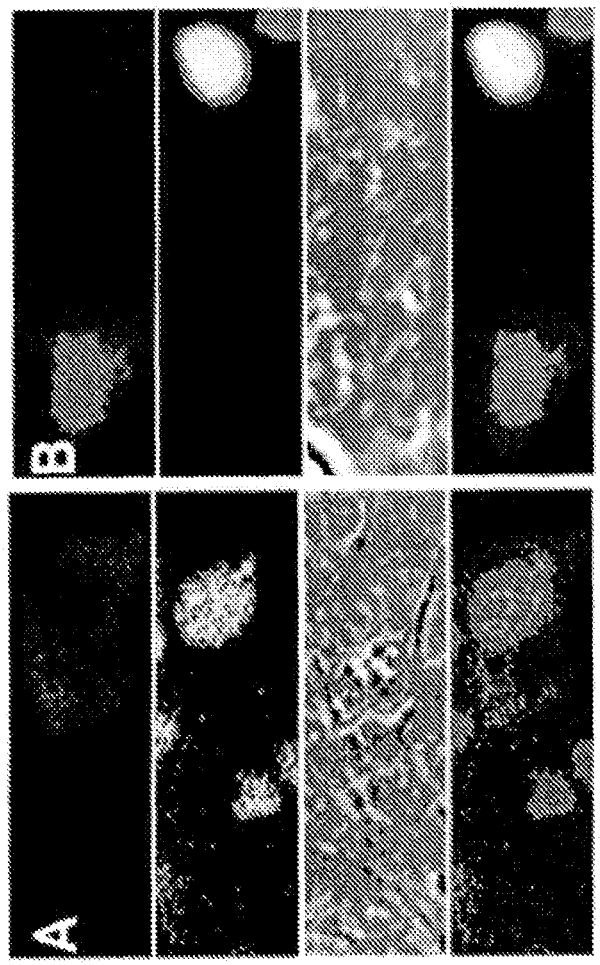
FIGS. 12A and 12B are images of inner ear stem cells expressing β-catenin-IRES-DsRed (12A) and IRES-DsRed in the absence of β-catenin (12B). (i) shows cells expressing β-catenin-IRES-DsRed or IRES-DsRed (red). One cell is shown for both (12A) and (12B). (ii) shows Atoh1 expression (green) in the same field of view as (i). (iii) shows a phase contrast image of the same field of view as (i) and (ii). (iv) shows a merged image of (i), (ii), and (iii). Co-stained cells are shown with arrows.

As shown in FIG. 12B and Table 1, none of the 14 cells expressing IRES-DsRed empty vector stained positively for Atoh1. In contrast, as shown in FIG. 12A and table 1, 8 of 15 cells expressing β-catenin-IRES-DsRed stained positively for Atoh1.

TABLE 1

Quantification of β-Catenin-Mediated Atoh1
Expression in Inner Ear Stem Cells

| Transfection | DsRed Positive Cells (Red) | Atoh1 Positive Cells (Green) |
|---|---|---|
| β-catenin-IRES-DsRed | 14 | 8 |
| IRES-DsRed | 15 | 0 |

N = 3;
cells counted = 1000.

To ascertain whether the increase in Atoh1 positive cells observed above was due to increased proliferation of the inner ear stem cells, as has been reported for other neural progenitor cells (Adachi et al., *Stem Cells*, 25:2827-36, 2007; Woodhead et al., *J. Neurosci.*, 26:12620-12630, 2006), labeling for PCNA was assessed in β-catenin expressing cells.

Adenovirus mediated β-catenin expression resulted in 68±7.9% PCNA positive cells, which was not significantly different (p>0.05) from cells transduced with empty adenovirus (69.7±5.2% PCNA positive cells) and non-transduced cells (72±8.8% PCNA positive cells) based on three independent experiments in which 5000 cells were counted.

This data suggests that cell proliferation was not required for β-catenin mediated cell differentiation.

Example 8: β-Catenin Mediated Hair Cell Formation

Figures 13A, 13B, 13C, 13D:
FIGS. 13A-13D are images of hair cells in the organ of corti disected at E16 in Atoh1-nGFP mice. (13A) untreated control hair cells; (13B) hair cells infected with empty adenoviral vector for 5 days; (13C and D) hair cells infected with adenovirus encoding β-catenin for 5 days. Green cells are Atoh-1 positive hair cells.

As shown in FIG. 13, β-catenin expression promoted the formation of extra rows of outer hair cells at E16. 8.1 E+07 adenovirus particles were applied to organ of Corti dissected from E16 Atoh1-nGFP embryos and cultured for 5 days. Adenovirus encoding As shown in FIGS. 13C and 12D, β-catenin increased the number of Atoh1 positive outer hair cells compared to untreated (A) or cells treated with empty adenovirus (B).

Figures 14A, 14B:
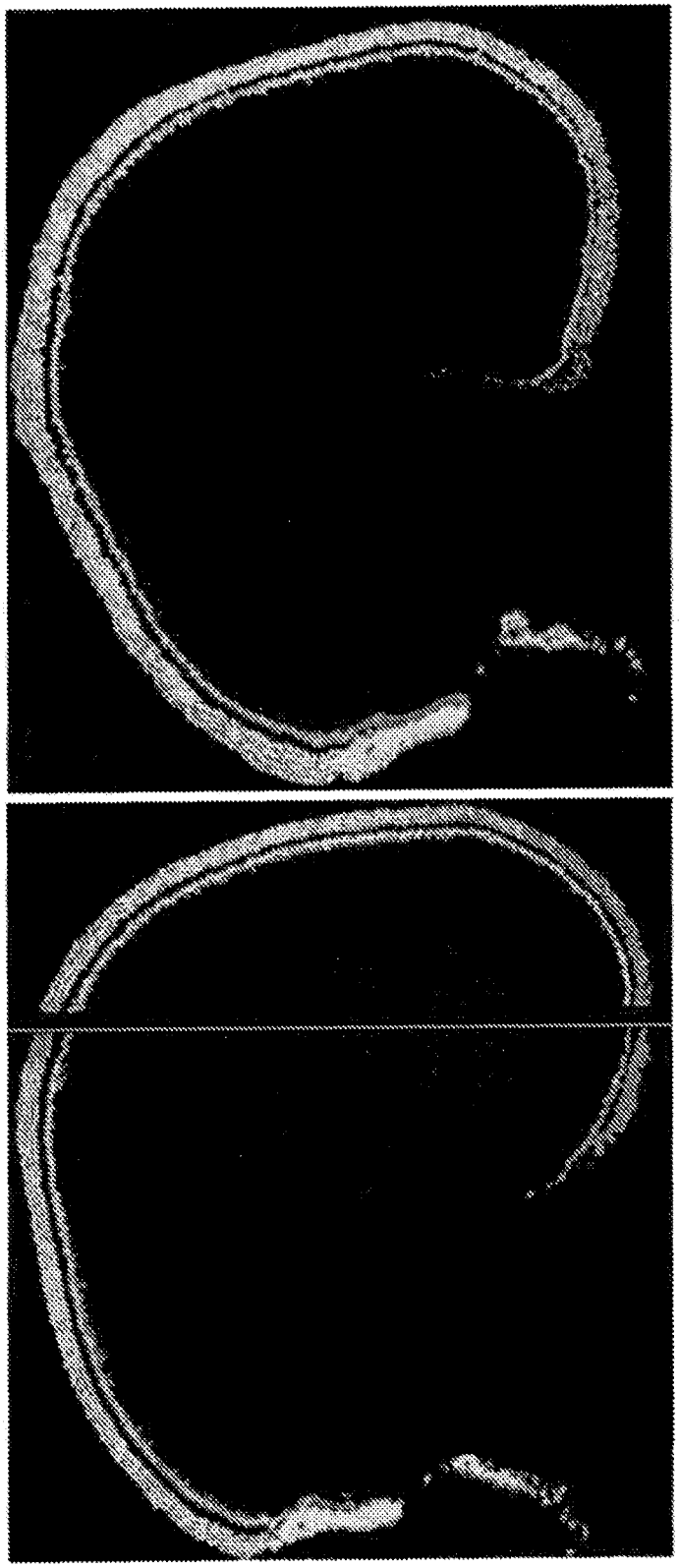
FIGS. 14A and 14B are images of different organs of corti dissected from Atoh1-nGFP mice. (14A) shows a dissected organ of corti 2 days post infected with β-catenin (14B) shows an uninfected organ of corti.
Figure 15A:
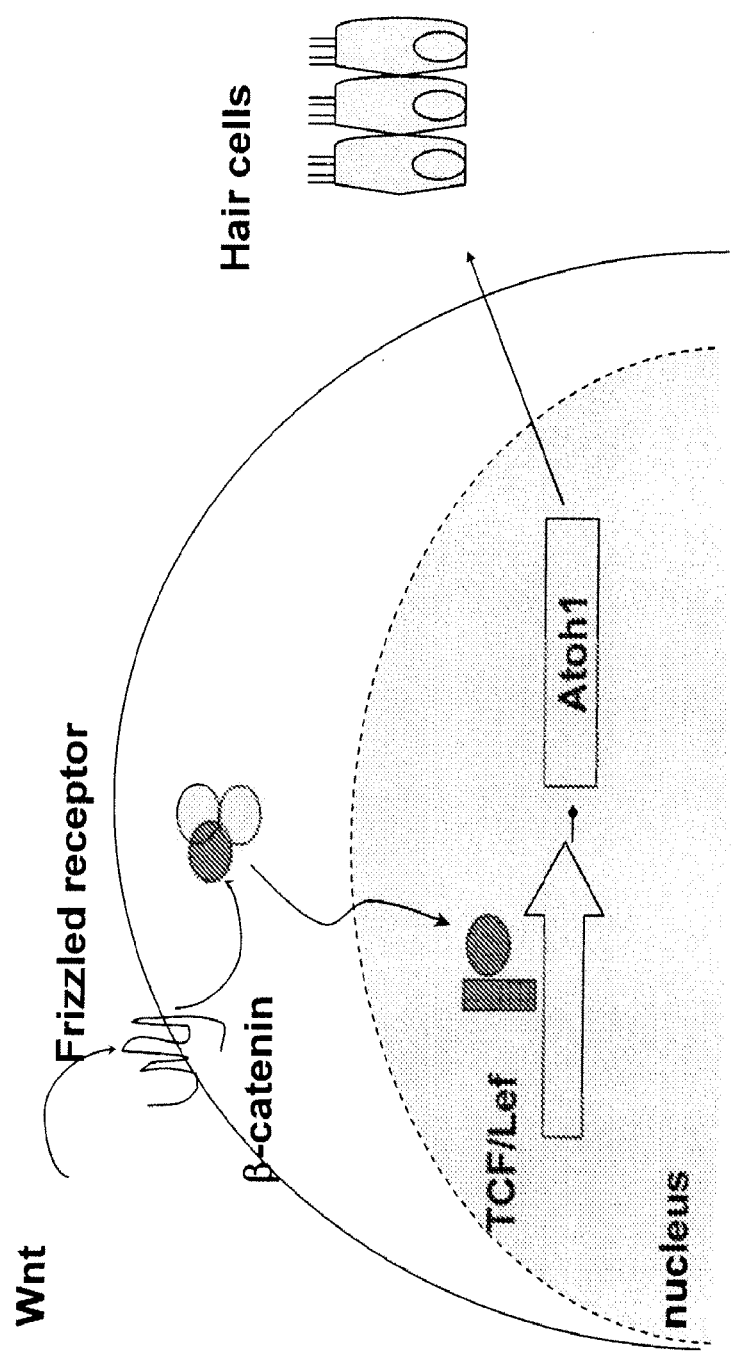
FIGS. 15A and 15B are images showing putative WNT/β-catenin signaling pathways. 15B illustrates regulation of Atoh1 by β-catenin according to the data presented herein.
Figure 15B:
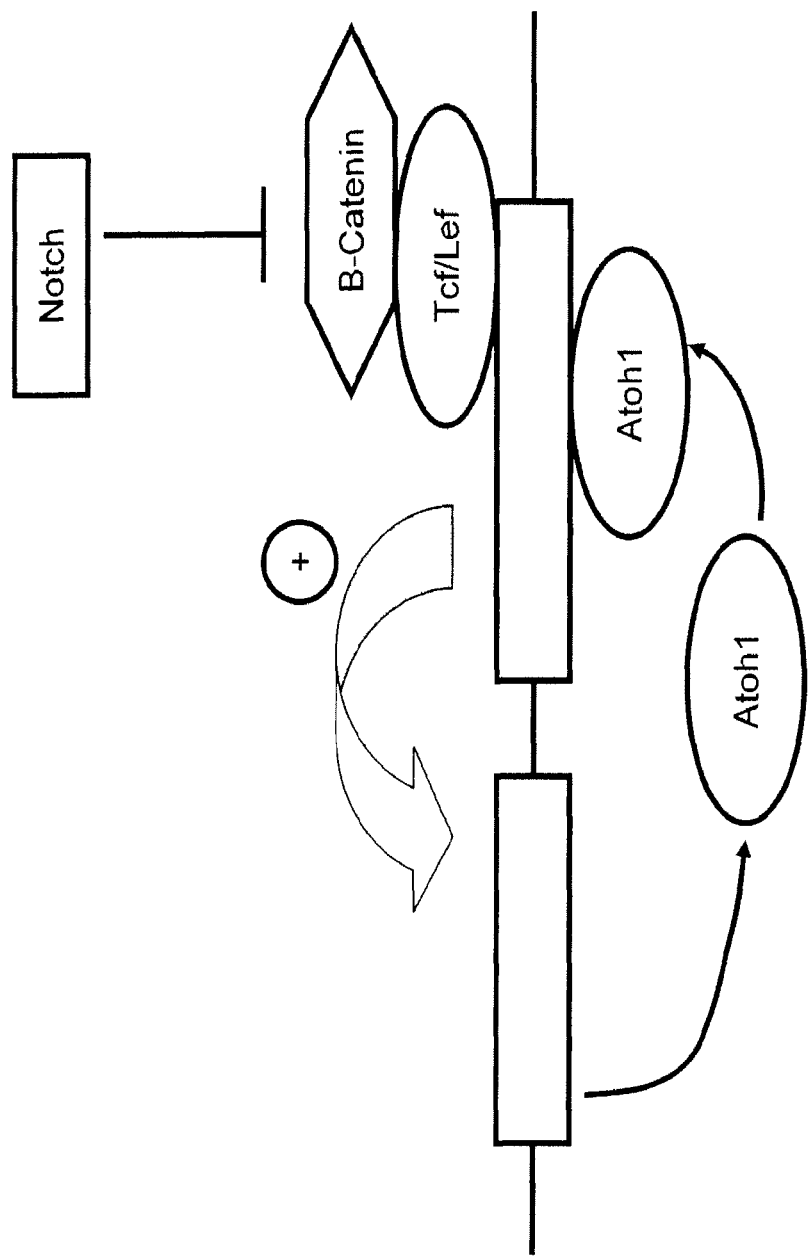

As shown in FIG. 14 and table 2, 8.1E+07 adenovirus particles were used to infect organs of Corti dissected from E16 Atoh1-nGFP embryos that were then cultured for 5 days. Images were captured prior to infected (see FIG. 13B) and 5 days post-infected (see FIG. 13A). The results were quantified and are shown in Table 2. As shown in Table 2, a 32±3.1% increase was observed following treatment.

TABLE 2

| Treatment with Ad-β-catenin | Pre-infected | Post-infection |
|---|---|---|
| IHC | 256 | 249 |
| OHC | 768 | 1014 |

N = 3.

Example 9: Assessment of the Combined Affect of β-Catenin and Inhibitors of the Notch Signaling Pathway on the Conversion of Inner Ear Stem Cells to Atoh1 Positive Cells in Transgenic Mice Mice that express nuclear green fluorescent protein (GFP) under the control of the Atoh1 enhancer (Atoh1-nGFP mice (Lumpkin et al., supra)) were processed as described in Example 9.

Inner ear stem cells isolated as spheres were seeded into a four-compartment 35 mm tissue culture dish and grown as a monolayer in DMEM/N2 medium. $10^6$ cells were infected with combinations of a β-catenin adenovirus or one or more β-catenin modulating compounds, GFP adenovirus, empty adenoviruses ($9\times10^7$ viral particles) and an inhibitor of the Notch signaling pathway in 100 µL Opti-MEM for 16 hours, as shown in Table 3 (X indicates cells are treated):

TABLE 3

| Well No. | β-catenin | GFP adenovirus | Empty Adenovirus | Notch inhibitor |
|---|---|---|---|---|
| 1 | X | | | |
| 2 | | X | | |
| 3 | | | X | |
| 4 | | | | X |
| 5 | X | | | X |
| 6 | | X | | X |
| 7 | | | X | X |

Following treatment, cells were analyzed for Atoh1 and myosin VIIa expression.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A method of treating a subject who has hearing loss as a result of loss of auditory hair cells, the method comprising:
   identifying a subject who has hearing loss as a result of loss of auditory hair cells;
   administering to the middle or inner ear of the subject a composition comprising one or more glycogen synthase kinase 3 β (GSK3β) inhibitors in an amount effective to increase the number of auditory hair cells in the subject;
   thereby treating the hearing loss as a result of loss of auditory hair cells in the subject.

2. The method of claim 1, wherein the subject has sensorineural hearing loss, auditory neuropathy, or both, as a result of loss of auditory hair cells.

3. The method of claim 1, wherein the composition further comprises a β-catenin polypeptide.

4. The method of claim 1, wherein the composition is injected into the luminae of the cochlea.

5. The method of claim 1, wherein the one or more GSK3β inhibitor is selected from the group of lithium chloride, purvalanol A, olomoucine, alsterpaullone, kenpaullone, benzyl-2-methyl-1,2,4-thiadiazolidine-3,5-dione, 2-thio(3-iodobenzyl)-5-(1-pyridyl)-[1,3,4]-oxadiazole, 2,4-dibenzyl-5-oxothiadiazolidine-3-thione, (2'Z,3'E)-6-bromoindirubin-3'-oxime (BIO), a 4 dibromoacetophenone, 2-chloro-1-(4,5-dibromo-thiophen-2-yl)-ethanone, N-(4-nethoxybenzyl)-N'-(5-nitro-1,3-thiazol-2-yl)urea, 4-benzyl-2-methyl-1,2,4-thiadiazolidine-3,5-dione, 2-thio(3-iodobenzyl)-5-(1-pyridyl)-[1,3,4]-oxadiazole, 2,4-dibenzyl-5-oxothiadiazolidine-3-thione, α-4-dibromoacetophenone, 2-chloro-1-(4, 5-dibromo-thiophen-2-yl)-ethanone, and N-(4-Methoxybenzyl)-N'-(5-nitro-1,3-thiazol-2-yl)urea.

6. The method of claim 1, wherein the one or more GSK3β inhibitor is an indirubin.

7. The method of claim 6, wherein the indirubin is selected from the group consisting of: indirubin-5-sulfonamide, indirubin-5-sulfonic acid (2-hydroxyethyl)-amide, indirubin-3'-monoxime; 5-iodo-indirubin-3'-monoxime, 5-fluoroindirubin, 5, 5'-dibromoindirubin, 5-nitroindirubin, 5-chloroindirubin, 5-methylindirubin, and 5-bromoindirubin.

8. The method of claim 1, wherein the method comprises administering the composition to the middle ear of the subject.

9. The method of claim 1, wherein the method comprises administering the composition to the inner ear of the subject.

10. The method of claim 5, wherein the GSK3β inhibitor is (2'Z,3'E)-6-bromoindirubin-3'-oxime (BIO).

11. The method of claim 1, wherein the auditory hair cell expresses atonal protein homologue 1 (Atoh1).

12. The method of claim 1, wherein the composition further comprises an inhibitor of the Notch signaling pathway.

13. The method of claim 12, wherein the inhibitor of the Notch signaling pathway is a γ-secretase inhibitor.

* * * * *

UNITED STATES PATENT AND TRADEMARK OFFICE
CERTIFICATE OF CORRECTION

PATENT NO. : 10,143,711 B2
APPLICATION NO. : 13/130607
DATED : December 4, 2018
INVENTOR(S) : Albert Edge and Fuxin Shi Page 1 of 1

It is certified that error appears in the above-identified patent and that said Letters Patent is hereby corrected as shown below:

In the Claims

In Column 57, Line 63, Claim 5, delete "a 4 dibromoacetophenone," and insert
-- α-4-dibromoacetophenone, --, In Column 57, Line 65, Claim 5, delete "nethoxybenzyl)" and insert -- methoxybenzyl) --, In Column 58, Line 40 (approx.), Claim 5, delete "(4, 5-dibromo" and insert -- (4,5-dibromo --, In Column 58, Line 43 (approx.), Claim 6, delete "GSK3P" and insert -- GSK3β --.

Signed and Sealed this
Third Day of September, 2019

Andrei Iancu
*Director of the United States Patent and Trademark Office*